United States Patent
Flygare et al.

(10) Patent No.: US 11,090,322 B2
(45) Date of Patent: Aug. 17, 2021

(54) ANTHRACYCLINE DISULFIDE INTERMEDIATES, ANTIBODY-DRUG CONJUGATES AND METHODS

(71) Applicant: Genentech, Inc., South San Francisco, CA (US)

(72) Inventors: John A. Flygare, Burlingame, CA (US); Thomas H. Pillow, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 282 days.

(21) Appl. No.: 16/178,328

(22) Filed: Nov. 1, 2018

(65) Prior Publication Data

US 2019/0054102 A1 Feb. 21, 2019

Related U.S. Application Data

(62) Division of application No. 14/851,206, filed on Sep. 11, 2015, now Pat. No. 10,149,913.

(60) Provisional application No. 62/049,720, filed on Sep. 12, 2014.

(51) Int. Cl.
*A61K 31/704* (2006.01)
*A61K 47/68* (2017.01)

(52) U.S. Cl.
CPC ........ *A61K 31/704* (2013.01); *A61K 47/6809* (2017.08); *A61K 47/6849* (2017.08); *A61K 47/6855* (2017.08)

(58) Field of Classification Search
CPC ...... A61K 31/00; A61K 31/704; A61K 47/00; A61K 47/6849; A61K 47/6855; A61K 47/6809; A61P 35/00
USPC ........................................................ 424/181
See application file for complete search history.

(56) References Cited

U.S. PATENT DOCUMENTS

| | | | |
|---|---|---|---|
| 5,122,368 A | 6/1992 | Greenfield et al. | |
| 6,630,579 B2 | 10/2003 | Chari et al. | |
| 7,223,837 B2 | 5/2007 | De Groot et al. | |
| 7,521,541 B2 | 4/2009 | Eigenbrot et al. | |
| 8,389,697 B2 | 3/2013 | Beria et al. | |
| 8,470,984 B2 | 6/2013 | Caruso et al. | |
| 8,742,076 B2 | 6/2014 | Cohen et al. | |
| 8,900,589 B2 | 12/2014 | Beria et al. | |
| 2007/0060534 A1 | 3/2007 | Matteucci et al. | |
| 2010/0034837 A1* | 2/2010 | Beria ................. | C07K 16/2863 424/181.1 |
| 2016/0074528 A1 | 3/2016 | Flygare et al. | |

FOREIGN PATENT DOCUMENTS

| | | | |
|---|---|---|---|
| WO | 1998002446 A1 | 1/1998 | |
| WO | 2009025669 A1 | 2/2009 | |
| WO | WO-2009025669 A1 * | 2/2009 | ............. A61K 47/60 |
| WO | 2009099741 A1 | 8/2009 | |
| WO | 2010009124 A2 | 1/2010 | |

OTHER PUBLICATIONS

Patani, George A. And LaVoie, Edmond J., Bioisosterism: a rational approach in drug design., Chem, Rev. 1996, 96, 3147-3176 (Year: 1996).*
Dubowchik, et al., "Doxorubicin Immunoconjugates Containing Bivalent, Lysosomally-Cleavable Dipeptide Linkages", Bioorganic & Medicinal Chemistry Letters 12, 1529-1532 (2002).
Flygare, et al., "Antibody-Drug Conjugates for the Treatment of Cancer", Chem Biol Drug Des 81, 113-121 (2013).
International Search Report, for WO2016/040825, PCT/US2015/049728, dated Nov. 26, 2015.
Jeffrey, et al., "Dipeptide-based highly potent doxorubicin antibody conjugates", Bioorganic & Medicinal Chemistry Letters 16, 358-362 (2006).
Junttila, et al., "Targeting LGR5+ cells with an antibody-drug conjugate for the treatment of colon cancer", Sci Transl Med 7(314), 314ra186 (2015).
Kratz, et al., "Prodrugs of anthracyclines in cancer chemotherapy", Curr Med Chem 13, 477-523 (2006).
Pillow, et al., "Site-specific trastuzumab maytansinoid antibody-drug conjugates with improved therapeutic activity through linker and antibody engineering", J Med Chem 57(19), 7890-7899 (2014).
Quintieri, et al., "Formation and Antitumor Activity of PNU-159682, a Major Metabolite of Nemorubicin in Human Liver Microsomes", Clinical Cancer Research 11, 1608-1617 (2005).
Torgov, et al., "Generation of an intensely potent anthracycline by a monoclonal antibody—beta—galactosidase conjugate", Bioconjugate Chem 16, 717-721 (2005).
Willner, et al., "(6-Maleimidocaproyl)hydrazone of doxorubicin—a new derivative for the preparation of immunoconjugates of doxorubicin", Bioconjug Chem 4(6), 521-527 (1993).
Yu, et al., "A Novel Anti-CD22 Anthracycline-Based Antibody-Drug Conjugate (ADC) That Overcomes Resistance to Auristatin-Based ADCs", Clin Cancer Res 21(14), 3298-3306 (2015).

* cited by examiner

*Primary Examiner* — Misook Yu
*Assistant Examiner* — Cheng Lu
(74) *Attorney, Agent, or Firm* — Viksnins Harris Padys Malen LLP

(57) ABSTRACT

The invention provides antibody-drug conjugates comprising an antibody conjugated to an anthracycline drug moiety via a disulfide linker, anthracycline disulfide intermediates, and methods of using the antibody-drug conjugates.

15 Claims, 5 Drawing Sheets

Specification includes a Sequence Listing.

ANTHRACYCLINE DISULFIDE INTERMEDIATES, ANTIBODY-DRUG CONJUGATES AND METHODS

CROSS REFERENCE TO RELATED APPLICATIONS

This application is a divisional of U.S. Ser. No. 14/851,206, filed 11 Sep. 2015, which claims the benefit under 35 USC § 119(e) of U.S. Provisional Application Ser. No. 62/049,720 filed on 12 Sep. 2014. The entire content of the applications referenced above are hereby incorporated by reference.

SEQUENCE LISTING

The instant application contains a Sequence Listing which has been submitted electronically in ASCII format and is hereby incorporated by reference in its entirety. Said ASCII copy, created on Sep. 4, 2015, is named P05813-US_SL.txt and is 16,012 bytes in size.

FIELD OF THE INVENTION

The invention relates generally to antibodies conjugated to anthracycline disulfide intermediates to form antibody-drug conjugates with therapeutic or diagnostic applications. The antibodies may be engineered with free cysteine amino acids, reactive for conjugation with the anthracycline disulfide intermediates. The invention also relates to methods of using the antibody-drug conjugate compounds for in vitro, in situ, and in vivo diagnosis or treatment of mammalian cells, or associated pathological conditions.

BACKGROUND OF THE INVENTION

Antibody drug conjugates (ADC) are targeted chemotherapeutic molecules combining the properties of both antibodies and cytotoxic drugs by targeting potent cytotoxic drugs to antigen-expressing tumor cells, internalization, and release of drug, thereby enhancing their anti-tumor activity (Carter, P. and Senter, P. (2008) The Cancer Jour. 14(3):154-169). Successful ADC development for a given target antigen depends on optimization of antibody selection, linker design and stability, cytotoxic drug potency and mode of drug and linker conjugation to the antibody (Polakis, P. (2005) Current Opinion in Pharmacology 5:382-387).

KADCYLA® (trastuzumab emtansine, Genentech) has recently been approved for the treatment of breast cancer. Trastuzumab emtansine is an antibody-drug conjugate with a maytansine drug moiety DM1 covalently attached via a stable, non-disulfide linker MCC to the anti-HER2 antibody trastuzumab (Phillips G. et al. (2008) Cancer Res. 68:9280-90). Trastuzumab is the antibody formulated as HERCEPTIN® (Genentech), approved in 1998 for HER2 positive breast cancer therapy.

Anthracyclines are used in the treatment of numerous cancers such as leukemia, breast carcinoma, lung carcinoma, ovarian adenocarcinoma and sarcomas. Commonly used anthracyclines include doxorubicin, epirubicin, idarubicin and daunomycin. Morpholino analogs of doxorubicin and daunorubicin, formed by cyclization on the glycoside amino group, have greater potency (Acton et al (1984) J. Med. Chem. 638-645; U.S. Pat. Nos. 4,464,529; 4,672,057; 5,304,687). Nemorubicin is a semisynthetic analog of doxorubicin with a 2-methoxymorpholino group on the glycoside amino of doxorubicin and has been under clinical evaluation (Grandi et al (1990) Cancer Treat. Rew. 17:133; Ripamonti et al (1992) Brit. J. Cancer 65:703), including phase II/III trials for hepatocellular carcinoma (Sun et al (2003) Proceedings of the American Society for Clinical Oncology 22, Abs1448; Quintieri (2003) Proceedings of the American Association of Cancer Research, 44:1st Ed, Abs 4649; Pacciarini et al (2006) Jour. Clin. Oncology 24:14116). Immunoconjugates and prodrugs of daunorubicin and doxorubicin have been prepared and studied (Kratz et al (2006) Current Med. Chem. 13:477-523; Jeffrey et al (2006) Bioorganic & Med. Chem. Letters 16:358-362; Torgov et al (2005) Bioconj. Chem. 16:717-721; Nagy et al (2000) Proc. Natl. Acad. Sci. 97:829-834; Dubowchik et al (2002) Bioorg. & Med. Chem. Letters 12:1529-1532; King et al (2002) J. Med. Chem. 45:4336-4343; U.S. Pat. No. 6,630,579). The antibody-drug conjugate BR96-doxorubicin reacts specifically with the tumor-associated antigen Lewis-Y and has been evaluated in phase I and II studies (Saleh et al (2000) J. Clin. Oncology 18:2282-2292; Ajani et al (2000) Cancer Jour. 6:78-81; Tolcher et al (1999) J. Clin. Oncology 17:478-484).

Several metabolites of nemorubicin (MMDX) from liver microsomes have been characterized, including PNU-159682, (Quintieri et al (2005) Clinical Cancer Research, 11(4):1608-1617; Beulz-Riche et al (2001) Fundamental & Clinical Pharmacology, 15(6):373-378; EP 0889898; WO 2004/082689; WO 2004/082579). PNU-159682 was remarkably more cytotoxic than nemorubicin and doxorubicin in vitro, and was effective in vivo tumor models. PNU-159682 is named as 3'-deamino-3",4'-anhydro-[2"(S)-methoxy-3"(R)-oxy-4"-morpholinyl]doxorubicin, and has the structure:

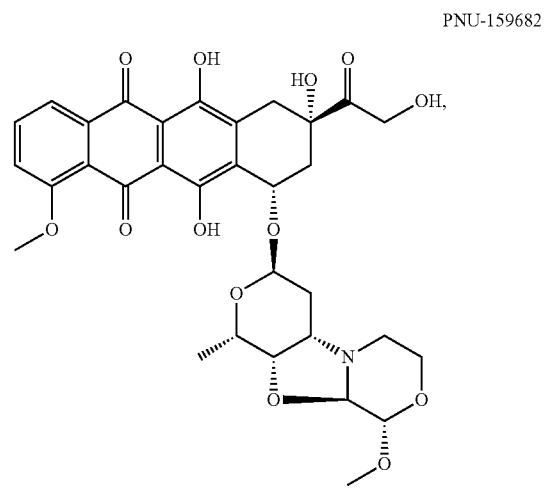 [SMILES: COc1cccc2c1C(=O)c1c(O)c3c(c(O)c1C2=O)C[C@@](O)(C(=O)CO)C[C@@H]3O[C@H]1C[C@H]2[C@H](O[C@@H]3[C@@H](OC)OCCN32)[C@H](C)O1]

PNU-159682

Certain PNU-159682 antibody-drug conjugates have been described (WO 2009/099741; WO 2010/009124; U.S. Pat. Nos. 8,742,076; 8,389,697). Processes for making PNU-159682 analogs are described (U.S. Pat. No. 8,470,984).

SUMMARY

The invention includes anthracycline disulfide intermediates having Formula I:

$$\text{Ant-L-}(Z)_m\text{—X} \qquad \text{I}$$

wherein Ant is selected from the structure:

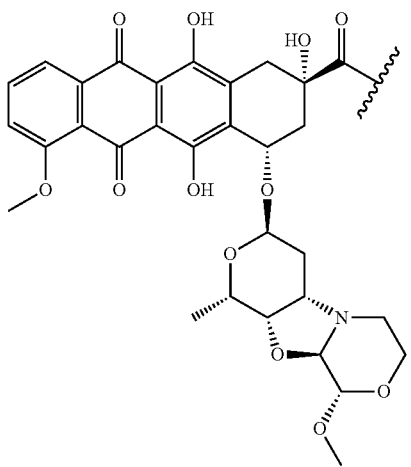 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

where the wavy line indicates the attachment to L;

L is a linker selected from —CH$_2$O—, —CH$_2$N(R)—, —N(R)—, —N(R)(C$_1$-C$_{12}$ alkylene)-, —N(R)(C$_2$-C$_8$ alkenylene)-, —N(R)(C$_2$-C$_8$ alkynylene)-, —N(R)(CH$_2$CH$_2$O)$_n$—, and the structure:

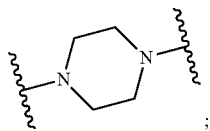 [SMILES: *N1CCN(*)CC1]

where the wavy lines indicate the attachments to Ant and Z; and

Z is an optional spacer selected from —CH$_2$C(O)—, —CH$_2$C(O)NR(C$_1$-C$_{12}$ alkylene)-, and the structure:

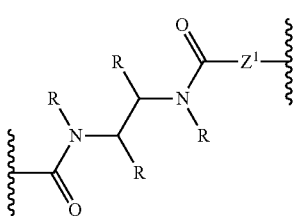

where the wavy lines indicate the attachments to L and X;

R is H, C$_1$-C$_{12}$ alkyl, or C$_6$-C$_{20}$ aryl;

Z$^1$ is selected from —(C$_1$-C$_{12}$ alkylene), —(C$_2$-C$_8$ alkenylene)-, —(C$_2$-C$_8$ alkynylene)-, —O(C$_1$-C$_{12}$ alkylene)-, —O(C$_2$-C$_8$ alkenylene)-, —O(C$_2$-C$_8$ alkynylene)-, and —(CH$_2$CH$_2$O)$_n$—;

m is 0 or 1;

n is 1 to 6;

X is pyridyl disulfide where pyridyl is optionally substituted with one or more groups selected from NO$_2$, Cl, F, and Br; and alkylene, alkenylene, alkynylene, alkyl, and aryl are optionally substituted with one or more groups selected from F, Cl, Br, N(CH$_3$)$_2$, and OCH$_3$.

The invention includes anthracycline disulfide intermediates covalently attached to antibodies to form antibody-drug conjugate (ADC) compounds with therapeutic or diagnostic applications.

Another aspect of the invention is an antibody-drug conjugate compound comprising an antibody covalently attached by a disulfide, linker L and an optional spacer Z to one or more anthracycline derivative drug moieties D, the compound having Formula II:

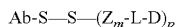

$$Ab-S-S-(Z_m-L-D)_p \qquad \text{II}$$

or a pharmaceutically acceptable salt thereof, wherein:

Ab is an antibody which binds to one or more tumor-associated antigens or cell-surface receptors selected from (1)-(53):

(1) BMPR1B (bone morphogenetic protein receptor-type IB);

(2) E16 (LAT1, SLC7A5);

(3) STEAP1 (six transmembrane epithelial antigen of prostate);

(4) MUC16 (0772P, CA125);

(5) MPF (MPF, MSLN, SMR, megakaryocyte potentiating factor, mesothelin);

(6) Napi2b (NAPI-3B, NPTIIb, SLC34A2, solute carrier family 34 (sodium phosphate), member 2, type II sodium-dependent phosphate transporter 3b);

(7) Sema 5b (FLJ0372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008O16Rik, RIKEN cDNA 2700050C12, RIKEN cDNA 2700050C12 gene);

(9) ETBR (Endothelin type B receptor);

(10) MSG783 (RNF124, hypothetical protein F1120315);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);

(12) TrpM4 (BR22450, FLJ20041, TRPM4, TRPM4B, transient receptor potential cation channel, subfamily M, member 4);

(13) CRIPTO (CR, CR1, CRGF, CRIPTO, TDGF1, teratocarcinoma-derived growth factor);

(14) CD21 (CR2 (Complement receptor 2) or C3DR (C3d/Epstein Barr virus receptor) or Hs 73792);

(15) CD79b (CD79B, CD7913, IGb (immunoglobulin-associated beta), B29);

(16) FcRH2 (IFGP4, IRTA4, SPAP1A (SH2 domain containing phosphatase anchor protein 1a), SPAP1B, SPAP1C);

(17) HER2;

(18) NCA;

(19) MDP;

(20) IL20Rα;

(21) Brevican;

(22) EphB2R;

(23) ASLG659;

(24) PSCA;

(25) GEDA;

(26) BAFF-R (B cell-activating factor receptor, BLyS receptor 3, BR3);

(27) CD22 (B-cell receptor CD22-B isoform);

(28) CD79a (CD79A, CD79α, immunoglobulin-associated alpha);

(29) CXCR5 (Burkitt's lymphoma receptor 1);

(30) HLA-DOB (Beta subunit of MEW class II molecule (Ia antigen));

(31) P2X5 (Purinergic receptor P2X ligand-gated ion channel 5);

(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) FcRH5 (IRTA2, Immunoglobulin superfamily receptor translocation associated 2);
(36) TENB2 (putative transmembrane proteoglycan);
(37) PMEL17 (silver homolog; SILV; D12S53E; PMEL17; SI; SIL);
(38) TMEFF1 (transmembrane protein with EGF-like and two follistatin-like domains 1; Tomoregulin-1);
(39) GDNF-Ra1 (GDNF family receptor alpha1; GFRA1; GDNFR; GDNFRA; RETL1; TRNR1; RET1L; GDNFR-alpha1; GFR-ALPHA-1);
(40) Ly6E (lymphocyte antigen 6 complex, locus E; Ly67, RIG-E, SCA-2, TSA-1);
(41) TMEM46 (shisa homolog 2 (*Xenopus laevis*); SHISA2);
(42) Ly6G6D (lymphocyte antigen 6 complex, locus G61); Ly6-D, MEGT1);
(43) LGR5 (leucine-rich repeat-containing G protein-coupled receptor 5; GPR49, GPR67);
(44) RET (ret proto-oncogene; MEN2A; HSCR1; MEN2B; MTC1; PTC; CDHF12; Hs.168114; RET51; RET-ELE1);
(45) LY6K (lymphocyte antigen 6 complex, locus K; LY6K; HSJ001348; FLJ35226);
(46) GPR19 (G protein-coupled receptor 19; Mm.4787);
(47) GPR54 (KISS1 receptor; KISS1R; GPR54; HOT7T175; AXOR12);
(48) ASPHD1 (aspartate beta-hydroxylase domain containing 1; LOC253982);
(49) Tyrosinase (TYR; OCAIA; OCA1A; tyrosinase; SHEP3);
(50) TMEM118 (ring finger protein, transmembrane 2; RNFT2; FLJ14627);
(51) GPR172A (G protein-coupled receptor 172A; GPCR41; FLJ11856; D15Ertd747e);
(52) CD33; and
(53) CLL-1;

D is an anthracycline derivative selected from the structure:

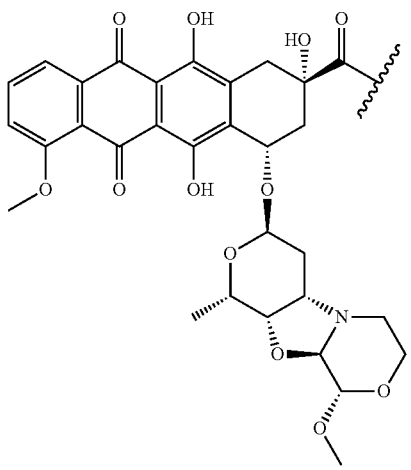 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

where the wavy line indicates the attachment to L;
L is a linker selected from —CH$_2$O—, —CH$_2$N(R)—, —N(R)—, —N(R)(C$_1$-C$_{12}$ alkylene)-, —N(R)(C$_2$-C$_8$ alkenylene)-, —N(R)(C$_2$-C$_8$ alkynylene)-, —N(R)(CH$_2$CH$_2$O)$_n$—, and the structure:

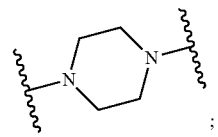 [SMILES: *N1CCN(*)CC1]

where the wavy lines indicate the attachments to D and Z; and
Z is an optional spacer selected from —CH$_2$C(O)—, —CH$_2$C(O)NR(C$_1$-C$_{12}$ alkylene)-, and the structures:

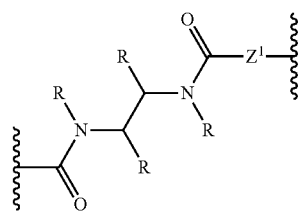

R is H, C$_1$-C$_{12}$ alkyl, or C$_6$-C$_{20}$ aryl;
Z$^1$ is selected from —(C$_1$-C$_{12}$ alkylene)-, —(C$_2$-C$_8$ alkenylene)-, —(C$_2$-C$_8$ alkynylene)-, and —(CH$_2$CH$_2$O)$_n$—,
m is 0 or 1;
n is 1 to 6;
p is an integer from 1 to 8; and
alkylene, alkenylene, alkynylene, alkyl, and aryl are optionally substituted with one or more groups selected from F, Cl, Br, N(CH$_3$)$_2$, NO$_2$, and OCH$_3$.

Another aspect of the invention is a pharmaceutical composition comprising an antibody-drug conjugate compound of Formula II, and a pharmaceutically acceptable diluent, carrier or excipient.

Another aspect of the invention is the use of an antibody-drug conjugate compound of Formula II in the manufacture of a medicament for the treatment of cancer in a mammal.

Another aspect of the invention is a method of treating cancer by administering to a patient a pharmaceutical composition comprising an antibody-drug conjugate compound of Formula II.

Another aspect of the invention is a method of making an antibody-drug conjugate compound of Formula II.

Another aspect of the invention is an article of manufacture comprising a pharmaceutical composition comprising an antibody-drug conjugate compound of Formula II, a container, and a package insert or label indicating that the pharmaceutical composition can be used to treat cancer.

DETAILED DESCRIPTION OF EXEMPLARY EMBODIMENTS

Figure 1:
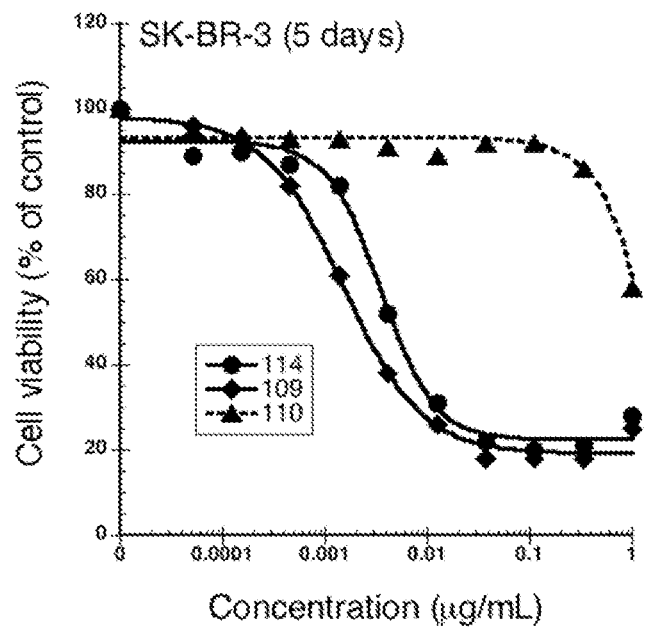
FIG. 1 shows the efficacy of antibody-drug conjugates in a plot of SK-BR-3 in vitro cell viability at 5 days versus concentrations (μg/ml) of Thio Hu anti-Her2 7C2 HC A118C-(LD-57) 114, Thio Hu anti-Her2 7C2 LC K149C-(LD-57) 109, and Thio Hu anti-CD33 15G15.3 LC K149C-(LD-57) 110.

Reference will now be made in detail to certain embodiments of the invention, examples of which are illustrated in the accompanying structures and formulas. While the invention will be described in conjunction with the illustrated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Definitions

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "antibody" herein is used in the broadest sense and specifically covers monoclonal antibodies, polyclonal antibodies, dimers, multimers, multi specific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature, 256:495, or may be made by recombinant DNA methods (see for example: U.S. Pat. Nos. 4,816,567; 5,807,715). Monoclonal antibodies may also be isolated from phage antibody libraries using the techniques described in Clackson et al (1991) Nature, 352:624-628; Marks et al (1991) J. Mol. Biol., 222:581-597.

Monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267: 7246-7256; US 2005/0048572; US 2004/0229310).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "free cysteine amino acid" refers to a cysteine amino acid residue which has been engineered into a parent antibody, has a thiol functional group (—SH), and is not paired as an intramolecular or intermolecular disulfide bridge.

"Linker", "Linker Unit", or "link" means a chemical moiety comprising a chain of atoms that covalently attaches an antibody to a drug moiety. In various embodiments, a linker is a divalent radical, specified as L.

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), n-propylene (—$CH_2CH_2CH_2$—), i-propylene (—CH($CH_3$)$CH_2$—), i-butylene (—C($CH_3$)$_2CH_2$—) and the like.

The term "alkenyl" refers to linear or branched-chain monovalent hydrocarbon radical of any length from two to eight carbon atoms ($C_2$-$C_8$) with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), crotyl (—CH($CH_3$)CH=$CH_2$), and the like.

The term "alkenylene" refers to linear or branched-chain divalent hydrocarbon radical of any length from two to eight carbon atoms ($C_2$-$C_8$) with at least one site of unsaturation, i.e., a carbon-carbon, sp$^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH=CH—), allylene (—CH$_2$CH=CH—), crotylene (—CH(CH$_3$)CH=CH—), and the like.

The term "alkynyl" refers to a linear or branched monovalent hydrocarbon radical of any length from two to eight carbon atoms (C$_2$-C$_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "alkynylene" refers to a linear or branched divalent hydrocarbon radical of any length from two to eight carbon atoms (C$_2$-C$_8$) with at least one site of unsaturation, i.e., a carbon-carbon, sp triple bond, wherein the alkynylene radical may be optionally substituted independently with one or more substituents described herein. Examples include, but are not limited to, ethynylene propynylene (propargylene, —CH$_2$C≡C—), 2-butynylene (—CH(CH$_3$)C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms (C$_3$-C$_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms (C$_6$-C$_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms (C$_6$-C$_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or (3-carboline.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an antibody-drug conjugate (ADC). Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The following abbreviations are used herein and have the indicated definitions: BME is beta-mercaptoethanol, Boc is N-(t-butoxycarbonyl), cit is citrulline (2-amino-5-ureido pentanoic acid), DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, MeOH is methanol, Mtr is 4-anisyldiphenylmethyl (or 4-methoxytrityl), NHS is N-hydroxysuccinimide, PBS is phosphate-buffered saline (pH 7), PEG is polyethylene glycol or a unit of ethylene glycol (—$OCH_2CH_2$—), Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Cysteine Engineered Antibodies

The compounds of the invention include antibody-drug conjugates comprising cysteine engineered antibodies where one or more amino acids of a wild-type or parent antibody are replaced with a cysteine amino acid (THIOMAB™). Any form of antibody may be so engineered, i.e. mutated. For example, a parent Fab antibody fragment may be engineered to form a cysteine engineered Fab. Similarly, a parent monoclonal antibody may be engineered to form a THIOMAB™. It should be noted that a single site mutation yields a single engineered cysteine residue in a Fab antibody fragment, while a single site mutation yields two engineered cysteine residues in a full length THIOMAB™, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

Cysteine amino acids may be engineered at reactive sites in the heavy chain (HC) or light chain (LC) of an antibody and which do not form intrachain or intermolecular disulfide linkages (Junutula, et al., 2008b Nature Biotech., 26(8):925-932; Dornan et al (2009) Blood 114(13):2721-2729; U.S. Pat. Nos. 7,521,541; 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the linker-drug intermediates of the present invention which have thiol-reactive, electrophilic pyridyl disulfide groups to form ADC with cysteine engineered antibodies (THIOMAB™) and the drug (D) moiety. The location of the drug moiety can thus be designed, controlled, and known. The drug loading can be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A drug loading near 2 can be achieved and near homogeneity of the conjugation product ADC.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

Cysteine engineered antibodies are prepared for conjugation with linker-drug intermediates by reduction and reoxidation of intrachain disulfide groups (Example 19).

Cysteine engineered antibodies which may be useful in the antibody-drug conjugates of the invention in the treatment of cancer include, but are not limited to, antibodies against cell surface receptors and tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(51) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 4:
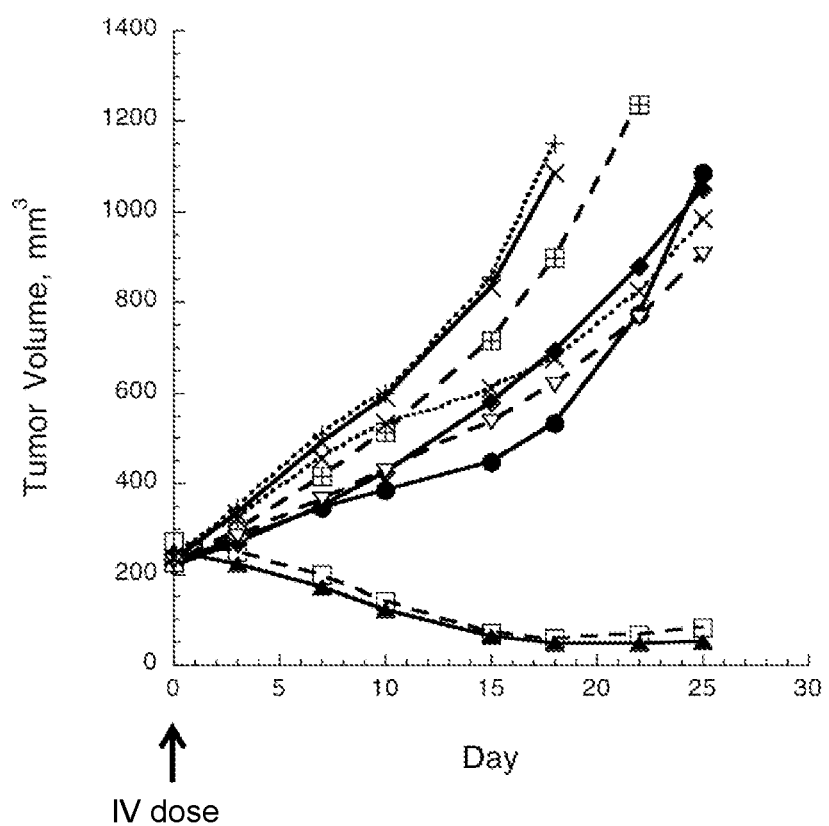
FIG. 4 shows the efficacy of antibody-drug conjugates in a plot of the in vivo fitted tumor volume change over time in KPL4 tumor model in scid beige mice inoculated in the thoracic mammary fat pad at a volume of 0.2 ml. When tumors reached a mean tumor volume of 100-250 mm3, they were grouped into 9 groups of 8-10 mice each. A single treatment was administered intravenously via the tail vein on Day 0 as follows: (01) Vehicle: Histidine Buffer #8: 20 mM Histidine Acetate, pH 5.5, 240 mM Sucrose, 0.02% PS 20, (02) Thio Hu anti-Her2 7C2 LC K149C-(ethylmaleimide) 0.3 mg/kg 138, (03) Thio Hu anti-Her2 7C2 LC K149C-(ethylmaleimide) 1 mg/kg 138, (04) Thio Hu anti-Her2 7C2 LC K149C-(ethylmaleimide) 3 mg/kg 138, (05) Thio Hu anti-Her2 7C2 LC K149C-(LD-57) 0.3 mg/kg 109, (06) Thio Hu anti-Her2 7C2 LC K149C-(LD-57) 1 mg/kg 109, (07) Thio Hu anti-Her2 7C2 LC K149C-(LD-57) 3 mg/kg 109, (08) Thio Hu Anti-CD33 15G15.3 LC K149C-(ethylmaleimide) 3 mg/kg 139, and (09) Thio Hu anti-CD33 15G15.3 LC K149C-(LD-57) 3 mg/kg 110.

Tumor-Associated Antigens:

(1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377 (Page 349-350); WO200230268 (claim 27; Page 376); WO200148204 (Example; FIG. 4) NP_001194 bone morphogenetic protein receptor, type IB/pid=NP_001194.1—Cross-references: MIM:603248; NP_001194.1; AY065994

Figure 3:
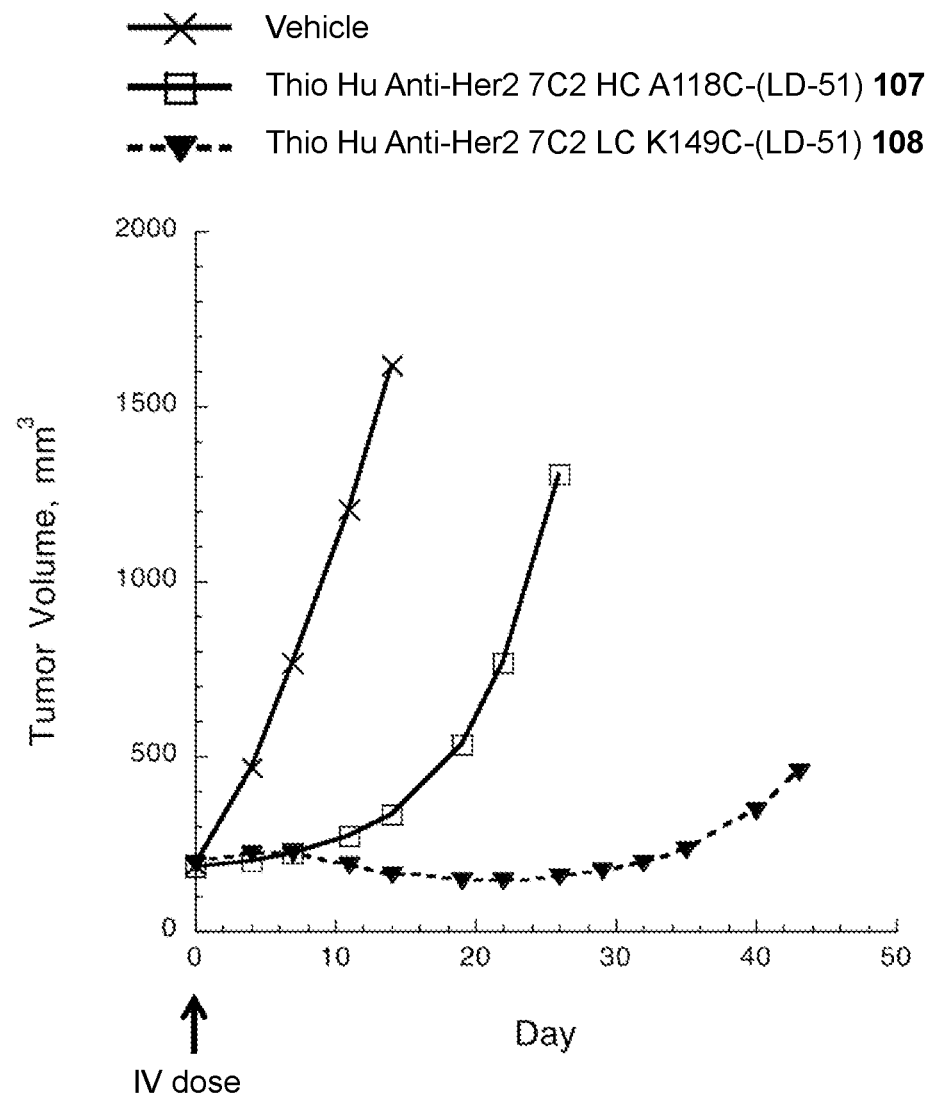
FIG. 3 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: Vehicle: Histidine Buffer #8: 20 mM Histidine Acetate, pH 5.5, 240 mM Sucrose, 0.02% PS 20, Thio Hu Anti-Her2 7C2 HC A118C-(LD-51) 107, and Thio Hu Anti-Her2 7C2 LC K149C-(LD-51) 108. ADC were dosed at 3 mg/kg one time IV at day 0.

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150); NP_003477 solute carrier family 7 (cationic amino acid transporter, y+ system), member 5/pid=NP_003477.3 —Homo sapiens Cross-references: MIM:600182; NP_003477.3; NM_015923; NM_003486_1

Figure 2:
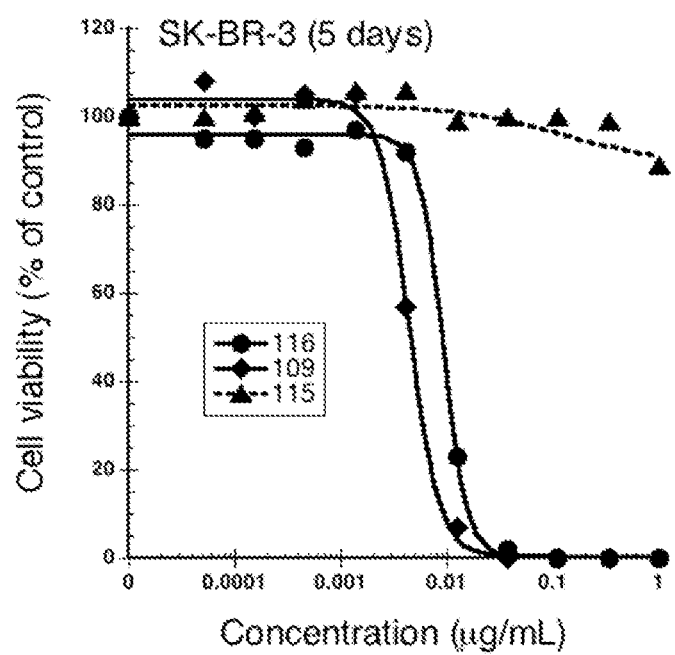
FIG. 2 shows the efficacy of antibody-drug conjugates in a plot of SK-BR-3 in vitro cell viability at 5 days versus concentrations (μg/ml) of Thio Hu anti-Her2 7C2 LC K149C-(LD-59) 116, Thio Hu anti-Her2 7C2 LC K149C-(LD-57) 109, and Thio Hu Anti-CD33 15G15.3 LC K149C-(LD-59) 115.

(3) STEAP1 (six transmembrane epithelial antigen of prostate, Genbank accession no. NM_012449) Cancer Res. 61 (15), 5857-5860 (2001), Hubert, R. S., et al (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM:604415; NP_036581.1; NM_012449_1

(4) 0772P (CA125, MUC16, Genbank accession no. AF361486) J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); U.S. Pat. No. 798,959. Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57); Cross-references: MIM:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140); Cross-references: MIM: 604217; NP_006415.1; NM_006424_1

(7) Sema 5b (F1110372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11); Accession: Q9P283; EMBL; AB040878; BAA95969.1. Genew; HGNC:10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1

Figure 6:
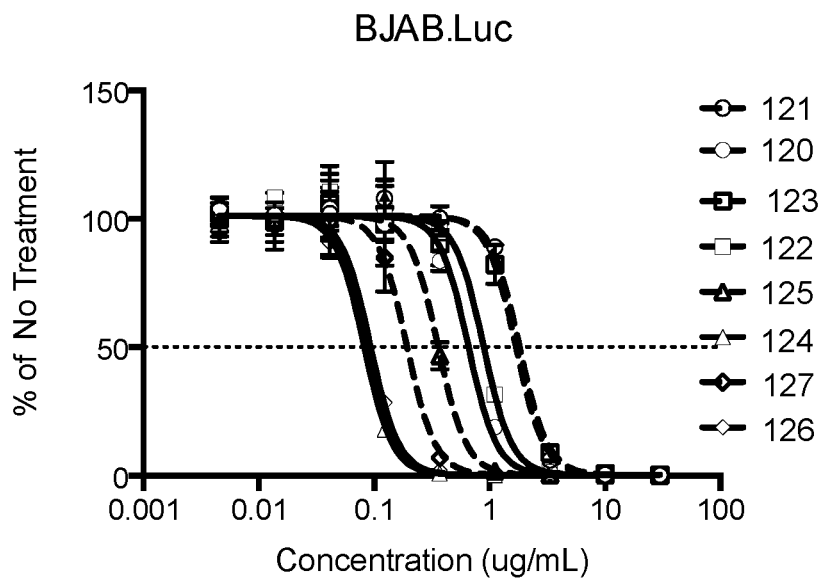
FIG. 6 shows the efficacy of antibody-drug conjugates in a plot of BJAB.luc in vitro cell viability at 5 days versus concentrations (μg/ml) of Thio Hu Anti-Napi3b 10H1.11.4B LC K149C-(LD-57) 121, Thio Hu anti-CD22 10F4v3 LC K149C-(LD-57) 120, Thio Hu Anti-Napi3b 10H1.11.4B LC K149C-(LD-59) 123, Thio Hu anti-CD22 10F4v3 LC K149C-(LD-59) 122, Thio Hu Anti-Napi3b 10H1.11.4B LC K149C-(LD-58) 125, Thio Hu anti-CD22 10F4v3 LC K149C-(LD-58) 124, Thio Hu Anti-Napi3b 10H1.11.4B LC K149C-(LD-60) 127, and Thio Hu anti-CD22 10F4v3 LC K149C-(LD-60) 126.

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein F1120315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6); Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636) Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212) Ciccodicola, A., et al EMBO J. 8 (7):1987-1991 (1989), Am. J. Hum. Genet. 49 (3): 555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2); Cross-references: MIM: 187395; NP_003203.1; NM_003212_1

(14) CD21 (CR2 (Complement receptor 2) or C3DR (C3d/Epstein Barr virus receptor) or Hs.73792 Genbank accession no. M26004) Fujisaku et al (1989) J. Biol. Chem. 264

(4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (claim 9); WO2004045520 (Example 4); WO9102536 (FIGS. 9.1-9.9); WO2004020595 (claim 1); Accession: P20023; Q13866; Q14212; EMBL; M26004; AAA35786.1.

(15) CD79b (CD79B, CD7913, IGb (immunoglobulin-associated beta), B29, Genbank accession no. NM_000626 or 11038674) Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (claim 2); WO2003077836; WO200138490 (claim 5; FIG. 18D-1-18D-2); WO2003097803 (claim 12); WO2003089624 (claim 25); Cross-references: MIM:606509; NP_110391.2; NM_030764_1

Figure 7:
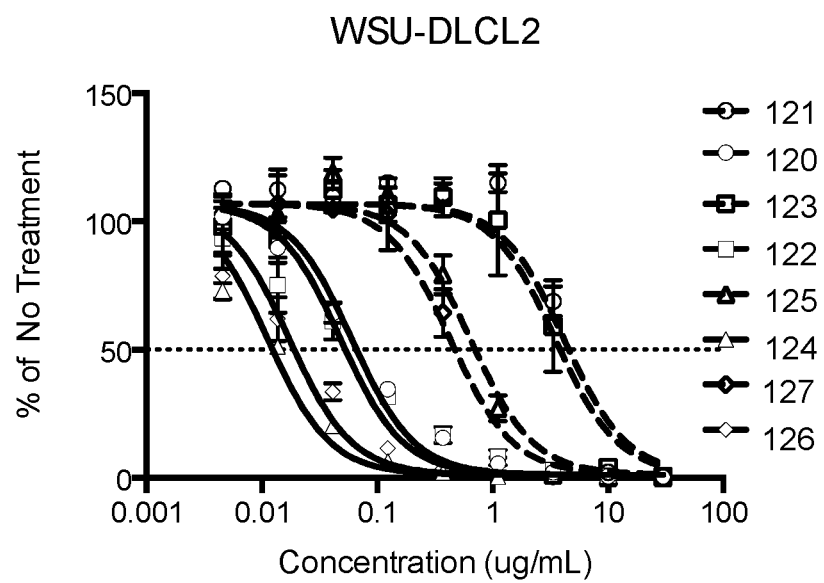
FIG. 7 shows the efficacy of antibody-drug conjugates in a plot of WSU-DLCL2 in vitro cell viability at 5 days versus concentrations (μg/ml) of Thio Hu Anti-Napi3b 10H1.11.4B LC K149C-(LD-57) 121, Thio Hu anti-CD22 10F4v3 LC K149C-(LD-57) 120, Thio Hu Anti-Napi3b 10H1.11.4B LC K149C-(LD-59) 123, Thio Hu anti-CD22 10F4v3 LC K149C-(LD-59) 122, Thio Hu Anti-Napi3b 10H1.11.4B LC K149C-(LD-58) 125, Thio Hu anti-CD22 10F4v3 LC K149C-(LD-58) 124, Thio Hu Anti-Napi3b 10H1.11.4B LC K149C-(LD-60) 127, and Thio Hu anti-CD22 10F4v3 LC K149C-(LD-60) 126.

(17) HER2 (ErbB2, Genbank accession no. M11730) Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2); Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (claim 1); WO200264798 (claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42); Cross-references: MIM:600997; NP_004433.2; NM_004442_1

(23) ASLG659 (B7h, Genbank accession no. AX092328) US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIG. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318;

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709;

EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B); Accession: 043653; EMBL; AF043498; AAC39607.1.

(25) GEDA (Genbank accession No. AY260763); AAP14954 lipoma HMGIC fusion-partner-like protein/ pid=AAP14954.1 —*Homo sapiens* Species: *Homo sapiens* (human) WO2003054152 (claim 20); WO2003000842 (claim 1); WO2003023013 (Example 3, claim 20); US2003194704 (claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1 —*Homo sapiens* Thompson, J. S., et al Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) J. Exp. Med. 173: 137-146; WO2003072036 (claim 1; FIG. 1); Cross-references: MIM:107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1) WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+ T lymphocytes); 273 aa, pI: 6.56 MW: 30820 TM: 1 [P] Gene Chromosome: 6p21.3, Genbank accession No. NP_002111.1) Tonnelle et al (1985) EMBO J. 4(11): 2839-2847; Jonsson et al (1989) Immunogenetics 29(6): 411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2) Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity (SEQ ID NO: 29) . . . tafrfpd (SEQ ID NO: 30) (1 . . . 359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human:AF343662, AF343663, AF343664, AF343665, AF369794, AF397453, AK090423, AK090475, AL834187, AY358085; Mouse: AK089756, AY158090, AY506558; NP_112571.1 WO2003024392 (claim 2, FIG. 97); Nakayama et al (2000) Biochem. Biophys. Res.

Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84;

(37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E; Ly67, RIG-E, SCA-2, TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;

(41) TMEM46 (shisa homolog 2 (*Xenopus laevis*); SHISA2); NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1); NP_067079.2; NM_021246.2; Mallya M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KiSS1 receptor; KISS1R; GPR54; HOT7T175; AXOR12); NP_115940.2; NM_032551.4; Navenot, J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing; LOC253982); NP_859069.2; NM_181718.3; Gerhard, D. S. et al (2004) Genome Res. 14 (10B):2121-2127;

(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A; GPCR41; FLJ11856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

Anti-CD22 Antibodies

The anti-CD22 antibodies of ADC in Table 3 comprise three light chain hypervariable regions (HVR-L1, HVR-L2 and HVR-L3) and three heavy chain hypervariable regions (HVR-H1, HVR-H2 and HVR-H3), according to U.S. Pat. No. 8,226,945:

HVR-L1
(SEQ ID NO: 1)
RSSQSIVHSVGNTFLE

HVR-L2
(SEQ ID NO: 2)
KVSNRFS

HVR-L3
(SEQ ID NO: 3)
FQGSQFPYT

HVR-H1
(SEQ ID NO: 4)
GYEFSRSWMN

HVR-H2
(SEQ ID NO: 5)
GRIYPGDGDTNYSGKFKG

HVR-H3
(SEQ ID NO: 6)
DGSSWDWYFDV

Anti-HER2 Antibodies

In certain embodiments, ADC of Table 3 comprise anti-HER2 antibodies. In one embodiment of the invention, an anti-HER2 antibody of an ADC of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337, which is specifically incorporated by reference herein. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN®. In another embodiment of the invention, an anti-HER2 antibody of an ADC of the invention comprises a humanized anti-HER2 antibody, e.g., humanized 2C4, as described in U.S. Pat. No. 7,862,817. An exemplary humanized 2C4 antibody is pertuzumab, commercially available under the tradename PERJETA®.

In another embodiment of the invention, an anti-HER2 antibody of an ADC of the invention comprises a humanized anti-HER2 antibody is 7C2.

In some embodiments, cysteine-engineered THIOMAB™ antibodies used to prepare the ADC of Table 3 have a cysteine residue introduced at the 149-lysine site of the light chain (LC K149C). In other embodiments, the cysteine-engineered THIOMAB™ antibodies have a cysteine residue introduced at the 118-alanine site (EU numbering) of the heavy chain (HC A118C). This site is alternatively numbered 121 by Sequential numbering or 114 by Kabat numbering.

Anti-CD33 Antibodies

The anti-CD33 antibody 15G15.33 of ADC in Table 2 comprises three light chain hypervariable regions (HVR-L1, HVR-L2 and HVR-L3) and three heavy chain hypervariable regions (HVR-H1, HVR-H2 and HVR-H3)

HVR-L1
(SEQ ID NO: 7)
RSSQSLLHSNGYNYLD

HVR-L2
(SEQ ID NO: 8)
LGVNSVS

HVR-L3
(SEQ ID NO: 9)
MQALQTPWT

HVR-H1
(SEQ ID NO: 10)
NHAIS

HVR-H2
(SEQ ID NO: 11)
GIIPIFGTANYAQKFQG

HVR-H3
(SEQ ID NO: 12)
EWADVFD

The anti-CD33 antibody 15G15.33 of ADC in Table 5 comprises the light chain variable region of SEQ ID NO:13 and/or the heavy chain variable region of SEQ ID NO:14.

(SEQ ID NO: 13)
EIVLTQSPLSLPVTPGEPASISCRSSQSLLHSNGYNYLDWYLQKPGQSP
QLLIYLGVNSVSGVPDRFSGSGSGTDFTLKISRVEAEDVGVYYCMQALQ
TPWTFGQGTKVEIK (SEQ ID NO: 14)
QVQLVQSGAEVKKPGSSVKVSCKASGGIFSNHAISWVRQAPGQGLEWMG
GIIPIFGTANYAQKFQGRVTITADESTSTAFMELSSLRSEDTAVYYCAR
EWADVFDIWGQGTMVTVSS

Anti-CD33 Antibody 9C3 and Other Embodiments

9C3-HVR L1
(SEQ ID NO: 15)
RASQGIRNDLG

9C3-HVR L2
(SEQ ID NO: 16)
AASSLQS

9C3-HVR L3
(SEQ ID NO: 17)
LQHNSYPWT

9C3-HVR H1
(SEQ ID NO: 18)
GNYMS

9C3-HVR H2
(SEQ ID NO: 19)
LIYSGDSTYYADSVKG

9C3-HVR H3
(SEQ ID NO: 20)
DGYYVSDMVV

9C3 $V_L$
(SEQ ID NO: 21)
DIQMTQSPSSLSASVGDRVTITCRASQGIRNDLGWYQQKPGKAPKRLIY
AASSLQSGVPSRFSGSGSGTEFTLTISSLQPEDFATYYCLQHNSYPWTF
GQGTKLEIK

-continued

9C3 V$_H$
(SEQ ID NO: 22)
EVQLVESGGALIQPGGSLRLSCVASGFTISGNYMSWVRQAPGKGLEWVS

LIYSGDSTYYADSVKGRFNISRDISKNTVYLQMNSLRVEDTAVYYCVRD

GYYVSDMVVWGKGTTVTVSS

9C3.2 V$_L$
(SEQ ID NO: 23)
DIQMTQSPSSLSASVGDRVTITCRASQGIRNDLGWYQQKPGKAPKRLIY

AASSLQSGVPSRFSGSGSGTEFTLTISSLQPEDFATYYCLQHNSYPWTF

GQGTKLEIK

9C3.2 V$_H$
(SEQ ID NO: 24)
EVQLVESGGALIQPGGSLRLSCVASGFTISGNYMSWVRQAPGKGLEWVS

LIYSGDSTYYADSVKGRFTISRDISKNTVYLQMNSLRVEDTAVYYCVRD

GYYVSDMVVWGKGTTVTVSS

9C3.3 V$_L$
(SEQ ID NO: 25)
DIQMTQSPSSLSASVGDRVTITCRASQGIRNDLGWYQQKPGKAPKRLIY

AASSLQSGVPSRFSGSGSGTEFTLTISSLQPEDFATYYCLQHNSYPWTF

GQGTKLEIK

9C3.3 V$_H$
(SEQ ID NO: 26)
EVQLVESGGALIQPGGSLRLSCVASGFTISGNYMSWVRQAPGKGLEWVS

LIYSGDSTYYADSVKGRFSISRDISKNTVYLQMNSLRVEDTAVYYCVRD

GYYVSDMVVWGKGTTVTVSS

9C3.4 V$_L$
(SEQ ID NO: 27)
DIQMTQSPSSLSASVGDRVTITCRASQGIRNDLGWYQQKPGKAPKRLIY

AASSLQSGVPSRFSGSGSGTEFTLTISSLQPEDFATYYCLQHNSYPWTF

GQGTKLEIK

9C3.4 V$_H$
(SEQ ID NO: 28)
EVQLVESGGALIQPGGSLRLSCVASGFTISGNYMSWVRQAPGKGLEWVS

LIYSGDSTYYADSVKGRFAISRDISKNTVYLQMNSLRVEDTAVYYCVRD

GYYVSDMVVWGKGTTVTVSS

In some embodiments, the invention provides an anti-CD33 antibody comprising at least one, two, three, four, five, or six HVRs selected from (a) HVR-H1 comprising the amino acid sequence of SEQ ID NO:18; (b) HVR-H2 comprising the amino acid sequence of SEQ ID NO:19; (c) HVR-H3 comprising the amino acid sequence of SEQ ID NO:20; (d) HVR-L1 comprising the amino acid sequence of SEQ ID NO:15; (e) HVR-L2 comprising the amino acid sequence of SEQ ID NO:16; and (f) HVR-L3 comprising the amino acid sequence of SEQ ID NO:17.

In one aspect, the invention provides an antibody comprising at least one, at least two, or all three VH HVR sequences selected from (a) HVR-H1 comprising the amino acid sequence of SEQ ID NO:18; (b) HVR-H2 comprising the amino acid sequence of SEQ ID NO:19; and (c) HVR-H3 comprising the amino acid sequence of SEQ ID NO:20. In one embodiment, the antibody comprises HVR-H1 comprising the amino acid sequence of SEQ ID NO:20. In another embodiment, the antibody comprises HVR-H3 comprising the amino acid sequence of SEQ ID NO:20 and HVR-L3 comprising the amino acid sequence of SEQ ID NO:17. In a further embodiment, the antibody comprises HVR-H3 comprising the amino acid sequence of SEQ ID NO:20, HVR-L3 comprising the amino acid sequence of SEQ ID NO:17, and HVR-H2 comprising the amino acid sequence of SEQ ID NO:19. In a further embodiment, the antibody comprises (a) HVR-H1 comprising the amino acid sequence of SEQ ID NO:18; (b) HVR-H2 comprising the amino acid sequence of SEQ ID NO:19; and (c) HVR-H3 comprising the amino acid sequence of SEQ ID NO:20.

In another aspect, the invention provides an antibody comprising at least one, at least two, or all three VL HVR sequences selected from (a) HVR-L1 comprising the amino acid sequence of SEQ ID NO:15; (b) HVR-L2 comprising the amino acid sequence of SEQ ID NO:16; and (c) HVR-L3 comprising the amino acid sequence of SEQ ID NO:17. In one embodiment, the antibody comprises (a) HVR-L1 comprising the amino acid sequence of SEQ ID NO:15; (b) HVR-L2 comprising the amino acid sequence of SEQ ID NO:16; and (c) HVR-L3 comprising the amino acid sequence of SEQ ID NO:17.

In another aspect, an antibody of the invention comprises (a) a VH domain comprising at least one, at least two, or all three VH HVR sequences selected from (i) HVR-H1 comprising the amino acid sequence of SEQ ID NO:18, (ii) HVR-H2 comprising the amino acid sequence of SEQ ID NO:19, and (iii) HVR-H3 comprising an amino acid sequence selected from SEQ ID NO:20; and (b) a VL domain comprising at least one, at least two, or all three VL HVR sequences selected from (i) HVR-L1 comprising the amino acid sequence of SEQ ID NO:15, (ii) HVR-L2 comprising the amino acid sequence of SEQ ID NO:16, and (c) HVR-L3 comprising the amino acid sequence of SEQ ID NO:17.

In another aspect, the invention provides an antibody comprising (a) HVR-H1 comprising the amino acid sequence of SEQ ID NO:18; (b) HVR-H2 comprising the amino acid sequence of SEQ ID NO:19; (c) HVR-H3 comprising the amino acid sequence of SEQ ID NO:20; (d) HVR-L1 comprising the amino acid sequence of SEQ ID NO:15; (e) HVR-L2 comprising the amino acid sequence of SEQ ID NO:16; and (f) HVR-L3 comprising the amino acid sequence of SEQ ID NO:17.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus (VL$_{KI}$) framework and/or the VH framework VH$_1$. In certain embodiments, the human acceptor framework is the human VL kappa I consensus (VL$_{KI}$) framework and/or the VH framework VH$_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:22, SEQ ID NO:24, SEQ ID NO:26, and/or SEQ ID NO:28. In certain embodiments, a VH sequence having at least 90%, 91%, 92%, 93%, 94%, 95%, 96%, 97%, 98%, or 99% identity to the amino acid sequence of SEQ ID NO:22, SEQ ID NO:24, SEQ ID NO:26, and/or SEQ ID NO:28 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:22, SEQ ID NO:24, SEQ ID NO:26, and/or SEQ ID NO:28. In certain embodiments, a total of 1 to 5 amino acids have been substituted, inserted and/or deleted in SEQ ID NO:22, SEQ ID NO:24, SEQ ID NO:26, and/or SEQ ID NO:28. In certain embodiments, substitutions, insertions, or deletions occur in regions outside the HVRs (i.e., in the FRs). Optionally, the anti-CD33 antibody comprises the VH sequence of SEQ ID NO:22, SEQ ID NO:24, SEQ ID NO:26, and/or SEQ ID NO:28, including post-translational modifications of that sequence. In a particular embodiment, the VH comprises one, two or three HVRs selected from: (a) HVR-H1 comprising the amino acid sequence of SEQ ID NO:18, (b) HVR-H2 comprising the amino acid sequence of SEQ ID NO:19, and (c) HVR-H3 comprising the amino acid sequence of SEQ ID NO:20.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:21, SEQ ID NO:23, SEQ ID NO:25, and/or SEQ ID NO:27. In certain embodiments, a VL sequence having at least 90%, 91%, 92%, 93%, 94%, 95%, 96%, 97%, 98%, or 99% identity to the amino acid sequence of SEQ ID NO:21, SEQ ID NO:23, SEQ ID NO:25, and/or SEQ ID NO:27 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:21, SEQ ID NO:23, SEQ ID NO:25, and/or SEQ ID NO:27. In certain embodiments, a total of 1 to 5 amino acids have been substituted, inserted and/or deleted in SEQ ID NO:21, SEQ ID NO:23, SEQ ID NO:25, and/or SEQ ID NO:27. In certain embodiments, the substitutions, insertions, or deletions occur in regions outside the HVRs (i.e., in the FRs). Optionally, the anti-CD33 antibody comprises the VL sequence of SEQ ID NO:21, SEQ ID NO:23, SEQ ID NO:25, and/or SEQ ID NO:27, including post-translational modifications of that sequence. In a particular embodiment, the VL comprises one, two or three HVRs selected from (a) HVR-L1 comprising the amino acid sequence of SEQ ID NO:15; (b) HVR-L2 comprising the amino acid sequence of SEQ ID NO:16; and (c) HVR-L3 comprising the amino acid sequence of SEQ ID NO:17.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO:22 and SEQ ID NO:21, respectively, including post-translational modifications of those sequences. In one embodiment, the antibody comprises the VH and VL sequences in SEQ ID NO:24 and SEQ ID NO:23, respectively, including post-translational modifications of those sequences. In one embodiment, the antibody comprises the VH and VL sequences in SEQ ID NO:26 and SEQ ID NO:25, respectively, including post-translational modifications of those sequences. In one embodiment, the antibody comprises the VH and VL sequences in SEQ ID NO:28 and SEQ ID NO:27, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO:22, SEQ ID NO:24, SEQ ID NO:26, and/or SEQ ID NO:28 and a VL sequence of SEQ ID NO:21, SEQ ID NO:23, SEQ ID NO:25, and/or SEQ ID NO:27, respectively.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')2 fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

The parent antibody may also be a fusion protein comprising an albumin-binding peptide (ABP) sequence (Dennis et al. (2002) J Biol Chem. 277:35035-35043 (Tables III and IV, page 35038); and WO 2001/45746 at pages 12-13, which are incorporated herein by reference.

To prepare a cysteine engineered antibody by mutagenesis, DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Antibodies may be produced using recombinant methods and compositions, e.g., as described in U.S. Pat. No. 4,816,567. In one embodiment, isolated nucleic acid encodes an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method comprises culturing a host cell comprising a nucleic acid encoding the antibody, as provided above, under conditions suitable for expression of the antibody, and optionally recovering the antibody from the host cell (or host cell culture medium).

For recombinant production, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523, also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006). Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts, such as those described in U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Site-directed mutagenesis is one method for preparing substitution variants, i.e. mutant proteins (Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations (Liu et al (1998) J. Biol. Chem. 273:20252-20260). Site-directed mutagenesis protocols and formats are widely available, e.g. QuikChange® Multi Site-Directed Mutagenesis Kit (Stratagene, La Jolla, Calif.).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem., 5:126-132; and Vallette et al (1989) Nuc. Acids Res., 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene, 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability.

Anthracycline Disulfide Intermediates

An antibody-drug conjugate compound of the invention comprises an anthracycline disulfide intermediate comprised of a PNU-15682 moiety derivatized at the ketone group with a disulfide group.

The anthracycline disulfide intermediate has the formula:

$$\text{Ant-L-}(Z)_m\text{—X} \qquad \text{I}$$

wherein Ant is selected from the structure:

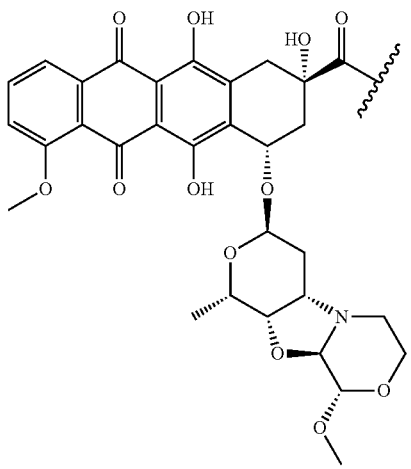 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

where the wavy line indicates the attachment to L;

L is a linker selected from —CH$_2$O—, —CH$_2$N(R)—, —N(R)—, —N(R)(C$_1$-C$_{12}$ alkylene)-, —N(R)(C$_2$-C$_8$ alkenylene)-, —N(R)(C$_2$-C$_8$ alkynylene)-, —N(R)(CH$_2$CH$_2$O)$_n$—, and the structure:

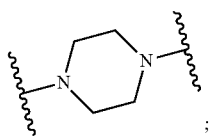 [SMILES: *N1CCN(*)CC1]

where the wavy lines indicate the attachments to Ant and Z; and

Z is an optional spacer selected from —CH$_2$C(O)—, —CH$_2$C(O)NR(C$_1$-C$_{12}$ alkylene)-, and the structure:

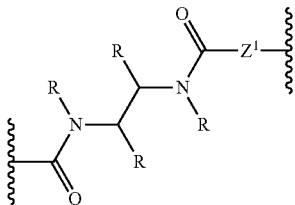

where the wavy lines indicate the attachments to L and X;

R is H, C$_1$-C$_{12}$ alkyl, or C$_6$-C$_{20}$ aryl;

Z$^1$ is selected from —(C$_1$-C$_{12}$ alkylene)-, —(C$_2$-C$_8$ alkenylene)-, —(C$_2$-C$_8$ alkynylene)-, —O(C$_1$-C$_{12}$ alkylene)-, —O(C$_2$-C$_8$ alkenylene)-, —O(C$_2$-C$_8$ alkynylene)-, and (CH$_2$CH$_2$O)$_n$—;

m is 0 or 1;

n is 1 to 6;

X is pyridyl disulfide where pyridyl is optionally substituted with one or more groups selected from NO$_2$, Cl, F, CN, and Br; and alkylene, alkenylene, alkynylene, alkyl, and aryl are optionally substituted with one or more groups selected from F, Cl, Br, N(CH$_3$)$_2$, NO$_2$, and OCH$_3$.

An exemplary embodiment of X is:

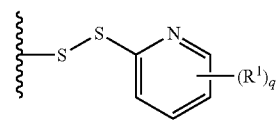

where the wavy lines indicate the attachments to L or Z;

R$^1$ is NO$_2$, Cl, F, CN or Br, and q is 0, 1, or 2.

Without being limited to a particular mechanism or effect, the presence of an electron-withdrawing group R$^1$; NO$_2$, Cl, F, or Br on the pyridyl ring of an anthracycline disulfide intermediate accelerates reaction with a cysteine thiol of a cysteine-engineered antibody. Where the cysteine thiol has been introduced at a hindered or less-reactive site on the antibody, such anthracycline disulfide intermediate give more efficient conjugation relative to a corresponding unsubstituted pyridyl analog (R$^1$=H).

Exemplary linker-drug intermediates are Formulas Ia-c:

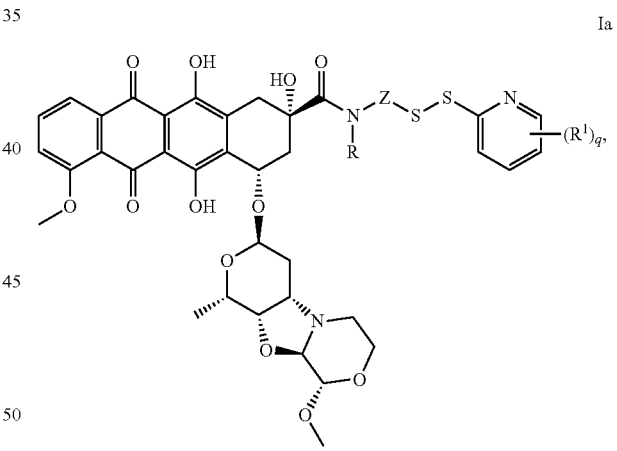

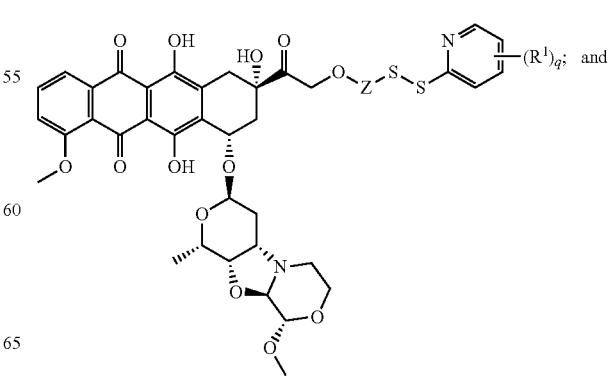

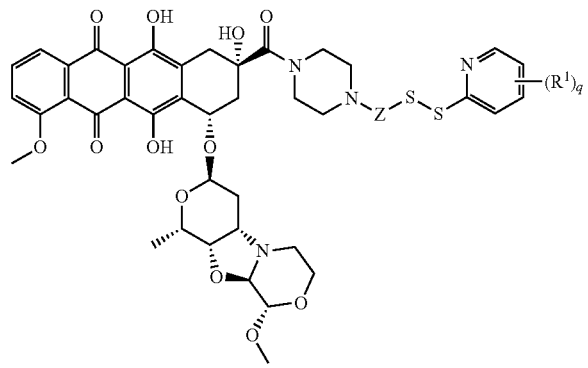

where R[1] is NO$_2$, Cl, F, CN or Br; and q is 0, 1, or 2.

An exemplary linker-drug intermediate include wherein R[1] is NO$_2$ and q is 1.

An exemplary linker-drug intermediate is Formula Id:

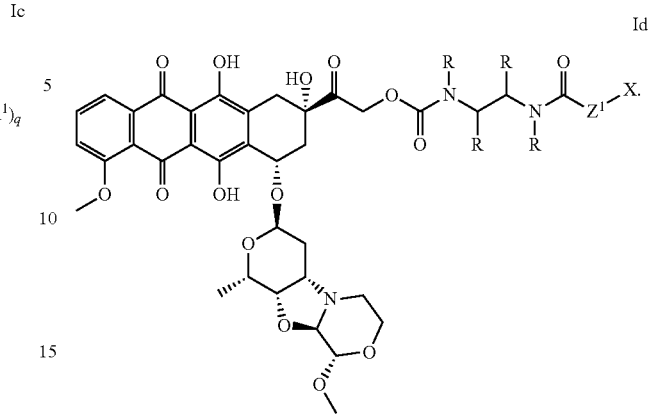

Exemplary anthracycline disulfide, linker-drug intermediates useful for preparing antibody-drug conjugates of the invention are included in Table 1. The synthesis of anthracycline disulfide, linker-drug (LD) intermediates are described in Example 1.

TABLE 1

Anthracycline disulfide, Linker-drug intermediates

| LD No. | Structure |
|---|---|
| LD-51 | 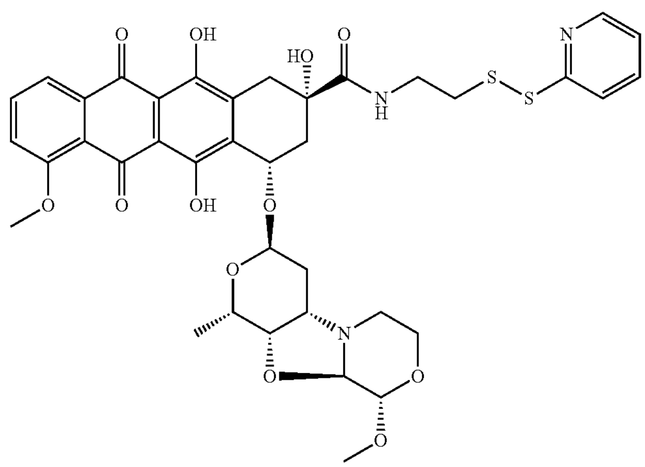 [SMILES: COc1cccc2c1C(=O)c1c(O)c3c(c(O)c1C2=O)C[C@@](O)(C(=O)NCCSSc1ccccn1)C[C@@H]3O[C@H]1C[C@H]2[C@H](O[C@@H]3[C@@H](OC)OCCN32)[C@H](C)O1] |
| LD-52 | 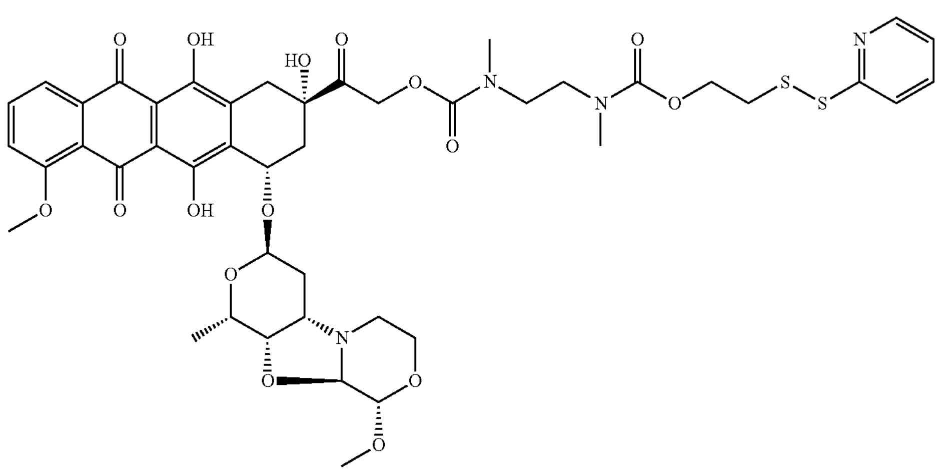 [SMILES: COc1cccc2c1C(=O)c1c(O)c3c(c(O)c1C2=O)C[C@@](O)(C(=O)COC(=O)N(C)CCN(C)C(=O)OCCSSc1ccccn1)C[C@@H]3O[C@H]1C[C@H]2[C@H](O[C@@H]3[C@@H](OC)OCCN32)[C@H](C)O1] |

TABLE 1-continued
Anthracycline disulfide, Linker-drug intermediates
| LD No. | Structure |
|---|---|
| LD-53 | 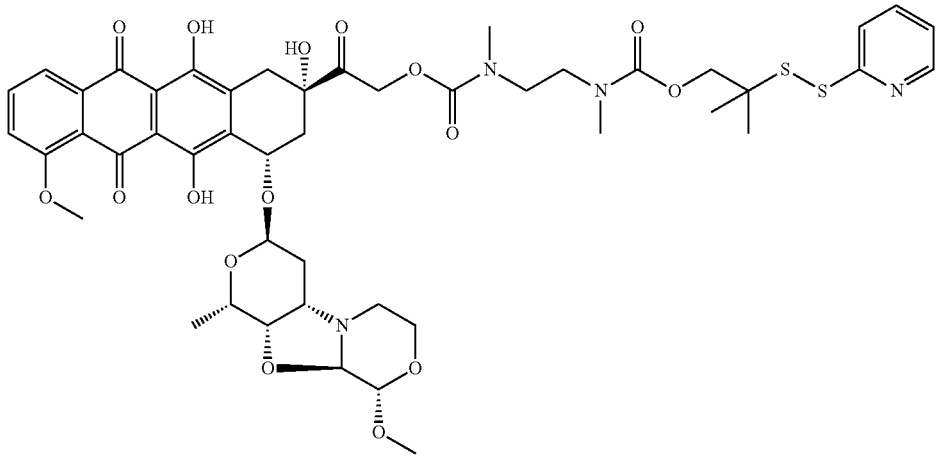 [SMILES: COc1cccc2c1C(=O)c1c(O)c3c(c(O)c1C2=O)C[C@@](O)(C(=O)COC(=O)N(C)CCN(C)C(=O)OCC(C)(C)SSc1ccccn1)C[C@@H]3O[C@H]1C[C@H]2[C@H](O[C@@H]3[C@@H](OC)OCCN32)[C@H](C)O1] |
| LD-54 | 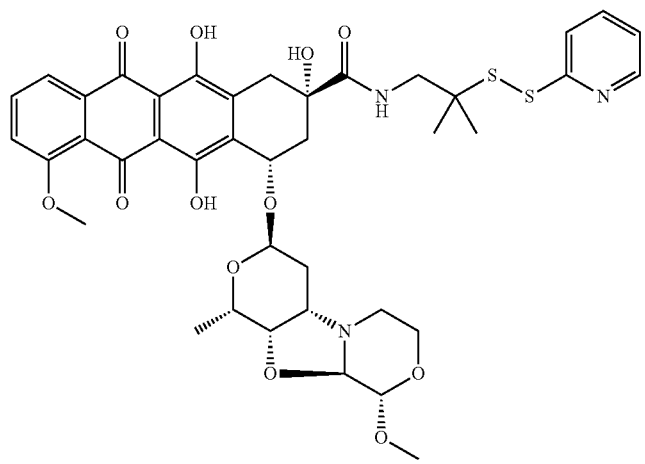 [SMILES: COc1cccc2c1C(=O)c1c(O)c3c(c(O)c1C2=O)C[C@@](O)(C(=O)NCC(C)(C)SSc1ccccn1)C[C@@H]3O[C@H]1C[C@H]2[C@H](O[C@@H]3[C@@H](OC)OCCN32)[C@H](C)O1] |
| LD-55 | 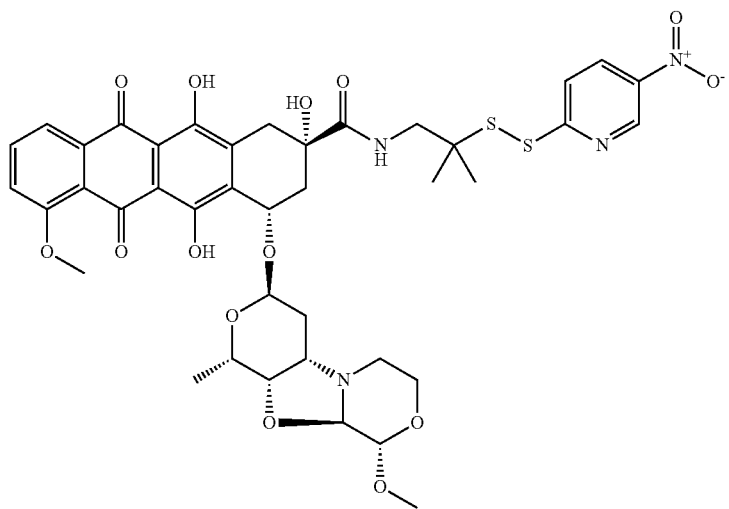 [SMILES: COc1cccc2c1C(=O)c1c(O)c3c(c(O)c1C2=O)C[C@@](O)(C(=O)NCC(C)(C)SSc1ccc([N+](=O)[O-])cn1)C[C@@H]3O[C@H]1C[C@H]2[C@H](O[C@@H]3[C@@H](OC)OCCN32)[C@H](C)O1] |

TABLE 1-continued

Anthracycline disulfide, Linker-drug intermediates

| LD No. | Structure |
|---|---|
| LD-56 | 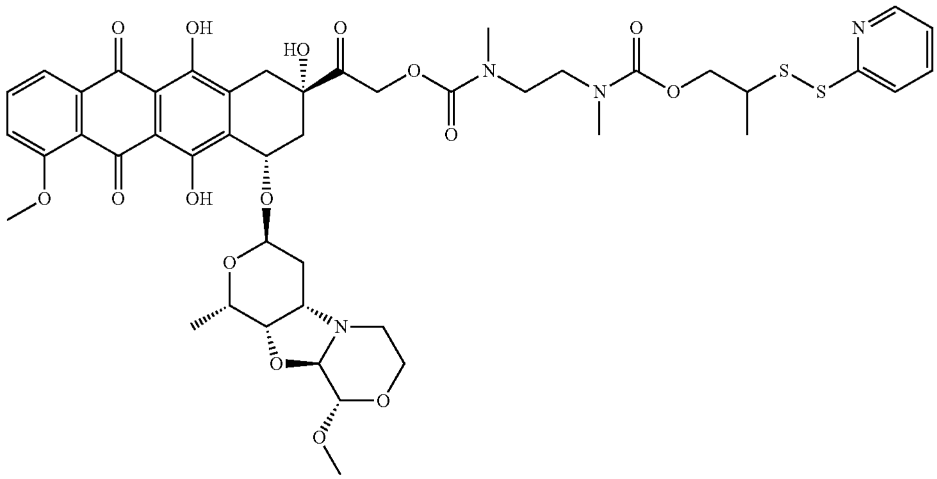 [SMILES: COc1cccc2c1C(=O)c1c(O)c3c(c(O)c1C2=O)C[C@@](O)(C(=O)COC(=O)N(C)CCN(C)C(=O)OCC(C)SSc1ccccn1)C[C@@H]3O[C@H]1C[C@H]2[C@H](O[C@@H]3[C@@H](OC)OCCN32)[C@H](C)O1] |
| LD-57 | 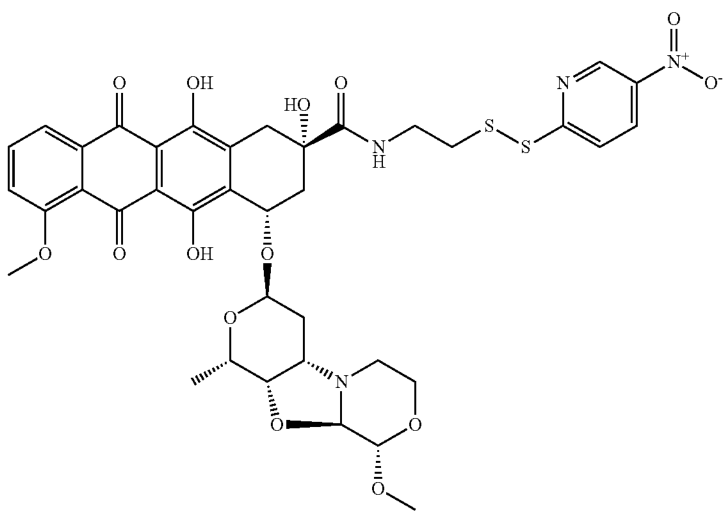 [SMILES: COc1cccc2c1C(=O)c1c(O)c3c(c(O)c1C2=O)C[C@@](O)(C(=O)NCCSSc1ccc([N+](=O)[O-])cn1)C[C@@H]3O[C@H]1C[C@H]2[C@H](O[C@@H]3[C@@H](OC)OCCN32)[C@H](C)O1] |
| LD-58 | 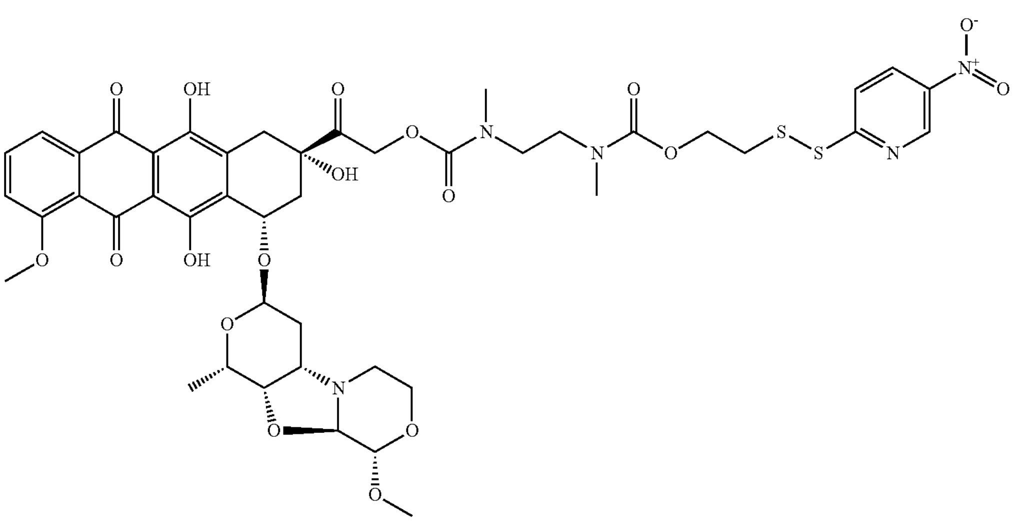 [SMILES: COc1cccc2c1C(=O)c1c(O)c3c(c(O)c1C2=O)C[C@@](O)(C(=O)COC(=O)N(C)CCN(C)C(=O)OCCSSc1ccc([N+](=O)[O-])cn1)C[C@@H]3O[C@H]1C[C@H]2[C@H](O[C@@H]3[C@@H](OC)OCCN32)[C@H](C)O1] |

TABLE 1-continued
Anthracycline disulfide, Linker-drug intermediates
| LD No. | Structure |
|---|---|
| LD-59 | 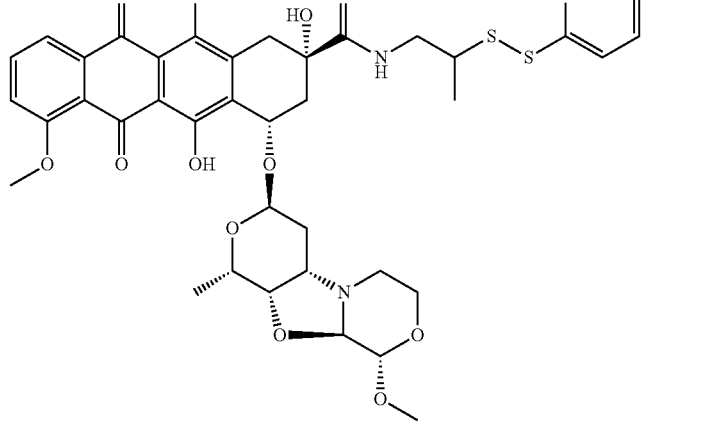 |
| LD-60 | 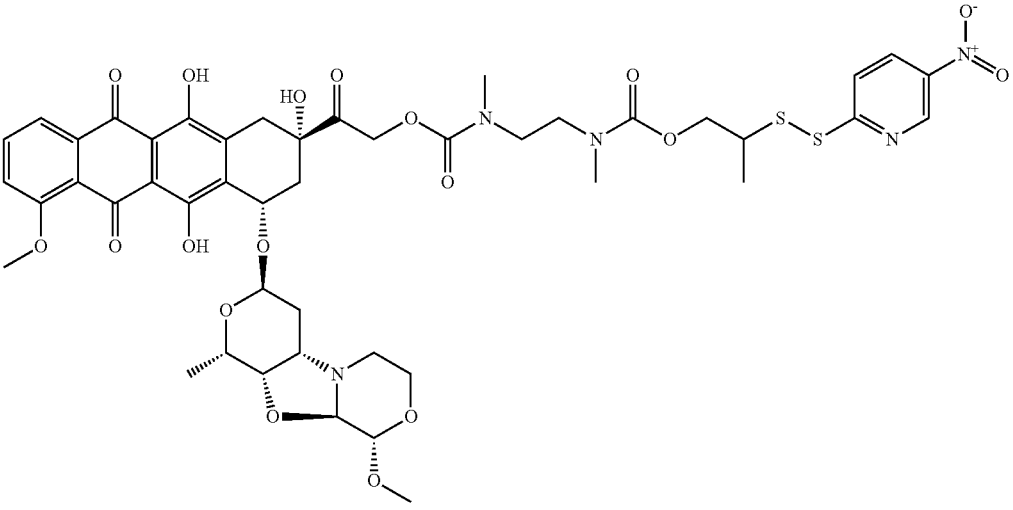 [SMILES: COc1cccc2c1C(=O)c1c(O)c3c(c(O)c1C2=O)C[C@@](O)(C(=O)COC(=O)N(C)CCN(C)C(=O)OCC(C)SSc1ccc([N+](=O)[O-])cn1)C[C@@H]3O[C@H]1C[C@H]2[C@H](O[C@@H]3[C@@H](OC)OCCN32)[C@H](C)O1] |
| LD-61 | 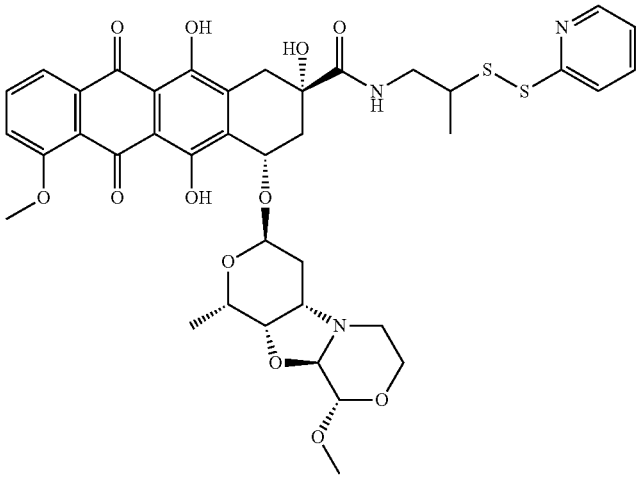 [SMILES: COc1cccc2c1C(=O)c1c(O)c3c(c(O)c1C2=O)C[C@@](O)(C(=O)NCC(C)SSc1ccccn1)C[C@@H]3O[C@H]1C[C@H]2[C@H](O[C@@H]3[C@@H](OC)OCCN32)[C@H](C)O1] |

TABLE 1-continued

Anthracycline disulfide, Linker-drug intermediates

| LD No. | Structure |
|---|---|
| LD-62 | 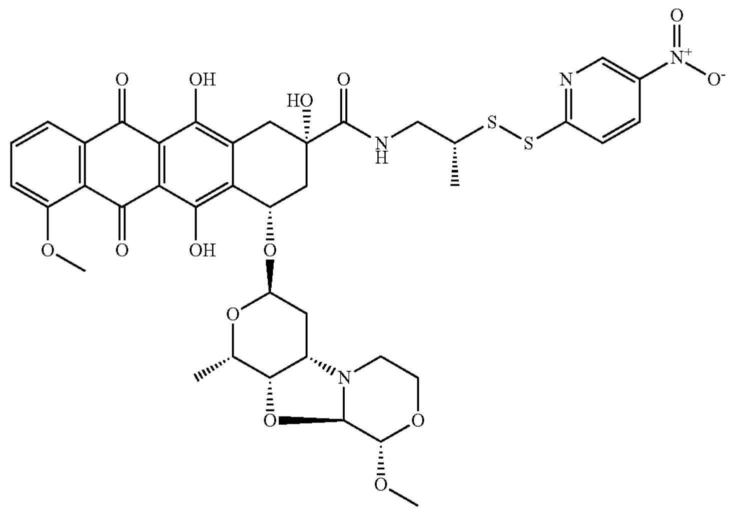 [SMILES: COc1cccc2c1C(=O)c1c(O)c3c(c(O)c1C2=O)C[C@@](O)(C(=O)NC[C@@H](C)SSc1ccc([N+](=O)[O-])cn1)C[C@@H]3O[C@H]1C[C@H]2[C@H](O[C@@H]3[C@@H](OC)OCCN32)[C@H](C)O1] |
| LD-63 | 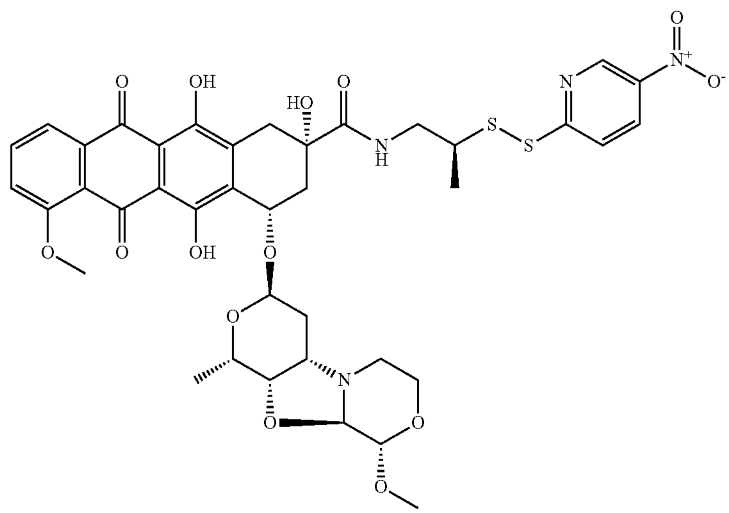 [SMILES: COc1cccc2c1C(=O)c1c(O)c3c(c(O)c1C2=O)C[C@@](O)(C(=O)NC[C@H](C)SSc1ccc([N+](=O)[O-])cn1)C[C@@H]3O[C@H]1C[C@H]2[C@H](O[C@@H]3[C@@H](OC)OCCN32)[C@H](C)O1] |

Antibody-Drug Conjugates (ADC)

The antibody-drug conjugate (ADC) compounds of the invention comprise an antibody specific for a tumor-associated antigen linked to a potent anthracycline drug moiety, and include those with therapeutic activity, effective against a number of hyperproliferative disorders, including cancer. The biological activity of the drug moiety is modulated by conjugation to an antibody. The ADC of the invention selectively deliver an effective dose of the anthracycline drug, or toxin, to a tumor cell or site whereby greater selectivity, i.e. a lower efficacious dose, may be achieved while increasing the therapeutic index ("therapeutic window"). In an exemplary embodiment, the ADC compounds include a cysteine-engineered antibody conjugated, i.e. covalently attached by a linker, to the anthracycline drug moiety.

An antibody-drug conjugate compound of the invention comprises an antibody covalently attached by a disulfide, linker L and an optional spacer Z to one or more anthracycline derivative drug moieties D, the compound having Formula II:

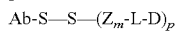

or a pharmaceutically acceptable salt thereof, wherein:

Ab is an antibody which binds to one or more tumor-associated antigens or cell-surface receptors selected from (1)-(53):

(1) BMPR1B (bone morphogenetic protein receptor-type IB);

(2) E16 (LAT1, SLC7A5);

(3) STEAP1 (six transmembrane epithelial antigen of prostate);

(4) MUC16 (0772P, CA125);

(5) MPF (MPF, MSLN, SMR, megakaryocyte potentiating factor, mesothelin);

(6) Napi2b (NAPI-3B, NPTIIb, SLC34A2, solute carrier family 34 (sodium phosphate), member 2, type II sodium-dependent phosphate transporter 3b);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008O16Rik, RIKEN cDNA 2700050C12, RIKEN cDNA 2700050C12 gene);

(9) ETBR (Endothelin type B receptor);

(10) MSG783 (RNF124, hypothetical protein FLJ20315);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);

(12) TrpM4 (BR22450, FLJ20041, TRPM4, TRPM4B, transient receptor potential cation channel, subfamily M, member 4);

(13) CRIPTO (CR, CR1, CRGF, CRIPTO, TDGF1, teratocarcinoma-derived growth factor);

(14) CD21 (CR2 (Complement receptor 2) or C3DR (C3d/Epstein Barr virus receptor) or Hs 73792);

(15) CD79b (CD79B, CD7913, IGb (immunoglobulin-associated beta), B29);

(16) FcRH2 (IFGP4, IRTA4, SPAP1A (SH2 domain containing phosphatase anchor protein 1a), SPAP1B, SPAP1C);

(17) HER2;

(18) NCA;

(19) MDP;

(20) IL20Rα;

(21) Brevican;

(22) EphB2R;

(23) ASLG659;

(24) PSCA;

(25) GEDA;

(26) BAFF-R (B cell-activating factor receptor, BLyS receptor 3, BR3);

(27) CD22 (B-cell receptor CD22-B isoform);

(28) CD79a (CD79A, CD79a, immunoglobulin-associated alpha);

(29) CXCR5 (Burkitt's lymphoma receptor 1);

(30) HLA-DOB (Beta subunit of MHC class II molecule (Ia antigen));

(31) P2X5 (Purinergic receptor P2X ligand-gated ion channel 5);

(32) CD72 (B-cell differentiation antigen CD72, Lyb-2);

(33) LY64 (Lymphocyte antigen 64 (RP105), type I membrane protein of the leucine rich repeat (LRR) family);

(34) FcRH1 (Fc receptor-like protein 1);

(35) FcRH5 (IRTA2, Immunoglobulin superfamily receptor translocation associated 2);

(36) TENB2 (putative transmembrane proteoglycan); and

(37) PMEL17 (silver homolog; SILV; D12S53E; PMEL17; SI; SIL);

(38) TMEFF1 (transmembrane protein with EGF-like and two follistatin-like domains 1; Tomoregulin-1);

(39) GDNF-Ra1 (GDNF family receptor alpha1; GFRA1; GDNFR; GDNFRA; RETL1; TRNR1; RET1L; GDNFR-alpha1; GFR-ALPHA-1);

(40) Ly6E (lymphocyte antigen 6 complex, locus E; Ly67, RIG-E, SCA-2, TSA-1);

(41) TMEM46 (shisa homolog 2 (*Xenopus laevis*); SHISA2);

(42) Ly6G6D (Lymphocyte antigen 6 complex, locus G6D; Ly6-D, MEGT1);

(43) LGR5 (leucine-rich repeat-containing G protein-coupled receptor 5; GPR49, GPR67);

(44) RET (ret proto-oncogene; MEN2A; HSCR1; MEN2B; MTC1; PTC; CDHF12; Hs.168114; RET51; RET-ELE1);

(45) LY6K (lymphocyte antigen 6 complex, locus K; LY6K; HSJ001348; FLJ35226);

(46) GPR19 (G protein-coupled receptor 19; Mm.4787);

(47) GPR54 (KISS1 receptor; KISS1R; GPR54; HOT7T175; AXOR12);

(48) ASPHD1 (aspartate beta-hydroxylase domain containing 1; LOC253982);

(49) Tyrosinase (TYR; OCAIA; OCA1A; tyrosinase; SHEP3);

(50) TMEM118 (ring finger protein, transmembrane 2; RNFT2; FLJ14627);

(51) GPR172A (G protein-coupled receptor 172A; GPCR41; FLJ11856; D15Ertd747e);

(52) CD33; and

(53) CLL-1;

D is an anthracycline derivative selected from the structure:

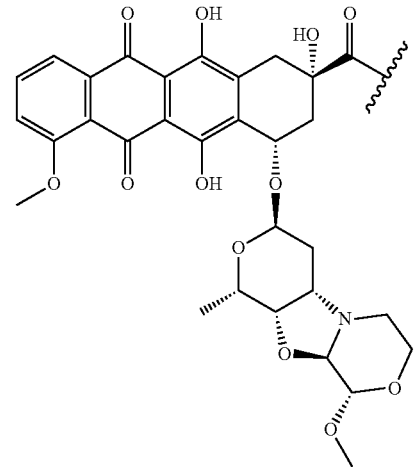 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

where the wavy line indicates the attachment to L;

L is a linker selected from —CH$_2$O—, —CH$_2$N(R)—, —N(R)—, —N(R)(C$_1$-C$_{12}$ alkylene)-, —N(R)(C$_2$-C$_8$ alkenylene)-, —N(R)(C$_2$-C$_8$ alkynylene)-, —N(R)(CH$_2$CH$_2$O)$_n$—, and the structure:

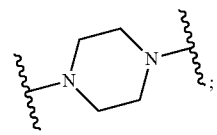 [SMILES: *N1CCN(*)CC1]

where the wavy lines indicate the attachments to D and Z; and

Z is an optional spacer selected from —CH$_2$C(O)—, —CH$_2$C(O)NR(C$_1$-C$_{12}$ alkylene)-, and the structures:

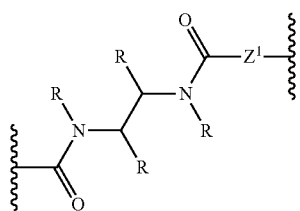

R is H, $C_1$-$C_{12}$ alkyl, or $C_6$-$C_{20}$ aryl;

$Z^1$ is selected from —($C_1$-$C_{12}$ alkylene)-, —($C_2$-$C_8$ alkenylene)-, —($C_2$-$C_8$ alkynylene)-, and —$(CH_2CH_2O)_n$—, m is 0 or 1;

n is 1 to 6; and p is an integer from 1 to 8.

TABLE 2

| ADC No. | ADC formula | linker-drug LD No. (Table 1) | DAR* |
|---|---|---|---|
| ADC-101 | Thio Hu Anti-Her2 4D5 HC A118C-(LD-51) | 51 | 1.8 |
| ADC-102 | Thio Hu Anti-CD22 10F4v3 HC A118C-(LD-51) | 51 | 1.8 |
| ADC-103 | Thio Hu Anti-Her2 4D5 HC A118C-(LD-52) | 52 | 1.8 |
| ADC-104 | Thio Hu Anti-CD22 10F4v3 HC A118C-(LD-52) | 52 | 1.7 |
| ADC-105 | Thio Hu Anti-CD33 GM15.33 HC A118C-(LD-56) | 56 | 1.7 |
| ADC-106 | Thio Hu Anti-Napi3b 10H1.11.4B HC A118C-(LD-56) | 56 | 1.6 |
| ADC-107 | Thio Hu Anti-Her2 7C2 HC A118C-(LD-51) | 51 | 1.6 |
| ADC-108 | Thio Hu Anti-Her2 7C2 LC K149C-(LD-51) | 51 | 1.7 |
| ADC-109 | Thio Hu anti-Her2 7C2 LC K149C-(LD-57) | 57 | 1.9 |
| ADC-110 | Thio Hu anti-CD33 15G15.3 LC K149C-(LD-57) | 57 | 1.9 |
| ADC-111 | Thio Hu anti-Her2 4D5 HC A118C-(LD-56) | 56 | 1.2 |
| ADC-112 | Thio Hu Anti-Her2 4D5 HC A118C-(LD-52) | 52 | 1.8 |
| ADC-113 | Thio Hu Anti-Napi3b 10H1.11.4B HC A118C-(LD-51) | 51 | 1.9 |
| ADC-114 | Thio Hu anti-Her2 7C2 HC A118C-(LD-57) | 57 | 1.9 |
| ADC-115 | Thio Hu Anti-CD33 15G15.3 LC K149C-(LD-59) | 59 | 1.6 |
| ADC-116 | Thio Hu anti-Her2 7C2 LC K149C-(LD-59) | 59 | 1.5 |
| ADC-117 | Thio Hu anti-CLL-1 6E7.N54A LC K149C-(LD-59) | 59 | 1.7 |
| ADC-118 | Thio Hu anti-CLL-1 6E7.N54A LC K149C-(LD-57) | 57 | 2.0 |
| ADC-119 | Thio Hu Anti-Her2 4D5 HC A118C-(LD-61) | 61 | 1.9 |
| ADC-120 | Thio Hu anti-CD22 10F4v3 LC K149C-(LD-57) | 57 | 1.9 |
| ADC-121 | Thio Hu Anti-Napi3b 10H1.11.4B LC K149C-(LD-57) | 57 | 1.9 |
| ADC-122 | Thio Hu anti-CD22 10F4v3 LC K149C-(LD-59) | 59 | 1.7 |
| ADC-123 | Thio Hu Anti-Napi3b 10H1.11.4B LC K149C-(LD-59) | 59 | 1.7 |
| ADC-124 | Thio Hu anti-CD22 10F4v3 LC K149C-(LD-58) | 58 | 1.9 |
| ADC-125 | Thio Hu Anti-Napi3b 10H1.11.4B LC K149C-(LD-58) | 58 | 1.9 |
| ADC-126 | Thio Hu anti-CD22 10F4v3 LC K149C-(LD-60) | 60 | 1.7 |
| ADC-127 | Thio Hu Anti-Napi3b 10H1.11.4B LC K149C-(LD-60) | 60 | 1.6 |
| ADC-128 | Thio Hu-Anti 4D5 HC A140C-(LD-59) | 59 | 1.2 |
| ADC-129 | Thio Hu-Anti 4D5 LC K149C-(LD-59) | 59 | 1.5 |
| ADC-130 | Thio Hu-Anti 4D5 LC V205C-(LD-59) | 59 | 1.2 |
| ADC-131 | Thio Hu-Anti 4D5 HC A118C-(LD-59) | 59 | 1.6 |
| ADC-132 | Thio Hu-Anti 4D5 LC S121C-(LD-59) | 59 | 0.5 |
| ADC-133 | Thio Hu anti-CLL-1 6E7.N54A LC K149C-(LD-57) | 57 | 2.0 |
| ADC-134 | Thio Hu Anti-Her2 7C2 LC K149C-(LD-62) | 62 | 1.7 |
| ADC-135 | Thio Hu Anti-Her2 7C2 LC K149C-(LD-63) | 63 | 1.7 |
| ADC-136 | Thio Hu Anti-Her2 7C2 LC K149C-(LD-62) | 62 | 1.8 |
| ADC-137 | Thio Hu anti-Her2 7C2 LC K149C-(LD-57) | 57 | 1.9 |

DAR = drug/antibody ratio average
A118C (EU numbering) = A121C (Sequential numbering) = A114C (Kabat numbering)
Wild-type ("WT"), cysteine engineered mutant antibody ("thio"), light chain ("LC"), heavy chain ("HC"), 6-maleimidocaproyl ("MC"), maleimidopropanoyl ("MP"), valine-citrulline ("val-cit" or "vc"), alanine-phenylalanine ("ala-phe"), p-aminobenzyl ("PAB"), and p-aminobenzyloxycarbonyl ("PABC")

TABLE 3

| | Non-cleavable, non-disulfide, comparator ADC: | |
|---|---|---|
| ADC-138 | Thio Hu anti-Her2 7C2 LC K149C-(ethylmaleimide-PNU) | 1.8 |
| ADC-139 | Thio Hu Anti-CD33 15G15.3 LC K149C-(ethylmaleimide-PNU) | 2.0 |
| ADC-140 | Thio Hu Anti-Her2 7C2 HC A118C-(ethylmaleimide-PNU) | 1.7 |
| ADC-141 | Trastuzumab emtansine (KADCYLA ®) | 3.8 |

TABLE 3-continued

Non-cleavable, non-disulfide, comparator ADC:

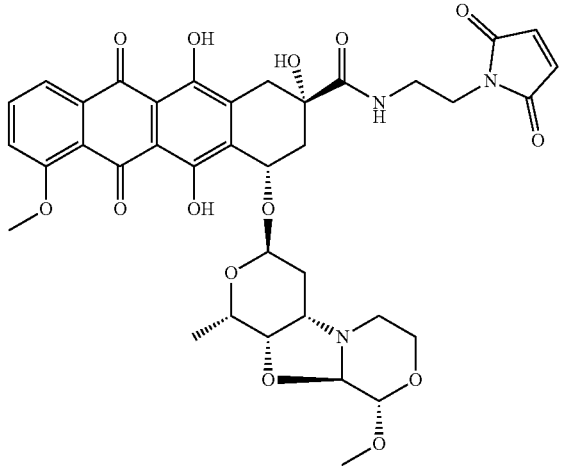 [SMILES: COc1cccc2c1C(=O)c1c(O)c3c(c(O)c1C2=O)C[C@@](O)(C(=O)NCCN1C(=O)C=CC1=O)C[C@@H]3O[C@H]1C[C@H]2[C@H](O[C@@H]3[C@@H](OC)OCCN32)[C@H](C)O1]

(2S,4S)-4-[[(1S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-N-[2-(2,5-dioxopyrrol-1-yl)ethyl]-2,5,12-trihydroxy-7-methoxy-6,11-dioxo-3,4-dihydro-1H-tetracene-2-carboxamide (ethylmaleimide-PNU)

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody-drug conjugates (ADC) was measured by a cell proliferation assay (Example 4). The ADC of the invention showed surprising and unexpected potency in inhibition of tumor cell proliferation. Potency of the ADC was correlated with target antigen expression of the cells. The tested conjugates are capable of binding to the specific antigen expressed on the surface of cells and causing the death of those cells in vitro.

The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713; 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiterGlo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

Cell-based in vitro assays are used to measure viability (proliferation), cytotoxicity, and induction of apoptosis (caspase activation) of the ADC of the invention. Generally, the cytotoxic or cytostatic activity of an antibody-drug conjugate (ADC) is measured by: exposing mammalian cells expressing antigen such as Her2 or MUC16 polypeptide to ADC in a cell culture medium; culturing the cells for a period from about 6 hours to about 5 days; and measuring cell viability. Mammalian cells useful for cell proliferation assays for anti-MUC16 ADC include: (1) a MUC16 polypeptide-expressing cell line OVCAR-3; (2) a PC3-derived cell line engineered to stably express a portion of the MUC16 polypeptide on its cell surface (PC3/MUC16); (3) the parental PC3 cell line that does not express the MUC16 polypeptide; and (4) a PC3 cell line that does not express MUC16 polypeptide but carries the vector used to drive exogenous MUC16 expression (PC3/neo).

FIG. 1 shows the efficacy of antibody-drug conjugates in a plot of SK-BR-3 in vitro cell viability at 5 days versus concentrations (μg/ml) of Thio Hu anti-Her2 7C2 HC A118C-(LD-57) 114, Thio Hu anti-Her2 7C2 LC K149C-(LD-57) 109, and Thio Hu anti-CD33 15G15.3 LC K149C-(LD-57) 110. The Her2 antigen is highly expressed in SK-BR-3 cells. Both anti-Her2 ADC 114 and 109 showed linear, dose response cell-killing activity. The light chain K149C mutant ADC 109 showed the same or slightly more potent cell killing activity than the heavy chain A118C mutant ADC 114. Control, off-target anti-CD33 ADC 110 shows less activity.

FIG. 2 shows the efficacy of antibody-drug conjugates in a plot of SK-BR-3 in vitro cell viability at 5 days versus concentrations (μg/ml) of Thio Hu anti-Her2 7C2 LC K149C-(LD-59) 116, Thio Hu anti-Her2 7C2 LC K149C-(LD-57) 109, and Thio Hu Anti-CD33 15G15.3 LC K149C-(LD-59) 115. Both anti-Her2 ADC 116 and 109 showed linear, dose response cell-killing activity. Antibody-drug conjugate 109 with the unsubstituted, less hindered, ethyl disulfide linker 109 showed the same or slightly more potent cell killing activity than the methyl substituted, more hindered disulfide linker ADC-116.

FIG. 6 shows the efficacy of antibody-drug conjugates in a plot of BJAB.luc in vitro cell viability at 5 days versus concentrations (μg/ml) of Thio Hu Anti-Napi3b 10H1.11.4B LC K149C-(LD-57) 121, Thio Hu anti-CD22 10F4v3 LC K149C-(LD-57) 120, Thio Hu Anti-Napi3b 10H1.11.4B LC K149C-(LD-59) 123, Thio Hu anti-CD22 10F4v3 LC K149C-(LD-59) 122, Thio Hu Anti-Napi3b 10H1.11.4B LC K149C-(LD-58) 125, Thio Hu anti-CD22 10F4v3 LC K149C-(LD-58) 124, Thio Hu Anti-Napi3b 10H1.11.4B LC K149C-(LD-60) 127, and Thio Hu anti-CD22 10F4v3 LC K149C-(LD-60) 126.

FIG. 7 shows the efficacy of antibody-drug conjugates in a plot of WSU-DLCL2 in vitro cell viability at 5 days versus concentrations (μg/ml) of Thio Hu Anti-Napi3b 10H1.11.4B LC K149C-(LD-57) 121, Thio Hu anti-CD22 10F4v3 LC K149C-(LD-57) 120, Thio Hu Anti-Napi3b 10H1.11.4B LC K149C-(LD-59) 123, Thio Hu anti-CD22 10F4v3 LC K149C-(LD-59) 122, Thio Hu Anti-Napi3b 10H1.11.4B LC K149C-(LD-58) 125, Thio Hu anti-CD22 10F4v3 LC K149C-(LD-58) 124, Thio Hu Anti-Napi3b 10H1.11.4B LC K149C-(LD-60) 127, and Thio Hu anti-CD22 10F4v3 LC K149C-(LD-60) 126.

In Vivo Efficacy

The in vivo efficacy of antibody-drug conjugates (ADC) of the invention can be measured by tumor xenograft studies in mice (Example 22). The in vivo efficacy of antibody-drug conjugates (ADC) was measured tumor growth inhibition in mice (Example 21). The ADC of the invention showed surprising and unexpected potency in inhibition of tumor growth. Efficacy of the ADC was correlated with target antigen expression of the tumor cells.

The efficacy of antibody-drug conjugates were measured in vivo by implanting allografts or xenografts of cancer cells in rodents and treating the tumors with ADC. Variable results are to be expected depending on the cell line, the specificity of antibody binding of the ADC to receptors present on the cancer cells, dosing regimen, and other factors. The in vivo efficacy of the ADC was measured using a transgenic explant mouse model expressing moderate to high levels of a tumor-associated antigen, such as Her2, MUC16, and CD33. Subjects were treated once with ADC and monitored over 3-6 weeks to measure the time to tumor doubling, log cell kill, and tumor shrinkage. Follow up dose-response and multi-dose experiments were conducted.

For example, the in vivo efficacy of an anti-HER2 ADC of the invention can be measured by a high expressing HER2 transgenic explant mouse model (Phillips et al (2008) Cancer Res. 68:9280-90). An allograft is propagated from the Fo5 mmtv transgenic mouse which does not respond to, or responds poorly to, HERCEPTIN® therapy. Subjects were treated once with ADC at certain dose levels (mg/kg) and placebo buffer control (Vehicle) and monitored over two weeks or more to measure the time to tumor doubling, log cell kill, and tumor shrinkage.

FIG. 3 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: Vehicle: Histidine Buffer #8: 20 mM Histidine Acetate, pH 5.5, 240 mM Sucrose, 0.02% PS 20, Thio Hu Anti-Her2 7C2 HC A118C-(LD-51) 107, and Thio Hu Anti-Her2 7C2 LC K149C-(LD-51) 108. ADC were dosed at 3 mg/kg one time IV at day 0. Both antibody-drug conjugates 107 and 108 showed tumor growth inhibition whereas the light chain K149C mutant ADC 108 showed greater efficacy than the heavy chain A118C mutant ADC 107.

FIG. 4 shows the efficacy of antibody-drug conjugates in a plot of the in vivo fitted tumor volume change over time in KPL4 tumor model in scid beige mice inoculated in the thoracic mammary fat pad at a volume of 0.2 ml. When tumors reached a mean tumor volume of 100-250 mm3, they were grouped into 9 groups of 8-10 mice each. A single treatment was administered intravenously via the tail vein on Day 0 as follows: (01) Vehicle: Histidine Buffer #8: 20 mM Histidine Acetate, pH 5.5, 240 mM Sucrose, 0.02% PS 20, (02) Thio Hu anti-Her2 7C2 LC K149C-(ethylmaleimide) 0.3 mg/kg 138, (03) Thio Hu anti-Her2 7C2 LC K149C-(ethylmaleimide) 1 mg/kg 138, (04) Thio Hu anti-Her2 7C2 LC K149C-(ethylmaleimide) 3 mg/kg 138, (05) Thio Hu anti-Her2 7C2 LC K149C-(LD-57) 0.3 mg/kg 109, (06) Thio Hu anti-Her2 7C2 LC K149C-(LD-57) 1 mg/kg 109, (07) Thio Hu anti-Her2 7C2 LC K149C-(LD-57) 3 mg/kg 109, (08) Thio Hu Anti-CD33 15G15.3 LC K149C-(ethylmaleimide) 3 mg/kg 139, and (09) Thio Hu anti-CD33 15G15.3 LC K149C-(LD-57) 3 mg/kg 110.

Anti-HER2 7C2 antibody-drug conjugates 138 and 109 showed a dose-dependent effect on tumor growth. Non specific anti-CD33 antibody-drug conjugates 139 and 110 showed little or no tumor growth inhibition.

Figure 5:
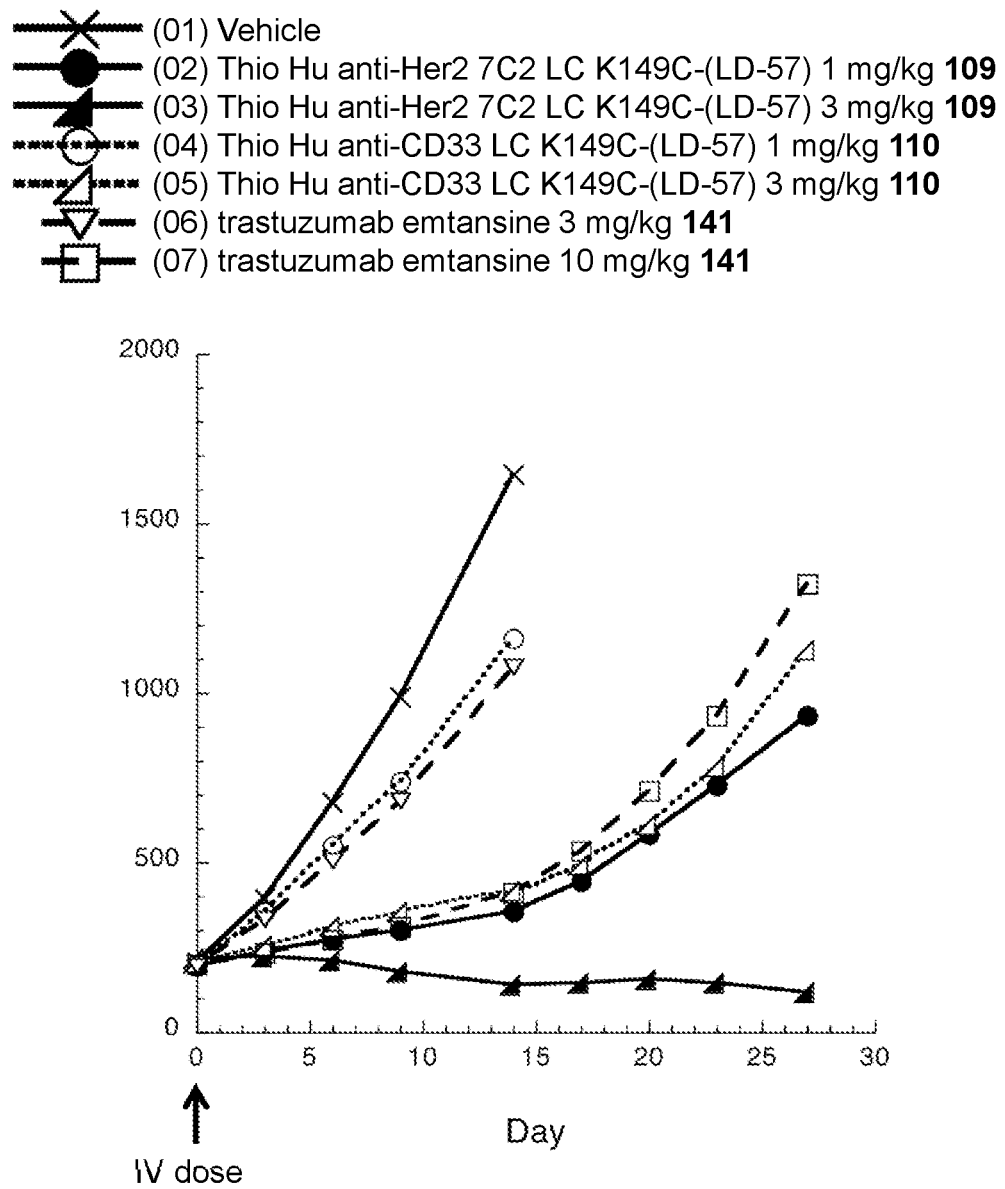
FIG. 5 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: (01) Vehicle: Histidine Buffer #8: 20 mM Histidine Acetate, pH 5.5, 240 mM Sucrose, 0.02% PS 20, (02) Thio Hu anti-Her2 7C2 LC K149C-(LD-57) 1 mg/kg 109, (03) Thio Hu anti-Her2 7C2 LC K149C-(LD-57) 3 mg/kg 109, (04) Thio Hu anti-CD33 15G15.3 LC K149C-(LD-57) 1 mg/kg 110, (05) Thio Hu anti-CD33 15G15.3 LC K149C-(LD-57) 3 mg/kg 110, (06) trastuzumab emtansine 3 mg/kg 141, and (07) trastuzumab emtansine 10 mg/kg 141.

FIG. 5 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: (01) Vehicle: Histidine Buffer #8: 20 mM Histidine Acetate, pH 5.5, 240 mM Sucrose, 0.02% PS 20, (02) Thio Hu anti-Her2 7C2 LC K149C-(LD-57) 1 mg/kg 109, (03) Thio Hu anti-Her2 7C2 LC K149C-(LD-57) 3 mg/kg 109, (04) Thio Hu anti-CD33 15G15.3 LC K149C-(LD-57) 1 mg/kg 110, (05) Thio Hu anti-CD33 15G15.3 LC K149C-(LD-57) 3 mg/kg 110, (06) trastuzumab emtansine 3 mg/kg 141, and (07) trastuzumab emtansine 10 mg/kg 141.

Comparator ADC, trastuzumab emtansine (KADCYLA®, trastuzumab-MCC-DM1 (T-DM1) 141, is an antibody-drug conjugate (CAS Reg. No. 139504-50-0; Phillips G. et al. (2008) Cancer Res. 68:9280-90), and has the structure:

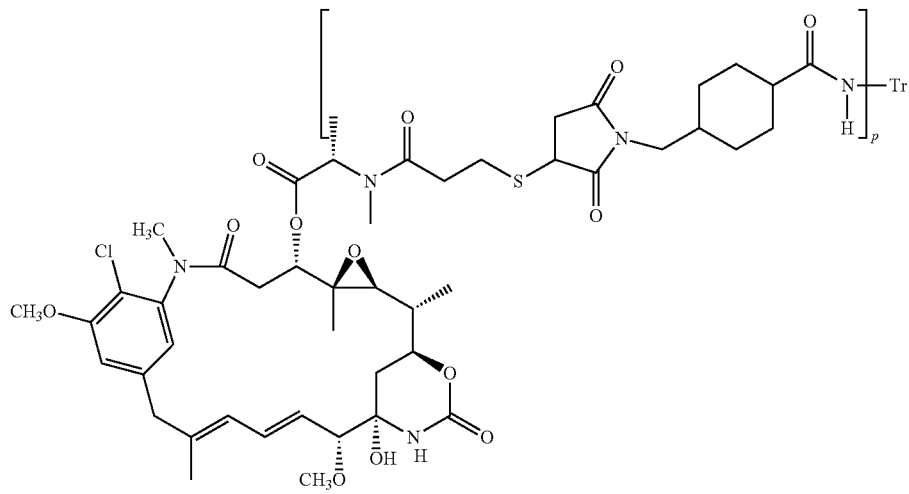

Anti-HER2 7C2 antibody-drug conjugate 109 showed a dose-dependent effect on tumor growth. Non-specific anti-CD33 antibody-drug conjugate 110 showed little tumor growth inhibition at 1 mg/kg and modest tumor growth inhibition at 3 mg/kg. Anti-HER2 7C2 antibody-drug conjugate 109 showed more efficacy than anti-HER2 4D5 trastuzumab emtansine 141 (Phillips G. et al. (2008) Cancer Res. 68:9280-90) at equivalent dose (3 mg/kg) or at higher 10 mg/kg dose.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Antibody-Drug Conjugate Methods of Treatment

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

The antibody-drug conjugates (ADC) of the invention may be administered by any route appropriate to the condition to be treated. The ADC will typically be administered parenterally, i.e. infusion, subcutaneous, intramuscular, intravenous, intradermal, intrathecal and epidural.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1 Synthesis of Anthracycline Disulfide, Linker-Drug (LD) Intermediates (Table 1)

LD-51: Synthesis of (2S,4S)-4-[[(1S,3R,4aS,9S, 9aR,10aS)-9-methoxy-1-methyl-3,4,4a,6,7,9,9a,10a-octahydro-1H-pyrano[1,2]oxazolo[3,4-b][1,4] oxazin-3-yl]oxy]-2,5,12-trihydroxy-7-methoxy-6,11-dioxo-N-[2-(2-pyridyldisulfanyl)ethyl]-3,4-dihydro-1H-tetracene-2-carboxamide

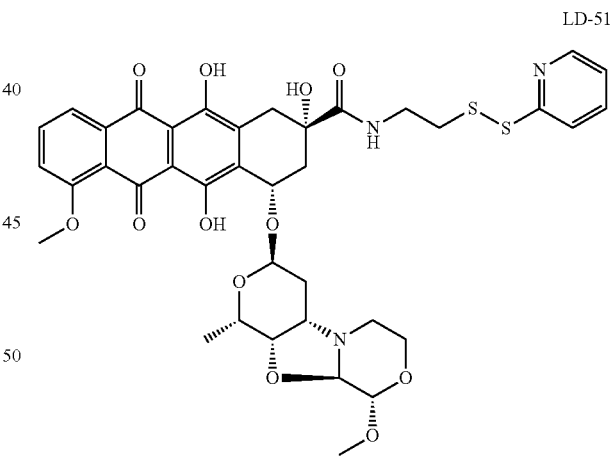

LD-51

Following Example 3 of U.S. Pat. No. 8,389,697, to a solution of PNU-159682 (15.3 mg, 0.02038 mmol), prepared as reported in WO 1998/02446 and Example 1 of U.S. Pat. No. 8,470,984, in 3 ml of methanol and 2 ml of H$_2$O, a solution of NaIO$_4$ (5.1 mg, 0.0238 mmol) in 1 ml of H$_2$O was added. The reaction mixture was stirred at room temperature for 3 hours, until no starting material was detectable (TLC and HPLC analysis). The solvents were removed under reduced pressure and the crude red solid (2S,4S)-2, 5,12-trihydroxy-7-methoxy-4-{[[(1S,3R,4 aS, 9S,9aR,10aS)-9-methoxy-1-methyloctahydro-1H-pyrano[4',3':4,5][1,3] oxazolo[2,3-c][1,4]oxazin-3-yl]oxy}-6,11-dioxo-1,2,3,4,6, 11-hexahydrotetracene-2-carboxylic acid 51a was used without further purifications in the next step. MS (ESI): 628 [M+H]⁺.

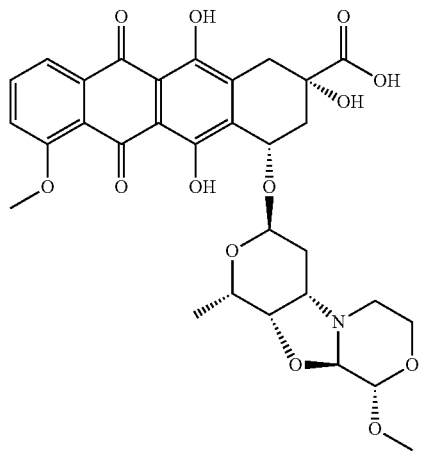

51a

To a solution of the crude intermediate 51a in anhydrous dichloromethane under argon atmosphere, was added anhydrous triethylamine, TBTU (O-(Benzotriazol-1-yl)-N,N,N',N'-tetramethyluronium tetrafluoroborate, also called: N,N,N',N'-Tetramethyl-O-(benzotriazol-1-yl)uronium tetrafluoroborate, CAS No. 125700-67-6, Sigma-Aldrich B-2903), and N-hydroxysuccinimide to form the intermediate NHS ester of 51a. Alternatively, other coupling reagents such as DCC or EDC can be used. After one hour, 2-(pyridin-2-yl disulfanyl)ethanamine hydrochloride (CAS No. 106139-15-5) was added. The reaction mixture was stirred at room temperature for 30 min, until disappearance of the starting material (HPLC-MS analysis). The solvent was evaporated under vacuum and the residue was then purified by flash column chromatography on silica gel, affording 51. MS (ESI): 796.88 [M+H]⁺.

LD-52: Synthesis of 2-(2-pyridyldisulfanyl)ethyl N-[2-[[2-[(2S,4S)-4-[[(1S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-6,11-dioxo-3,4-dihydro-1H-tetracen-2-yl]-2-oxo-ethoxy]carbonyl-methyl-amino]ethyl]-N-methyl-carbamate

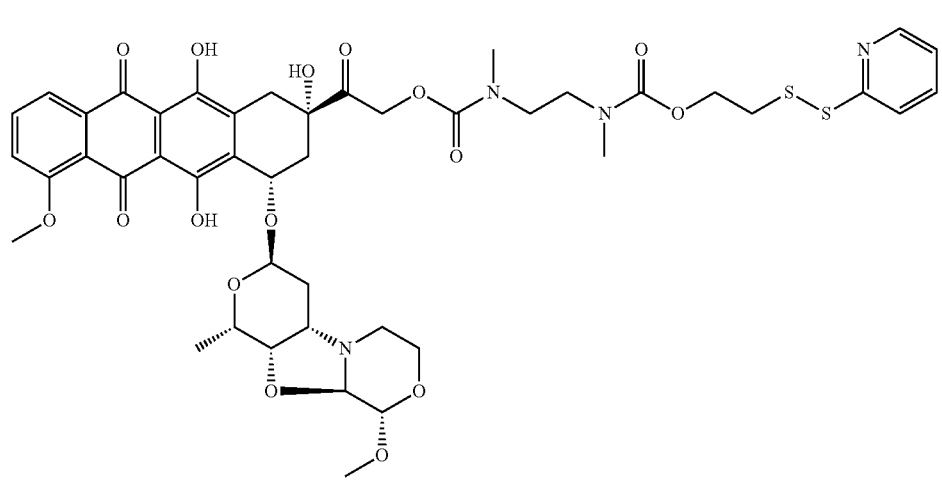

LD-52

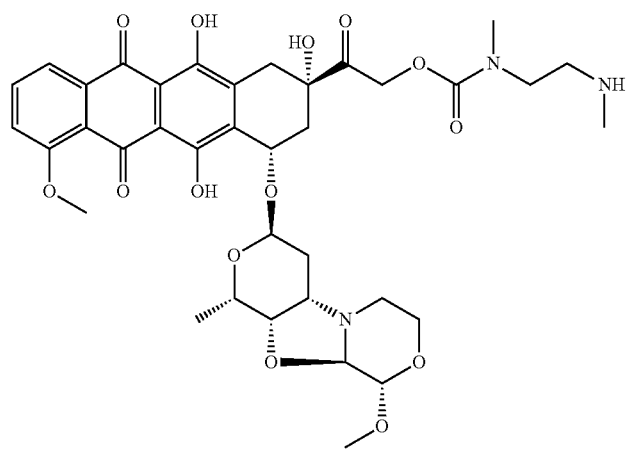

52a

[2-[(2S,4 S)-4-[[(1 S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-6,11-dioxo-3,4-dihydro-1H-tetracen-2-yl]-2-oxo-ethyl] N-methyl-N-[2-(methylamino)ethyl]carbamate 52a was prepared from PNU-159682, with triphosgene ($Cl_3CO)_2C$=O, and N1,N2-dimethylethane-1,2-diamine.

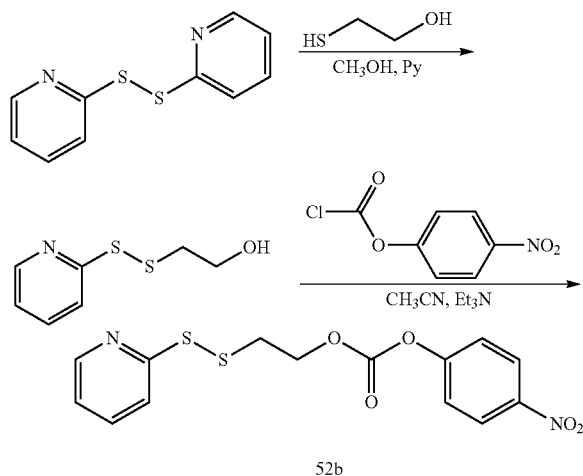

52b 1,2-Di(pyridin-2-yl)disulfane and 2-mercaptoethanol were reacted in pyridine and methanol at room temperature to give 2-(pyridin-2-yldisulfanyl)ethanol. Acylation with 4-nitrophenyl carbonochloridate in triethylamine and acetonitrile gave 4-nitrophenyl 2-(pyridin-2-yldisulfanyl) ethyl carbonate 52b. Intermediate 52a was reacted with 52b to form LD-52.

LD-53: Synthesis of [2-methyl-2-(2-pyridyldisulfanyl)propyl]N-[2-[[2-[(2S,4 S)-4-[[(1 S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-6,11-dioxo-3,4-dihydro-1H-tetracen-2-yl]-2-oxo-ethoxy]carbonyl-methyl-amino]ethyl]-N-methyl-carbamate Following the procedures for LD-52, intermediate 52a was acylated with 2-methyl-2-(pyridin-2-yldisulfanyl)propyl 4-nitrophenyl carbonate to give LD-53.

LD-54: Synthesis of (2S,4S)-4-[[(1S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-N-[2-methyl-2-(2-pyridyldisulfanyl)propyl]-6,11-dioxo-3,4-dihydro-1H-tetracene-2-carboxamide Following the procedures for LD-51, crude intermediate 51a in anhydrous dichloromethane under argon atmosphere, was reacted with anhydrous triethylamine, TBTU, and 2-methyl-2-(pyridin-2-yldisulfanyl)propan-1-amine to afford LD-54.

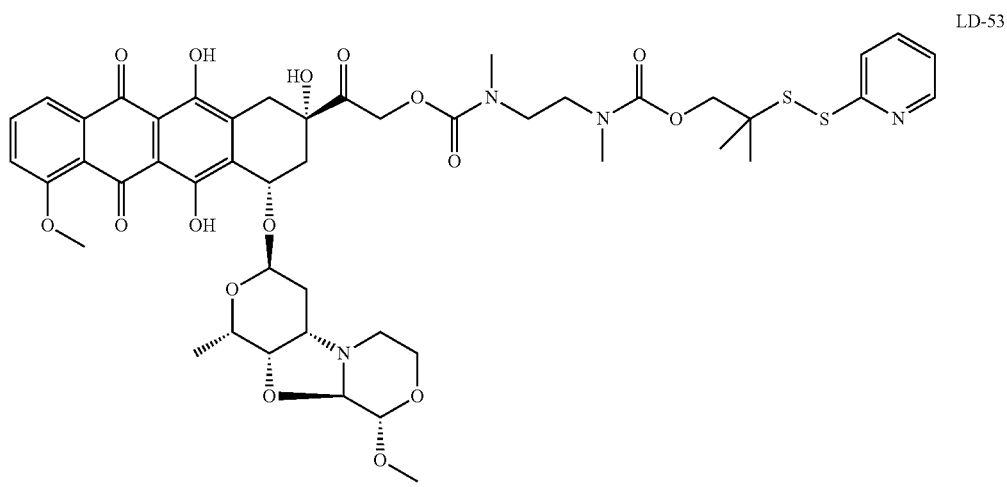 [SMILES: COc1cccc2c1C(=O)c1c(O)c3c(c(O)c1C2=O)C[C@@](O)(C(=O)COC(=O)N(C)CCN(C)C(=O)OCC(C)(C)SSc1ccccn1)C[C@@H]3O[C@H]1C[C@H]2[C@H](O[C@@H]3[C@@H](OC)OCCN32)[C@H](C)O1]

LD-55: Synthesis of (2S,4S)-4-[[(1S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-N-[2-methyl-2-[(5-nitro-2-pyridyl)disulfanyl]propyl]-6,11-dioxo-3,4-dihydro-1H-tetracene-2-carboxamide LD-57: Synthesis of (2S,4S)-4-[[(1S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-N-[2-[(5-nitro-2-pyridyl)disulfanyl]ethyl]-6,11-dioxo-3,4-dihydro-1H-tetracene-2-carboxamide

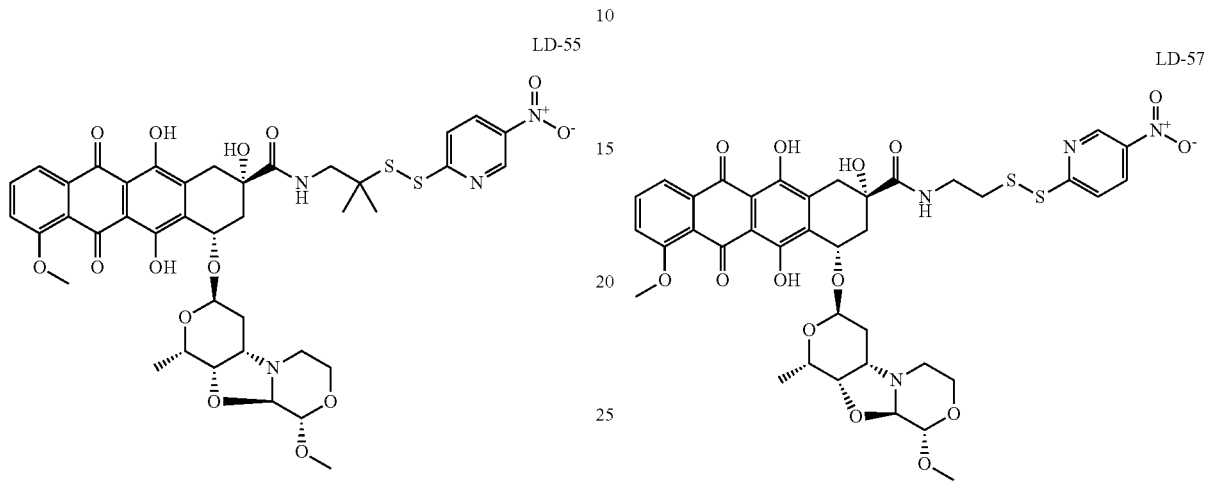

Following the procedures for LD-60, 5-nitropyridine-2-thiol 60a was added to a solution of LD-54 in DMF to give LD-55.

LD-56: Synthesis of 2-(2-pyridyldisulfanyl)propyl N-methyl-N-[2-[methyl-[2-oxo-2-[2,5,12-trihydroxy-7-methoxy-4-[(9-methoxy-1-methyl-3,4,4a,6,7,9,9a,10a-octahydro-1H-pyrano[1,2]oxazolo[3,4-b][1,4]oxazin-3-yl)oxy]-6,11-dioxo-3,4-dihydro-1H-tetracen-2-yl]ethoxy]carbonyl-amino]ethyl] carbamate To a mixture of 1,2-bis(5-nitropyridin-2-yl)disulfane 57a (1.0 g, 3.22 mmol) in anhydrous DMF/MeOH (25 mL/25 mL) was added HOAc (0.1 mL), followed by 2-aminoethanethiol hydrochloride 57b (183 mg, 1.61 mmol). After the reaction mixture was stirred at r.t. overnight, it was concentrated under vacuum to remove the solvent, and the residue was washed with DCM (30 mL×4) to afford 2-((5-nitropyridin-2-yl)disulfanyl)ethanamine hydrochloride 57c as pale yellow solid (300 mg, 69.6%). $^1$H NMR (400 MHz, DMSO-

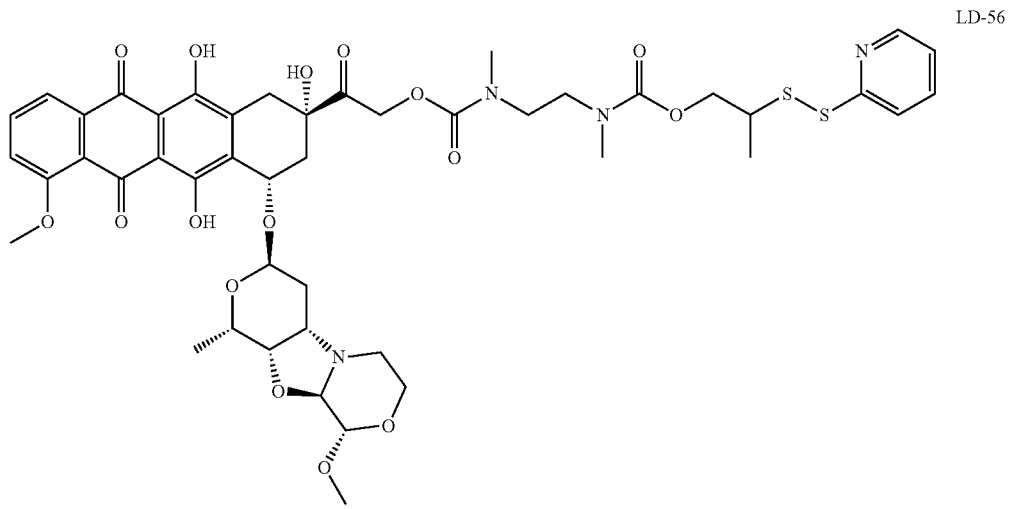 [SMILES: COc1cccc2c1C(=O)c1c(O)c3c(c(O)c1C2=O)C[C@@](O)(C(=O)COC(=O)N(C)CCN(C)C(=O)OCC(C)SSc1ccccn1)C[C@@H]3O[C@H]1C[C@H]2[C@H](O[C@@H]3[C@@H](OC)OCCN32)[C@H](C)O1]

Following the procedures for LD-52, intermediate 52a was acylated with 4-nitrophenyl 2-(pyridin-2-yldisulfanyl) propyl carbonate to give LD-56.

$d_6$) δ 9.28 (d, J=2.4 Hz, 1H), 8.56 (dd, J=8.8, 2.4 Hz, 1H), 8.24 (s, 4H), 8.03 (d, J=8.8 Hz, 1H), 3.15-3.13 (m, 2H), 3.08-3.06 (m, 2H)

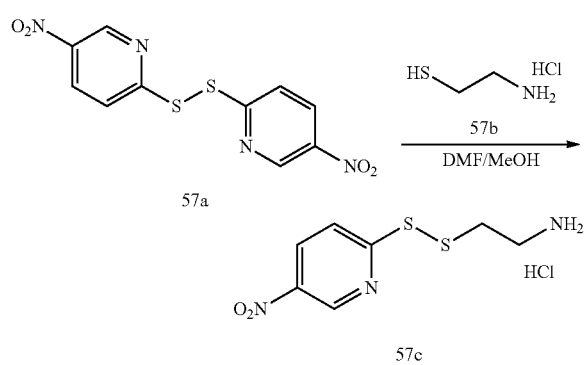

Intermediate 51a was prepared as above. Alternatively, to a suspension of PNU-159682 (50 mg, 0.078 mmol) in MeOH/H₂O (5 mL/5 mL) was added a solution of NaIO₄ (17 mg, 0.078 mmol) in H₂O (2 mL). The heterogeneous reaction mixture was vigorously stirred at r.t. for 4 h in the dark. Then the mixture was concentrated under vacuum, and the residue was purified by column chromatography on silica gel (DCM/MeOH=100/1 to 10/1) to afford intermediate 51a as purple solid (40 mg, 80%).

To a solution of intermediate 51a (40 mg, 0.064 mmol) in anhydrous DCM (5 mL) was added DIEA (41 mg, 0.32 mmol) and HATU (is O-(7-azabenzotriazol-1-yl)-N,N,N', N'-tetramethyluronium hexafluorophosphate, 73 mg, 0.19 mmol). After the mixture was stirred at r.t. for 0.5 h, intermediate 57c (51 mg, 0.19 mmol) was added. The resulting mixture was stirred at r.t. for another 4 h. The mixture was purified by prep-TLC (DCM/MeOH=20/1) to afford LD-57 as purple solid (18 mg, 33.3%). LCMS (ESI): RT=0.890 min, M+H⁺=841.2., Method=5-95AB/1.5 min. ¹H NMR (400 MHz, CDCl₃) δ 13.94 (s, 1H), 13.30 (s, 1H), 9.33 (d, J=2.0 Hz, 1H), 8.40 (dd, J=9.2, 2.4 Hz, 1H), 8.22 (t, J=6.0 Hz, 1H), 8.04 (J=7.6 Hz, 1H), 7.80-7.76 (m, 2H), 7.40 (d, J=8.8 Hz, 1H), 5.52 (d, J=5.6 Hz, 1H), 5.34 (s, 1H), 5.30 (s, 1H), 5.22 (s, 1H), 4.69 (d, J=1.6 Hz, 1H), 4.47 (d, J=0.8 Hz, 1H), 4.10 (s, 3H), 4.07-4.01 (m, 2H), 3.91 (t, J=9.6 Hz, 1H), 3.74 (s, 2H), 3.70-3.55 (m, 4H), 3.45 (s, 3H), 3.41-3.38 (m, 1H), 3.25 (d, J=2.4 Hz, 2H), 3.05 (t, J=6.0 Hz, 2H), 2.83-2.80 (m, 1H), 2.73-2.68 (m, 1H), 2.52-2.48 (m, 1H), 2.41-2.36 (m, 1H), 2.05-1.98 (s, 1H), 1.81-1.75 (m, 1H), 1.36 (d, J=6.0 Hz, 3H)

LD-58: Synthesis of 2-[(5-nitro-2-pyridyl)disulfanyl]ethyl N-[2-[[2-[(2S,4S)-4-[[(1S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-6,11-dioxo-3,4-dihydro-1H-tetracen-2-yl]-2-oxo-ethoxy]carbonyl-methyl-amino]ethyl]-N-methyl-carbamate

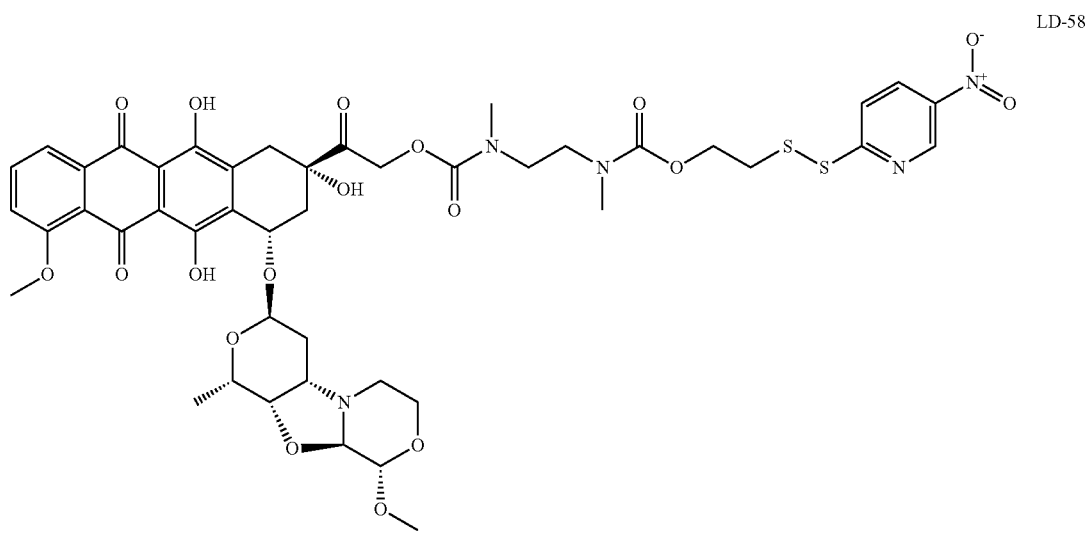 [SMILES: COc1cccc2c1C(=O)c1c(O)c3c(c(O)c1C2=O)C[C@@](O)(C(=O)COC(=O)N(C)CCN(C)C(=O)OCCSSc1ccc([N+](=O)[O-])cn1)C[C@@H]3O[C@H]1C[C@H]2[C@H](O[C@@H]3[C@@H](OC)OCCN32)[C@H](C)O1]

A solution of 1,2-bis(5-nitropyridin-2-yl)disulfane 57a (9.6 g, 30.97 mmol) and 2-mercaptoethanol (1.21 g, 15.49 mmol) in anhydrous DCM/CH₃OH (250 mL/250 mL) was stirred at r.t. under N2 for 24 h. After the mixture was concentrated under vacuum, and the residue was diluted with DCM (300 mL). MnO₂ (10 g) was added and the mixture was stirred at r.t. for another 0.5 h. The mixture was purified by column chromatography on silica gel (DCM/MeOH=100/1 to 100/1) to afford 2-((5-nitropyridin-2-yl)disulfanyl)ethanol 58a (2.2 g, 61.1%) as brown oil. ¹H NMR (400 MHz, CDCl₃) δ 9.33 (d, J=2.8 Hz, 1H), 8.38-8.35 (dd, J=9.2, 2.8 Hz, 1H), 7.67 (d, J=9.2 Hz, 1H), 4.10 (t, J=7.2 Hz, 1H), 3.81-3.76 (q, 2H), 3.01 (t, J=5.2 Hz, 2H).

To a solution of 58a (500 mg, 2.15 mmol) in anhydrous DMF (10 mL) was added DIEA (834 mg, 6.45 mmol), followed by PNP carbonate (bis(4-nitrophenyl) carbonate, 1.31 g, 4.31 mmol). The reaction solution was stirred at r.t for 4 h and the mixture was purified by prep-HPLC (FA) to afford 4-nitrophenyl 2-((5-nitropyridin-2-yl)disulfanyl)ethyl carbonate 58b (270 mg, 33.1%) as light brown oil. ¹H NMR (400 MHz, CDCl₃) δ 9.30 (d, J=2.4 Hz, 1H), 8.43-8.40 (dd, J=8.8, 2.4 Hz, 1H), 8.30-8.28 (m, 2H), 7.87 (d, J=8.8 Hz, 1H), 7.39-7.37 (m, 2H), 4.56 (t, J=6.4 Hz, 2H), 3.21 (t, J=6.4 Hz, 2H).

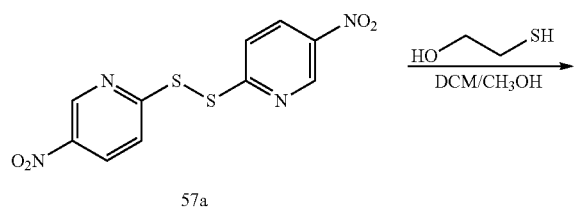

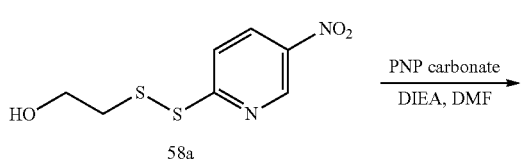

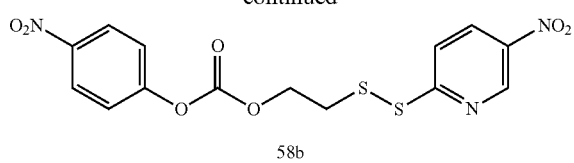

[2-[(2S,4S)-4-[[(1S,3R,4aS,9S,9aR,10aS)-9-methoxy-1-methyl-3,4,4a,6,7,9,9a,10a-octahydro-1H-pyrano[1,2]oxazolo[3,4-b][1,4]oxazin-3-yl]oxy]-2,5,12-trihydroxy-7-methoxy-6,11-dioxo-3,4-dihydro-1H-tetracen-2-yl]-2-oxo-ethyl] N-methyl-N-[2-(methylamino)ethyl]carbamate 52a was prepared from PNU via deprotection of Bpoc-protected 58c where Bpoc is 2-(p-biphenylyl)-2-propyloxycarbonyl. To a solution of 58c (25 mg, 0.025 mmol), where the amine is protected with 2-(4-biphenylyl)-prop-2-yl 4'-methoxycarbonylphenyl carbonate (BPOC reagent, Sigma-Aldrich, CAS Reg. No. 31140-37-1) in anhydrous DCM (4 mL) was added a solution of dichloroacetic acid (Cl$_2$CHCOOH, 65 mg, 0.50 mmol) in anhydrous DCM (1 mL). The reaction solution was stirred at r.t for 2 h. The solution was concentrated under vacuum and the residue was washed with methyl, tert-butyl ether (MTBE, 10 mL×2) to afford 52a (25 mg, 100%) as red solid.

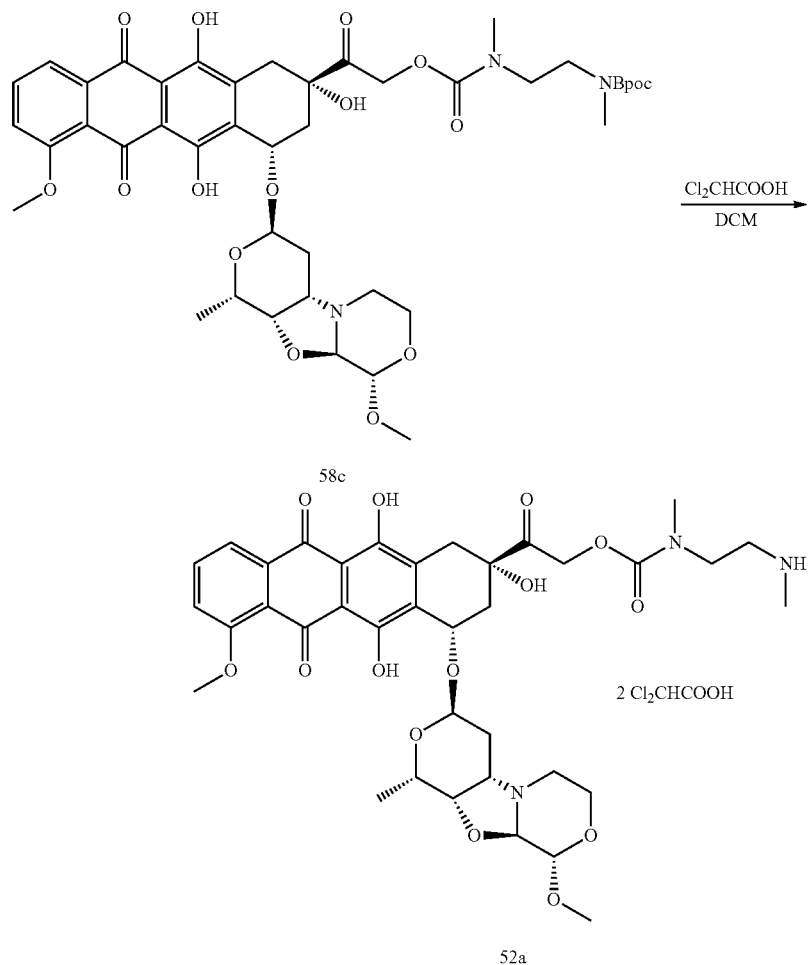

To a solution of 52a (25 mg, 0.025 mmol) and 4-nitrophenyl 2-((5-nitropyridin-2-yl)disulfanyl)ethyl carbonate 58b (30 mg, 0.075 mmol) in anhydrous DMF (3 mL) was added TEA (triethylamine, 25 mg, 0.25 mmol). After the solution was stirred at r.t. overnight, it was concentrated under vacuum and the residue was purified by prep-TLC (DCM/MeOH=20/1) to afford LD-58 (12 mg, 48.0%) as red solid.
LCMS (ESI): RT=0.921 min, M+Na$^+$=1036.2. $^1$H NMR (400 MHz, CDCl$_3$) δ 13.88 (s, 1H), 13.24 (d, J=4.0 Hz, 1H), 9.26-9.25 (m, 1H), 8.40 (d, J=6.0 Hz, 1H), 8.01 (d, J=7.6 Hz, 1H), 7.89 (d, J=8.8 Hz, 1H), 7.77 (t, J=8.0 Hz, 1H), 7.38 (d, J=8.4 Hz, 1H), 5.47 (s, 1H), 5.30-5.23 (m, 2H), 5.15-5.11 (m, 1H), 4.92-4.87 (m, 1H), 4.70 (s, 1H), 4.47 (s, 1H), 4.35 (s, 2H), 4.10-4.03 (m, 4H), 3.92-3.87 (m, 1H), 3.59-3.40 (m, 8H), 3.25-3.22 (m, 1H), 3.12-3.10 (m, 2H), 3.04 (s, 2H), 3.98 (t, J=8.8 Hz, 4H), 2.84-2.82 (m, 2H), 2.60 (d, J=14.8 Hz, 1H), 2.07-1.98 (m, 1H), 1.76-1.72 (m, 1H), 1.41 (d, J=5.6 Hz, 3H).

LD-59: Synthesis of 2,5,12-trihydroxy-7-methoxy-4-[(9-methoxy-1-methyl-3,4,4a,6,7,9,9a,10a-octahydro-1H-pyrano[1,2]oxazolo[3,4-b][1,4]oxazin-3-yl)oxy]-N-[2-[(5-nitro-2-pyridyl)disulfanyl]propyl]-6,11-dioxo-3,4-dihydro-1H-tetracene-2-carboxamide

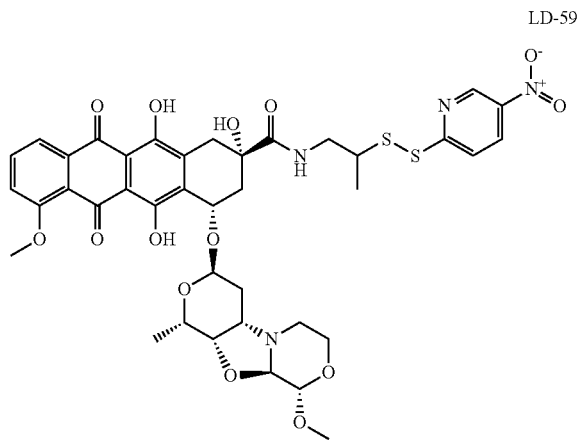 [SMILES: COc1cccc2c1C(=O)c1c(O)c3c(c(O)c1C2=O)C[C@@](O)(C(=O)NCC(C)SSc1ccc([N+](=O)[O-])cn1)C[C@@H]3O[C@H]1C[C@H]2[C@H](O[C@@H]3[C@@H](OC)OCCN32)[C@H](C)O1]

LD-59

To a stirred solution of 1-aminopropan-2-ol 59a (10 g, 133 mmol) in MeOH (360 mL) and H$_2$O (40 mL) was added Boc$_2$O (37 g, 169 mmol). After the reaction mixture was stirred at r.t. for 5 h, it was concentrated and purified by chromatography (EtOAc/PE=10%-50%) to give tert-butyl 2-hydroxypropylcarbamate 59b as a colorless oil (19.8 g, yield: 85%).

To a stirred solution of 59b (10 g, 57 mmol) and Et$_3$N (17 g, 171 mmol) in DCM (130 mL) was added a solution of MSCl (methanesulfonyl chloride, 13 g, 114 mmol). After the reaction mixture was stirred at r.t. for 4 h, it was washed with ice water (200 mL×3) and brine (200 mL). The organic layer was concentrated to give 1-(tert-butoxycarbonylamino)propan-2-yl methanesulfonate 59c as a red oil (12 g, yield: 83%).

To a stirred solution of 59c (6 g, 23.7 mmol) in acetone (70 mL) was added a solution of potassium thioacetate (potassium ethanethioate, 5.4 g, 47.3 mmol) in H$_2$O (100 mL). The reaction mixture was stirred at 60° C. for 12 h. The mixture was concentrated and extracted with DCM (200 ml×2). The combined organic layers were concentrated and purified by chromatography to give S-1-(tert-butoxycarbonylamino)propan-2-yl ethanethioate 59d as a red solid (1.1 g, yield: 20%). $^1$H NMR (400 MHz, CDCl3-d) δ 1.30 (d, J=7.09 Hz, 3H) 1.44 (s, 9H) 2.33 (s, 3H) 3.16-3.42 (m, 2H) 3.58-3.71 (m, 1H)

To a stirred solution of 59d (500 mg, 2.15 mmol) in MeOH (5 mL) was added HCl/MeOH (10 mL) dropwise. After the reaction mixture was stirred at r.t. for 3 h, it was concentrated to give 1-aminopropane-2-thiol hydrochloride 59e, used directly in the next step.

To a solution of 57a (1.33 g, 4.3 mmol) in DCM (35 mL) was added a solution of 59e (273 mg, 2.15 mmol). The mixture was stirred at 15° C. for 12 h. MnO$_2$ (374.1 mg, 4.3 mmol) was added to the mixture and stirred at 15° C. for 10 min. The solid was washed with DCM (100 mL) and MeOH (30 mL×3). The solution was concentrated to give 2-((5-nitropyridin-2-yl)disulfanyl)propan-1-amine 59f as a yellow solid (300 mg, 57%). LCMS (ESI): RT=0.546 min, M+H$^+$=245.7.

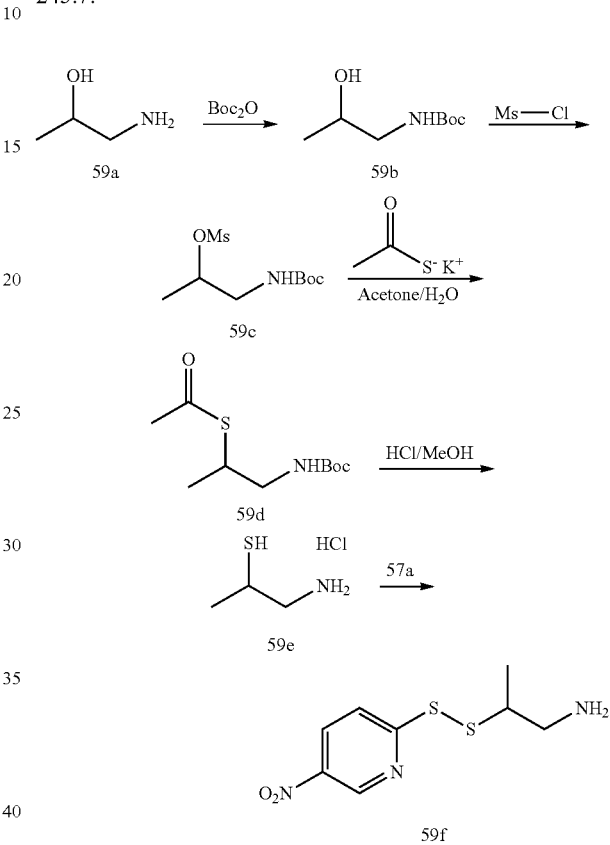

To a solution of intermediate 51a (25 mg, 0.040 mmol) in anhydrous DCM/DMF (5 mL) was added DIEA (diisopropylethylamine, 26 mg, 0.20 mmol) and HATU (is O-(7-azabenzotriazol-1-yl)-N,N,N',N'-tetramethyluronium hexafluorophosphate, 46 mg, 0.12 mmol). After the mixture was stirred at r.t for 0.5 h, 59f (34 mg, 0.12 mmol) was added. The resulting mixture was stirred at r.t for another 4 h. The mixture was diluted with DCM (30 mL), and washed with brine (15 mL×3). The DCM layer was dried (Na$_2$SO$_4$), filtered, and concentrate. The residue was purified by prep-TLC (DCM/MeOH=20/1) to afford LD-59 (7 mg, 20.6%) as purple solid. LCMS (ESI): RT=0.783 min, M+H$^+$=855.2. $^1$H NMR (400 MHz, CDCl$_3$) δ 13.94 (d, J=3.6 Hz, 1H), 13.32 (d, J=4.8 Hz, 1H), 9.33 (s, 1H), 8.63-8.47 (m, 1H), 8.39-8.35 (m, 1H), 8.04 (d, J=7.6 Hz, 1H), 7.78 (J=8.0 Hz, 1H), 7.74-7.71 (dd, J=8.8, 5.6 Hz, 1H), 7.39 (d, J=8.8 Hz, 1H), 5.52 (d, J=5.2 Hz, 1H), 5.35 (s, 1H), 5.27 (d, J=4.8 Hz, 1H), 4.68 (d, J=4.4 Hz, 1H), 4.46 (d, J=8.0 Hz, 1H), 4.10 (s, 3H), 4.06 (d, J=7.6 Hz, 1H), 3.92 (t, J=7.8 Hz, 2H), 3.71-3.67 (m, 1H), 3.59-3.55 (m, 2H), 3.45 (d, J=6.4 Hz, 3H), 3.41-3.36 (m, 1H), 3.28-3.22 (m, 3H), 2.84-2.60 (m, 2H), 2.53-2.37 (m, 2H), 2.06-1.94 (m, 1H), 1.81-1.77 (m, 1H), 1.40-1.38 (dd, J=6.4, 2.4 Hz, 3H), 1.35 (t, J=6.0 Hz, 3H)

LD-60: Synthesis of [2-oxo-2-[2,5,12-trihydroxy-7-methoxy-4-[(9-methoxy-1-methyl-3,4,4a,6,7,9,9a,10a-octahydro-1H-pyrano[1,2]oxazolo[3,4-b][1,4]oxazin-3-yl)oxy]-6,11-dioxo-3,4-dihydro-1H-tetracen-2-yl]ethyl] N-methyl-N-[2-[methyl-[2-[(5-nitro-2-pyridyl)disulfanyl]propoxycarbonyl]amino]ethyl]carbamate

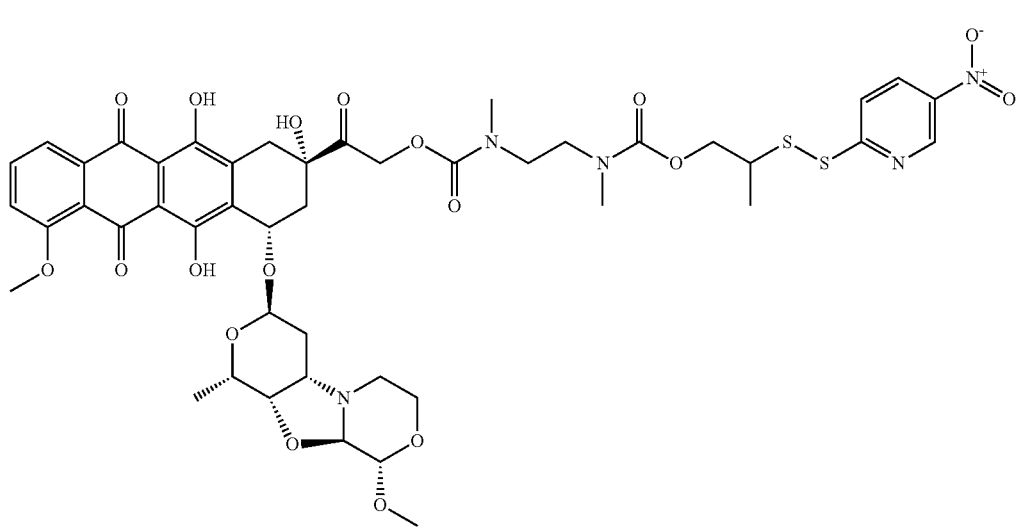

To a solution of 2-(2-pyridyldisulfanyl)propyl N-methyl-N-[2-[methyl-[2-oxo-2-[2,5,12-trihydroxy-7-methoxy-4-[(9-methoxy-1-methyl-3,4,4a,6,7,9,9a,10a-octahydro-1H-pyrano[1,2]oxazolo[3,4-b][1,4]oxazin-3-yl)oxy]-6,11-dioxo-3,4-dihydro-1H-tetracen-2-yl]ethoxy]carbonyl-amino]ethyl]carbamate LD-56 (10 mg, 10.17 umol) in DMF (1 mL) was added a solution of 5-nitropyridine-2-thiol 60a (15.89 mg, 101.72 umol) at 20° C. The reaction mixture was stirred at 20° C. for 2 h. The reaction mixture was diluted with DCM (10 mL) and then washed with water (5 mL), aq.NaHCO$_3$ (5 mL) and brine (5 mL). The organic layer was dried and concentrated. The residue was purified by prep-TLC (DCM:MeOH=25:1) to give pure LD-60 (7 mg, 66.94%) as a red solid. LCMS: (10-80, CD, 7.0 min), 3.782 min, Ms=1028.2 (M+1); $^1$H NMR (400 MHz, CDCl$_3$) δ 13.83 (s, 1H), 13.19 (s, 1H), 9.18 (s, 1H), 8.31 (d, 1H, J=7.6 Hz), 7.97 (d, 1H, J=8.0 Hz), 7.86 (d, 1H, J=8.4 Hz), 7.73 (t, 1H, J=8.4 Hz), 7.33 (d, 1H, J=8.4 Hz), 5.41 (s, 1H), 5.29-5.05 (m, 3H), 4.89-4.75 (m, 1H), 4.64 (s, 1H), 4.40 (s, 1H), 4.13 (s, 2H), 4.09-3.80 (m, 6H), 3.58-3.12 (m, 12H), 3.05-2.85 (m, 7H), 2.78-2.42 (m, 3H), 2.12-1.85 (m, 2H), 1.72-1.55 (m, 1H), 1.38-1.25 (m, 6H)

LD-61: Synthesis of 2,5,12-trihydroxy-7-methoxy-4-[(9-methoxy-1-methyl-3,4,4a,6,7,9,9a,10a-octahydro-1H-pyrano[1,2]oxazolo[3,4-b][1,4]oxazin-3-yl)oxy]-6,11-dioxo-N-[2-(2-pyridyldisulfanyl)propyl]-3,4-dihydro-1H-tetracene-2-carboxamide

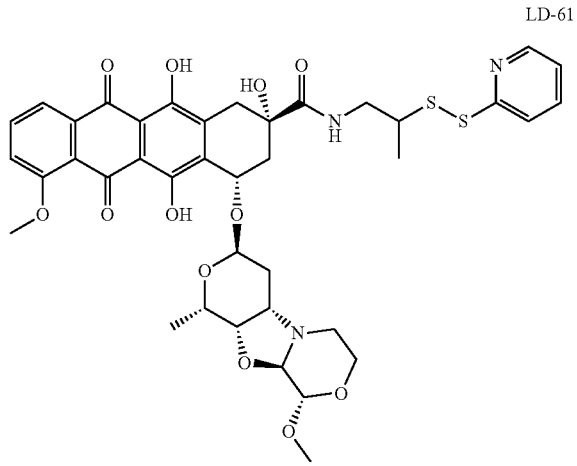 [SMILES: COc1cccc2c1C(=O)c1c(O)c3c(c(O)c1C2=O)C[C@@](O)(C(=O)NCC(C)SSc1ccccn1)C[C@@H]3O[C@H]1C[C@H]2[C@H](O[C@@H]3[C@@H](OC)OCCN32)[C@H](C)O1]

Following the procedures for LD-51, crude intermediate 51a in anhydrous dichloromethane under argon atmosphere, was reacted with anhydrous triethylamine, TBTU, and 2-(pyridin-2-yldisulfanyl)propan-1-amine to afford LD-61.

LD-62: Synthesis of (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N—((R)-2-((5-nitropyridin-2-yl)disulfanyl)propyl)-6,11-dioxo-1,2,3,4,6,11-hexahydrotetracene-2-carboxamide Following the procedures for LD-59, LD-62 was prepared.

LD-63: Synthesis of (2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-N—((S)-2-((5-nitropyridin-2-yl)disulfanyl)propyl)-6,11-dioxo-1,2,3,4,6,11-hexahydrotetracene-2-carboxamide Following the procedures for LD-59, LD-63 was prepared.

Example 2 Preparation of Cysteine Engineered Antibodies for Conjugation by Reduction and Reoxidation Under certain conditions, the cysteine engineered antibodies may be made reactive for conjugation with linker-drug intermediates of the invention, such as those in Table 1, by treatment with a reducing agent such as DTT (Cleland's reagent, dithiothreitol) or TCEP (tris(2-carboxyethyl) phosphine hydrochloride; Getz et al (1999) Anal. Biochem. Vol 273:73-80; Soltec Ventures, Beverly, Mass.) in 50 mM Tris pH 7.5 with 2 mM EDTA for 3 hrs at 37° C. or overnight at room temperature. Full length, cysteine engineered monoclonal antibodies (THIOMAB™) expressed in CHO cells (Gomez et al (2010) Biotechnology and Bioeng. 105(4): 748-760; Gomez et al (2010) Biotechnol. Prog. 26:1438-1445) were reduced, for example with about a 50 fold excess of DTT overnight at room temperature to reduce disulfide bonds which may form between the newly introduced cysteine residues and the cysteine present in the culture media. The reduced THIOMAB™ was diluted and loaded onto a HiTrap S column in 10 mM sodium acetate, pH 5, and eluted with PBS containing 0.3M sodium chloride. Alternatively, the antibody was acidified by addition of $\frac{1}{20}^{th}$ volume of 10% acetic acid, diluted with 10 mM succinate pH 5, loaded onto the column and then washed with 10 column volumes of succinate buffer. The column was eluted with 50 mM Tris pH7.5, 2 mM EDTA.

Light chain amino acids are numbered according to Kabat (Kabat et al., *Sequences of proteins of immunological interest*, (1991) 5th Ed., US Dept of Health and Human Service, National Institutes of Health, Bethesda, Md.). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (THIOMAB™) expressed in CHO cells bear cysteine adducts (cystines) or glutathionylated on the engineered cysteines due to cell culture conditions. To liberate the reactive thiol groups of the engineered cysteines, the THIOMAB™ are dissolved in 500 mM sodium borate and 500 mM sodium chloride at about pH 8.0 and reduced with about a 50-100 fold excess of 1 mM TCEP (tris(2-carboxyethyl) phosphine hydrochloride (Getz et al (1999) Anal. Biochem. Vol 273:73-80; Soltec Ventures, Beverly, Mass.) for about 1-2 hrs at 37° C. Alternatively, DTT can be used as reducing agent. The formation of inter-chain disulfide bonds was monitored either by non-reducing SDS-PAGE or by denaturing reverse phase HPLC PLRP column chromatography. The reduced THIOMAB™ is diluted and loaded onto a HiTrap SP FF column in 10 mM sodium acetate, pH 5, and eluted with PBS containing 0.3M sodium chloride, or 50 mM Tris-Cl, pH 7.5 containing 150 mM sodium chloride.

Disulfide bonds were reestablished between cysteine residues present in the parent Mab by carrying out reoxidation. The eluted reduced THIOMAB™ is treated with 15× or 2 mM dehydroascorbic acid (dhAA) at pH 7 for about 3 hours or for about 3 hrs in 50 mM Tris-Cl, pH 7.5, or with 200 nM to 2 mM aqueous copper sulfate ($CuSO_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Liquid chromatography/Mass Spectrometric Analysis was performed on a TSQ Quantum Triple Quadrupole™ mass spectrometer with extended mass range (Thermo Electron, San Jose Calif.). Samples were chromatographed on a PRLP-S®, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluent was directly ionized using the electrospray source. Data were collected by the Xcalibur® data system and deconvolution was performed using ProMass® (Novatia, LLC, New Jersey). Prior to LC/MS analysis, antibodies or drug conjugates (50 micrograms) were treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 micron particle size, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody.

Example 3 Conjugation of Linker-Drug Intermediates to Antibodies

After the reduction and reoxidation procedures of Example 2, the cysteine-engineered antibody (THIOMAB™) is dissolved in PBS (phosphate buffered saline) buffer and chilled on ice. An excess, from about 1.5 molar to 20 equivalents of a linker-drug intermediate, including but not limited to LD-51 to LD-61 in Table 1, with a thiol-reactive pyridyl disulfide group, is dissolved in DMSO, diluted in acetonitrile and water, and added to the chilled reduced, reoxidized antibody in PBS. Typically the linker-drug is added from a DMSO stock at a concentration of about 20 mM in 50 mM Tris, pH 8, to the antibody and monitored until the reaction is complete from about 1 to about 24 hours as determined by LC-MS analysis of the reaction mixture. When the reaction is complete, an excess of maleimide is added to quench the reaction and cap any unreacted antibody thiol groups. The conjugation mixture may be loaded and eluted through a HiTrap SP FF column to remove excess drug-linker intermediate and other impurities. The reaction mixture is concentrated by centrifugal ultrafiltration and the cysteine engineered antibody drug conjugate is purified and desalted by elution through G25 resin in PBS, filtered through 0.2 µm filters under sterile conditions, and frozen for storage.

For example, the crude antibody-drug conjugate (ADC) is applied to a cation exchange column after dilution with 20 mM sodium succinate, pH 5. The column was washed with at least 10 column volumes of 20 mM sodium succinate, pH 5, and the antibody was eluted with PBS. The antibody drug conjugates were formulated into 20 mM His/acetate, pH 5, with 240 mM sucrose using gel filtration columns. The antibody-drug conjugates were characterized by UV spectroscopy to determine protein concentration, analytical SEC (size-exclusion chromatography) for aggregation analysis and LC-MS before and after treatment with Lysine C endopeptidase.

Size exclusion chromatography is performed using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis may be performed using an Agilent QTOF 6520 ESI instrument. As an example, the antibody-drug conjugate is treated with 1:500 w/w Endoproteinase Lys C (Promega) in Tris, pH 7.5, for 30 min at 37° C. The resulting cleavage fragments are loaded onto a 1000 Å (Angstrom), 8 µm (micron) PLRP-S (highly cross-linked polystyrene) column heated to 80° C. and eluted with a gradient of 30% B to 40% B in 5 minutes. Mobile phase A was $H_2O$ with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

By these procedures, cysteine engineered, antibody drug conjugates 101-117 of Table 2 were prepared.

Example 4 In Vitro Cell Proliferation Assay

Efficacy of ADC was measured by a cell proliferation assay employing the following protocol (CELLTITER GLO™ Luminescent Cell Viability Assay, Promega Corp. Technical Bulletin TB288; Mendoza et al (2002) Cancer Res. 62:5485-5488):

1. An aliquot of 100 µl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CELLTITER GLO™ Reagent equal to the volume of cell culture medium present in each well was added.
6. The contents were mixed for 2 minutes on an orbital shaker to induce cell lysis.
7 The plate was incubated at room temperature for 10 minutes to stabilize the luminescence signal.
8. Luminescence was recorded and reported in graphs as RLU=relative luminescence units.

Data are plotted as the mean of luminescence for each set of replicates, with standard deviation error bars. The protocol is a modification of the CELLTITER GLO™ Luminescent Cell Media: SK-BR-3 grow in 50/50/10% FBS/glutamine/250 µg/mL G-418 OVCAR-3 grow in RPMI/20% FBS/glutamine Example 5 Tumor Growth Inhibition, In Vivo Efficacy in High Expressing HER2 Transgenic Explant Mice Tumors were established and allowed to grow to 150-200 $mm^3$ in volume (as measured using calipers) before a single treatment on day 0. Tumor volume was measured using calipers according to the formula: V $(mm^3)$=0.5A×$B^2$, where A and B are the long and short diameters, respectively. Mice were euthanized before tumor volume reached 3000 $mm^3$ or when tumors showed signs of impending ulceration. Data collected from each experimental group (10 mice per group) were expressed as mean±SE.

The Fo5 mouse mammary tumor model was employed to evaluate the in vivo efficacy of antibody-drug conjugates of the invention after single dose intravenous injections, and as described previously (Phillips G D L, Li G M, Dugger D L, et al. Targeting HER2-Positive Breast Cancer with Trastuzumab-DM1, an Antibody-Cytotoxic Drug Conjugate. (2008) Cancer Res. 68:9280-90), incorporated by reference herein. Anti-Her2 ADC were tested with the Fo5 model, a transgenic mouse model in which the human HER2 gene is over-expressed in mammary epithelium under transcriptional regulation of the murine mammary tumor virus promoter (MMTV-HER2) as shown in FIGS. 3 and 5. The HER2 over-expression causes spontaneous development of a mammary tumor. The mammary tumor of one of these founder animals (founder #5 [Fo5]) has been propagated in subsequent generations of FVB mice by serial transplantation of tumor fragments (~2×2 mm in size). All studies were conducted in accordance with the Guide for the Care and Use of Laboratory Animals. Each antibody-drug conjugate (single dose) was dosed in nine animals intravenously at the start of the study, and 14 days post-transplant. Initial tumor size was about 200 $mm^3$ volume. Measurements of tumor growth inhibition over time by antibody-drug conjugates of the invention and controls are shown in FIGS. 3-5.

Another mammary fat pad transplant efficacy model may be employed as described (Chen et al. (2007) Cancer Res 67:4924-4932), evaluating tumor volume after a single intravenous dose and using tumors excised from a mouse bearing an intraperitoneal tumor, then serially passaged into the mammary fat pads of recipient mice.

Although the foregoing invention has been described in some detail by way of illustration and example for purposes of clarity of understanding, the descriptions and examples should not be construed as limiting the scope of the invention. All patents, patent applications, and references cited throughout the specification are expressly incorporated by reference.

SEQUENCE LISTING

<160> NUMBER OF SEQ ID NOS: 30

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Ser Gln Ser Ile Val His Ser Val Gly Asn Thr Phe Leu Glu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Gln Gly Ser Gln Phe Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Glu Phe Ser Arg Ser Trp Met Asn
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Arg Ile Tyr Pro Gly Asp Gly Asp Thr Asn Tyr Ser Gly Lys Phe
1               5                   10                  15

Lys Gly

<210> SEQ ID NO 6
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Asp Gly Ser Ser Trp Asp Trp Tyr Phe Asp Val
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Ser Gln Ser Leu Leu His Ser Asn Gly Tyr Asn Tyr Leu Asp
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Gly Val Asn Ser Val Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Gln Ala Leu Gln Thr Pro Trp Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn His Ala Ile Ser
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ile Ile Pro Ile Phe Gly Thr Ala Asn Tyr Ala Gln Lys Phe Gln
1               5                   10                  15
```

Gly

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Trp Ala Asp Val Phe Asp
1               5

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Ser Gln Gly Ile Arg Asn Asp Leu Gly
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ala Ser Ser Leu Gln Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gln His Asn Ser Tyr Pro Trp Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asn Tyr Met Ser
1               5

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ile Tyr Ser Gly Asp Ser Thr Tyr Tyr Ala Asp Ser Val Lys Gly
1               5                   10                  15

<210> SEQ ID NO 20
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 20

Asp Gly Tyr Tyr Val Ser Asp Met Val Val
1               5                   10

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Asn Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
            115

<210> SEQ ID NO 23
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 24
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
50                  55                  60

Gly Arg Phe Thr Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
```

```
                    20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
                100                 105

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
                100                 105                 110

Thr Val Thr Val Ser Ser
        115

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
```

85                  90                  95

Thr Phe Gly Gln Gly Thr Lys Leu Glu Ile Lys
            100                 105

<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ala Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 29
<211> LENGTH: 7
<212> TYPE: PRT
<213> ORGANISM: Homo sapiens

<400> SEQUENCE: 29

Met Ala Glu Ala Ile Thr Tyr
1               5

<210> SEQ ID NO 30
<211> LENGTH: 7
<212> TYPE: PRT
<213> ORGANISM: Homo sapiens

<400> SEQUENCE: 30

Thr Ala Phe Arg Phe Pro Asp
1               5

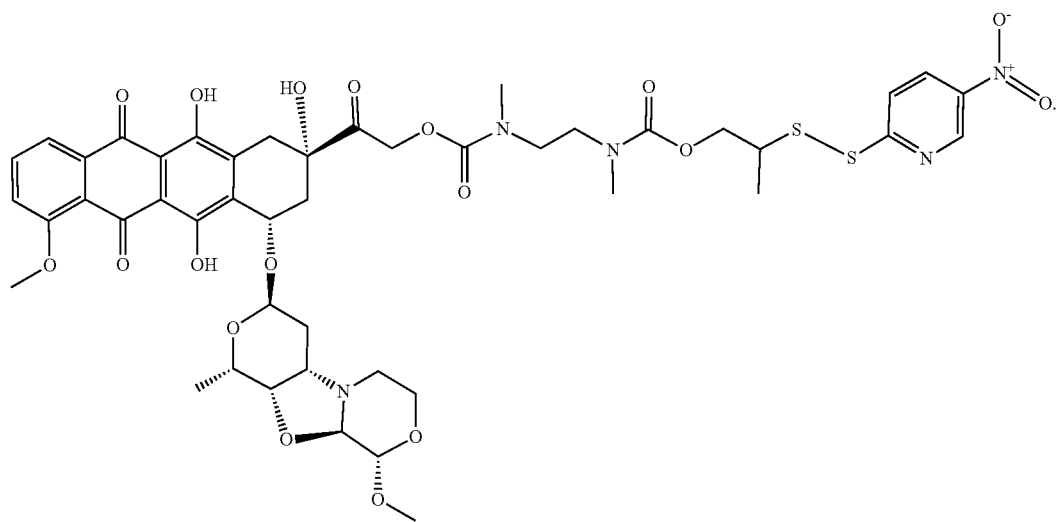
13. The linker-drug intermediate of claim 2 having the structure:
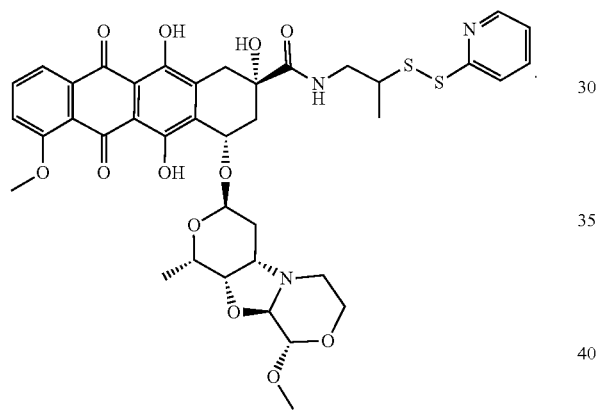
14. The linker-drug intermediate of claim 2 having the structure:
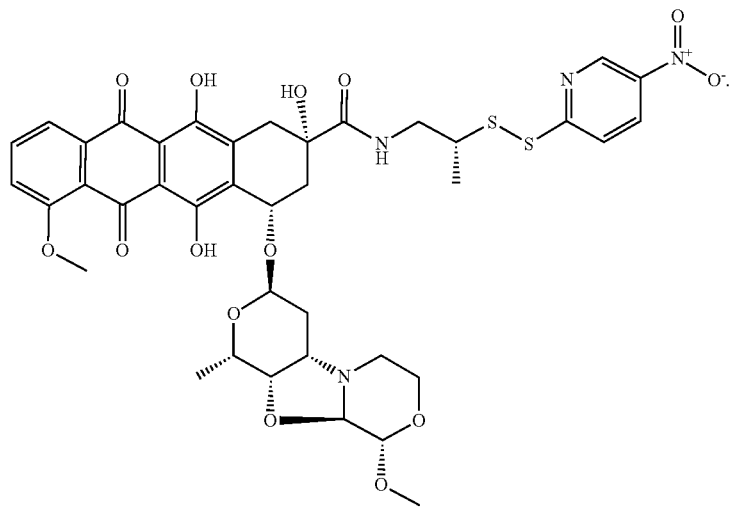

15. The linker-drug intermediate of claim 2 having the structure:
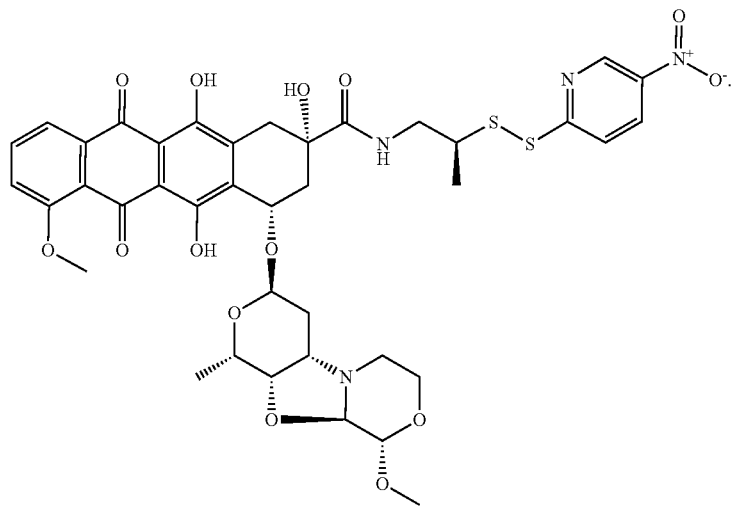

We claim:
1. A linker-drug intermediate having the Formula:

Ant-L-X wherein Ant is selected from the structure:

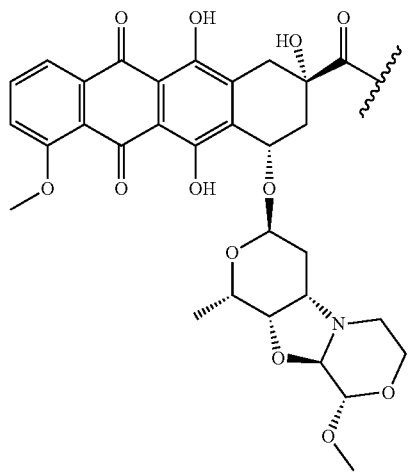 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

where the wavy line indicates the attachment to L;

L is —NH(C$_1$-C$_{12}$ alkylene)-, wherein alkylene is selected from —CH$_2$CH$_2$—, —CH$_2$CH$_2$CH$_2$—, —CH(CH$_3$)CH$_2$—, and —C(CH$_3$)$_2$CH$_2$—;

X is:

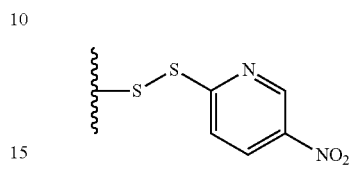

where the wavy line indicates the attachment to L; and alkylene of L is optionally substituted with one or more groups selected from F, Cl, Br, N(CH$_3$)$_2$, NO$_2$, and OCH$_3$.

2. A linker-drug intermediate selected from:

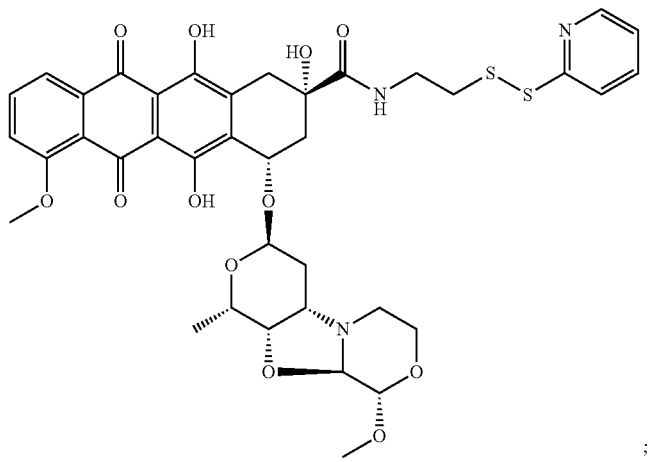 [SMILES: COc1cccc2c1C(=O)c1c(O)c3c(c(O)c1C2=O)C[C@@](O)(C(=O)NCCSSc1ccccn1)C[C@@H]3O[C@H]1C[C@H]2[C@H](O[C@@H]3[C@@H](OC)OCCN32)[C@H](C)O1]

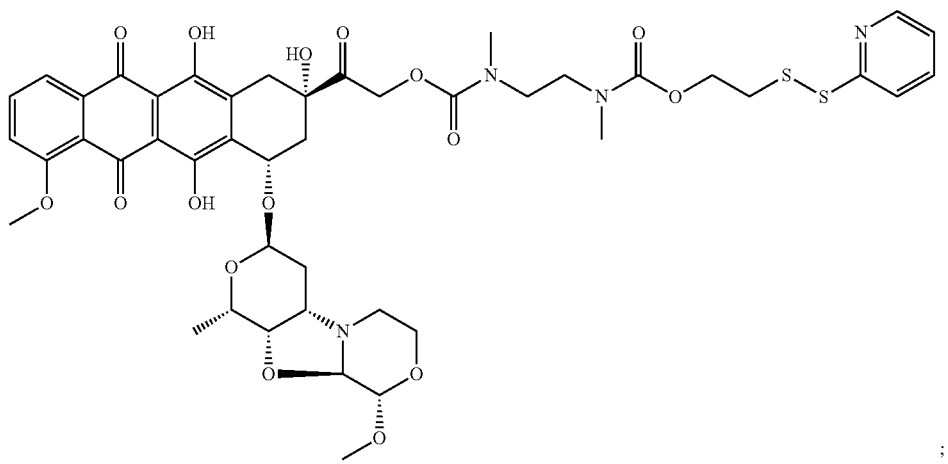

-continued
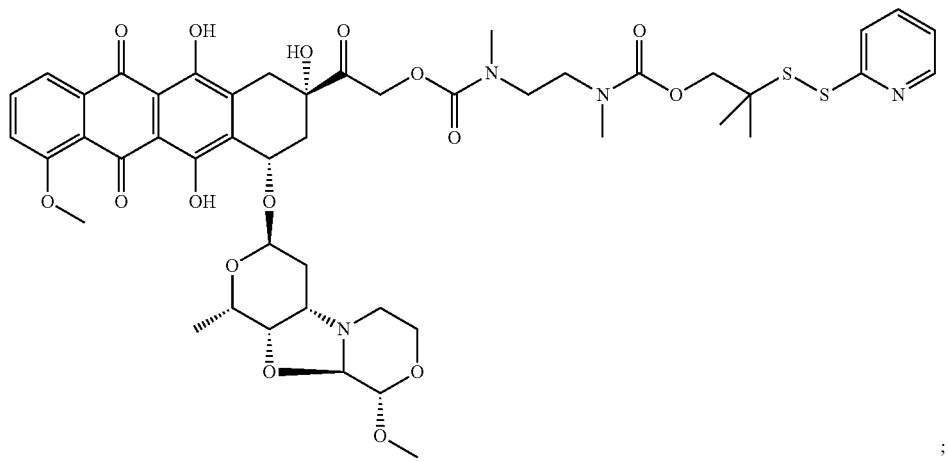
;
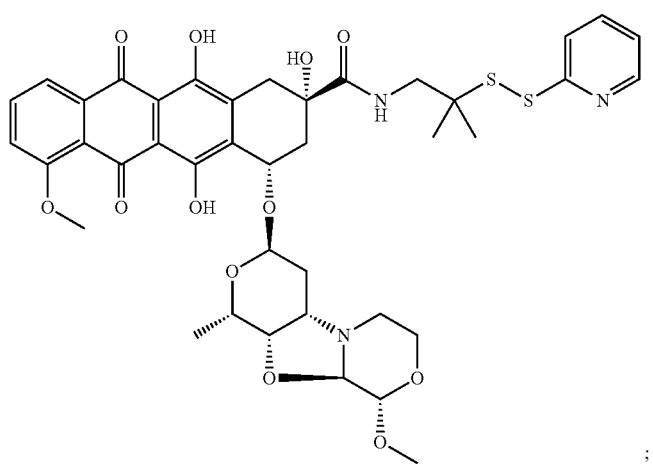
;
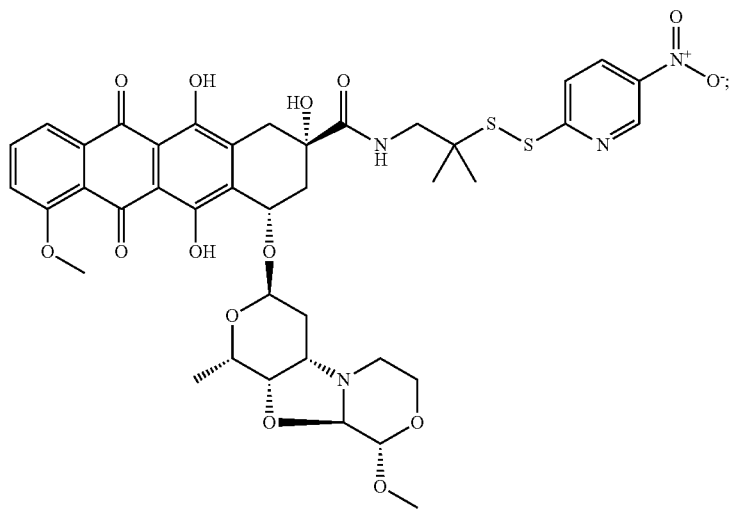

-continued
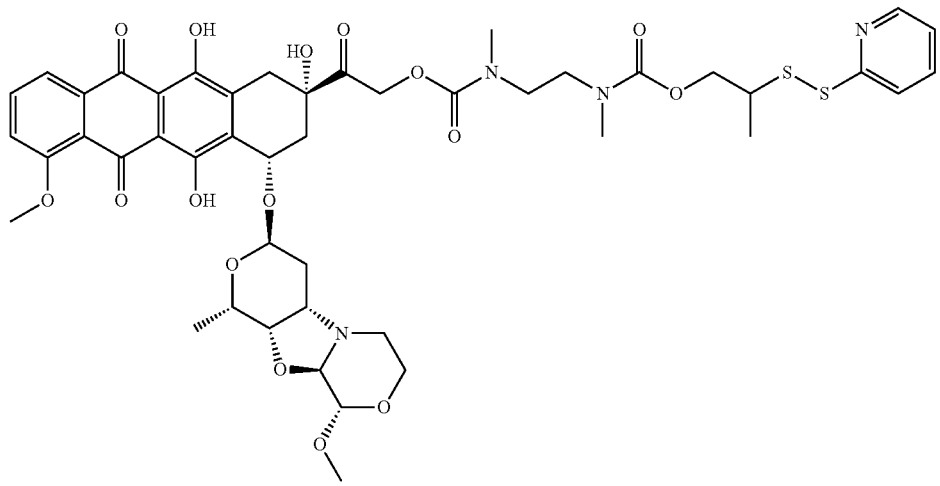
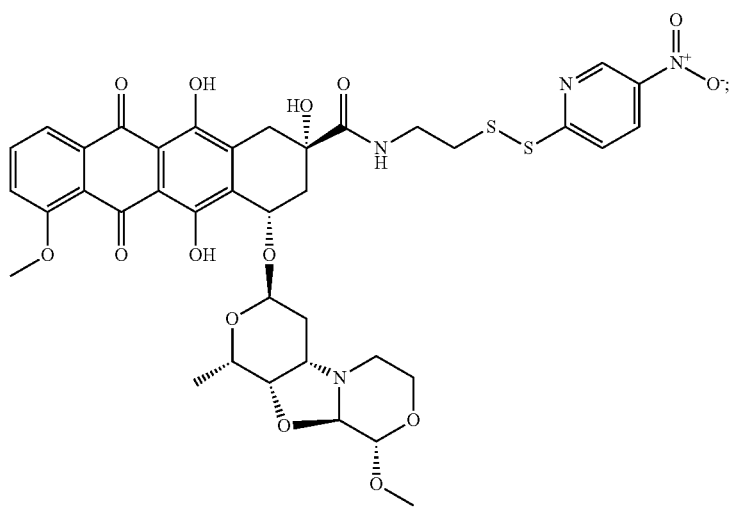
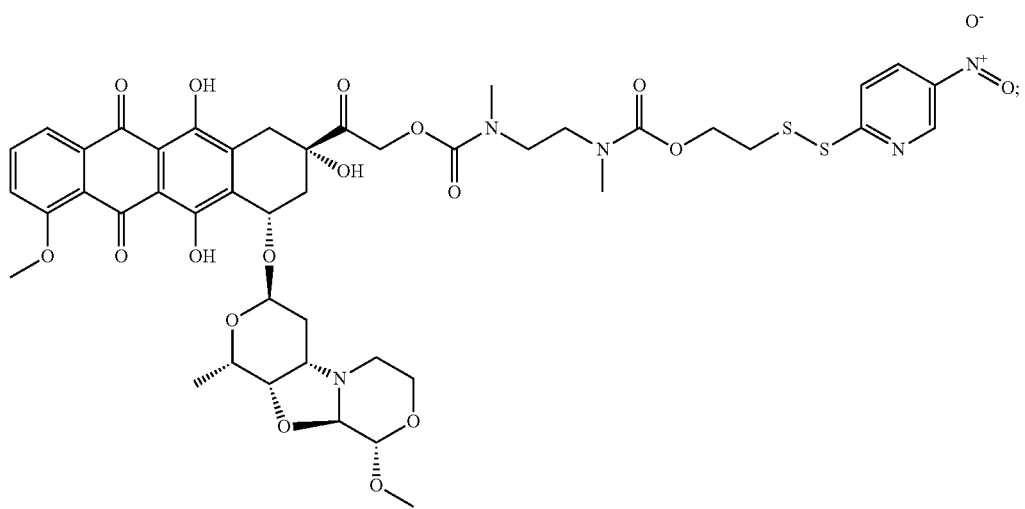

-continued
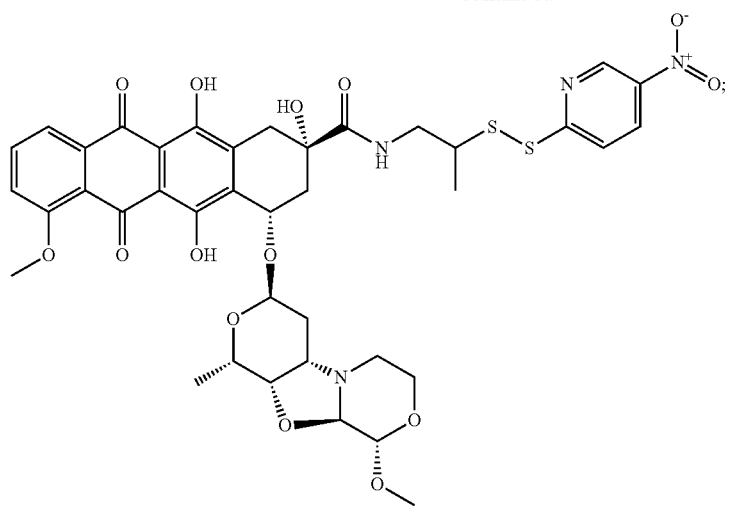
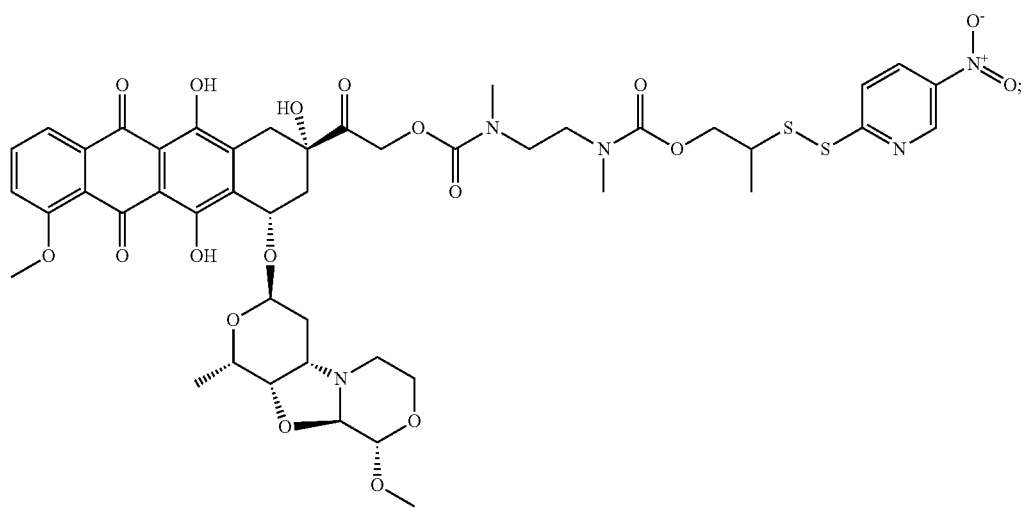
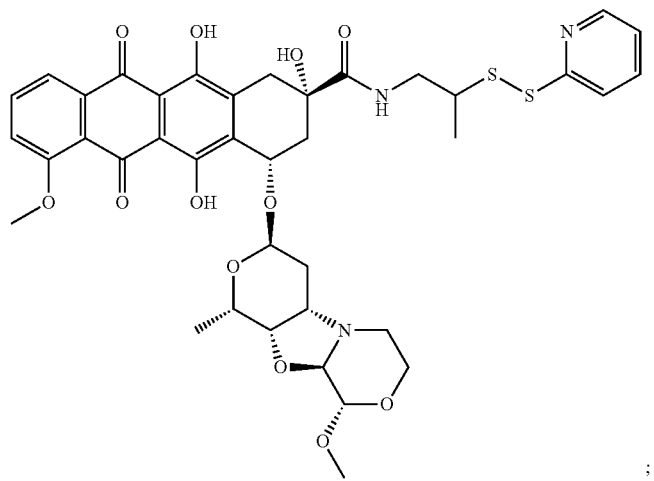

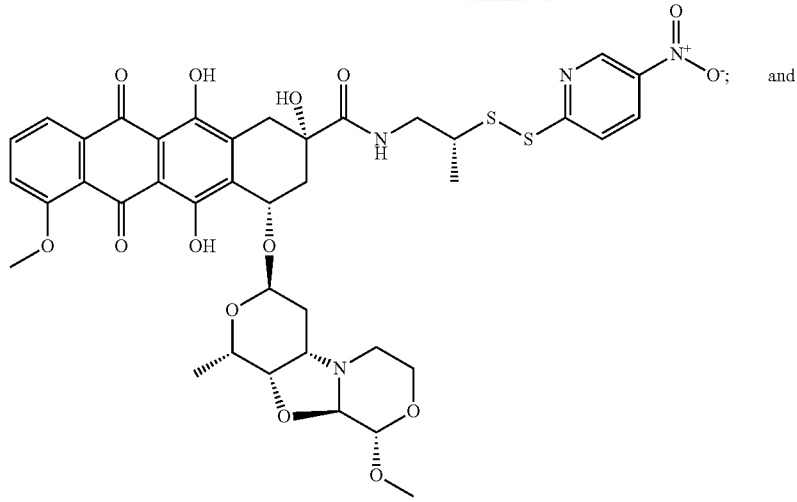
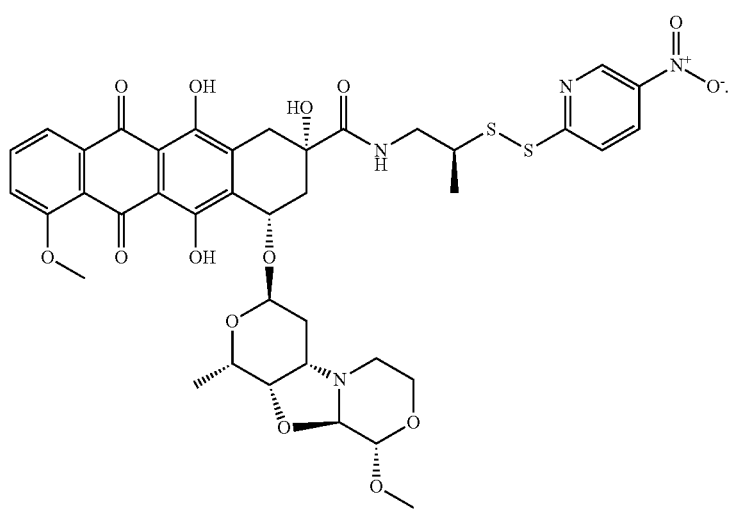
3. The linker-drug intermediate of claim 2 having the structure:
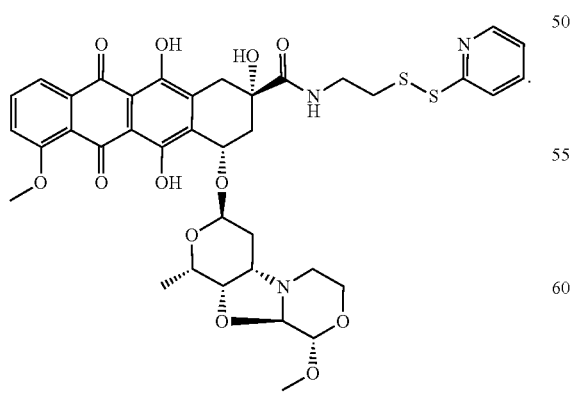
4. The linker-drug intermediate of claim 2 having the structure:

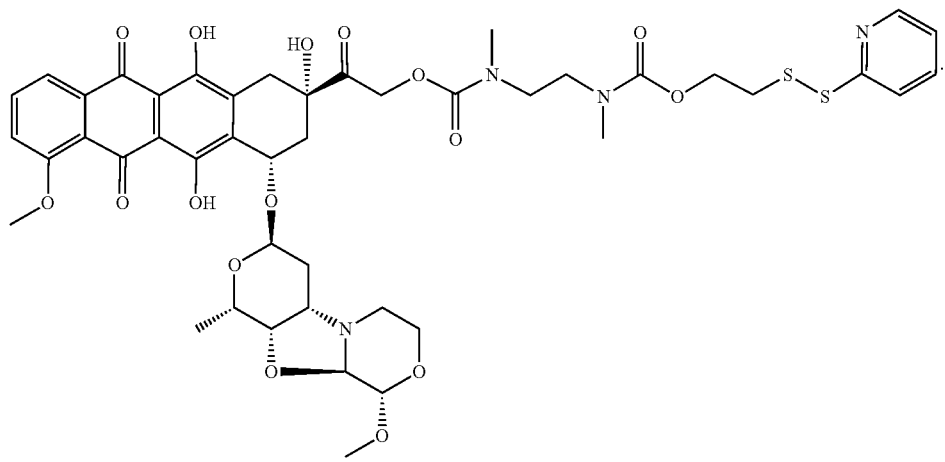 [SMILES: COc1cccc2c1C(=O)c1c(O)c3c(c(O)c1C2=O)C[C@@](O)(C(=O)COC(=O)N(C)CCN(C)C(=O)OCCSSc1ccccn1)C[C@@H]3O[C@H]1C[C@H]2[C@H](O[C@@H]3[C@@H](OC)OCCN32)[C@H](C)O1]
5. The linker-drug intermediate of claim 2 having the structure:
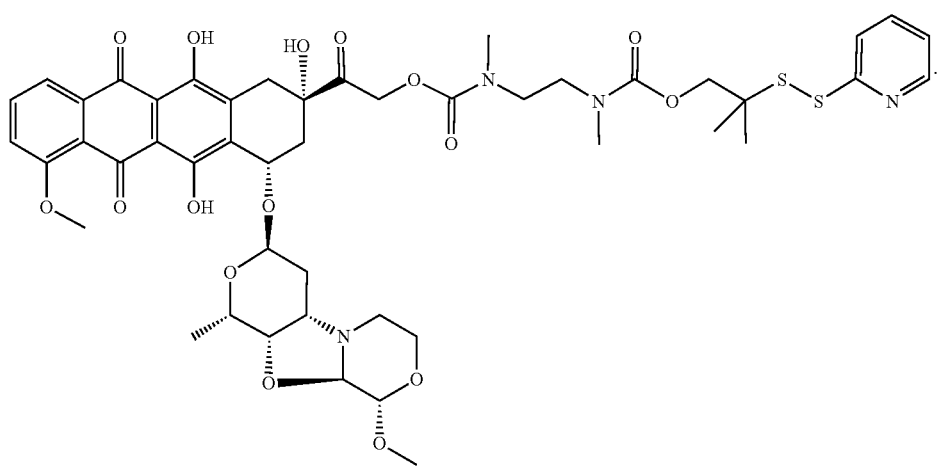 [SMILES: COc1cccc2c1C(=O)c1c(O)c3c(c(O)c1C2=O)C[C@@](O)(C(=O)COC(=O)N(C)CCN(C)C(=O)OCC(C)(C)SSc1ccccn1)C[C@@H]3O[C@H]1C[C@H]2[C@H](O[C@@H]3[C@@H](OC)OCCN32)[C@H](C)O1]
6. The linker-drug intermediate of claim 2 having the structure:
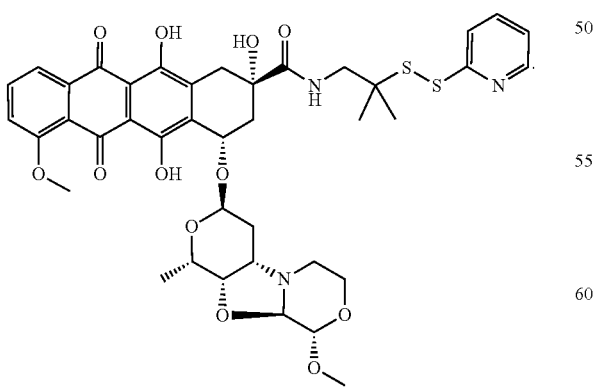
7. The linker-drug intermediate of claim 2 having the structure:

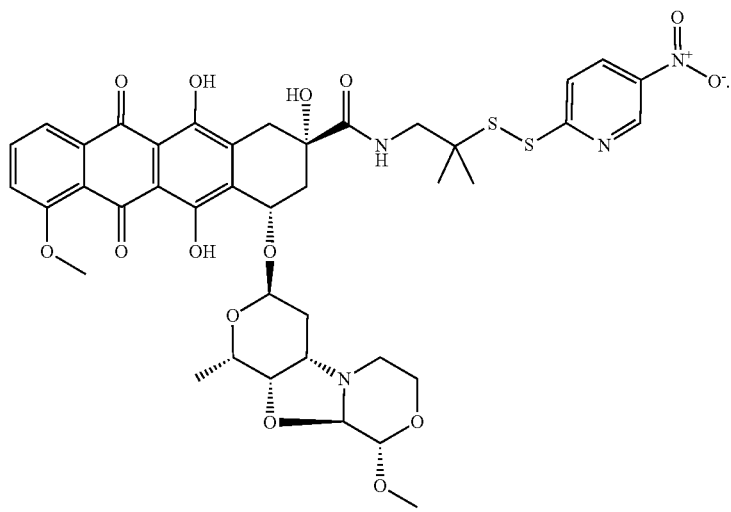
8. The linker-drug intermediate of claim 2 having the structure:
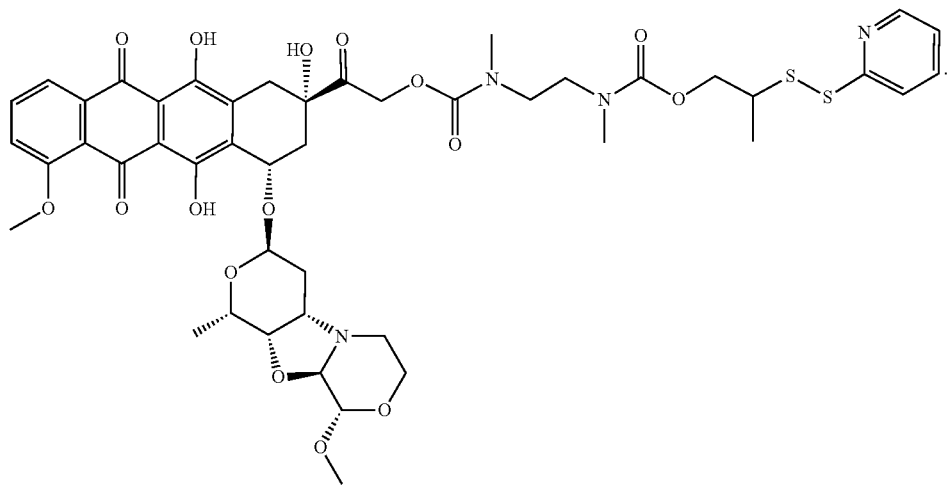 [SMILES: COc1cccc2c1C(=O)c1c(O)c3c(c(O)c1C2=O)C[C@@](O)(C(=O)COC(=O)N(C)CCN(C)C(=O)OCC(C)SSc1ccccn1)C[C@@H]3O[C@H]1C[C@H]2[C@H](O[C@@H]3[C@@H](OC)OCCN32)[C@H](C)O1]
9. The linker-drug intermediate of claim 2 having the structure:
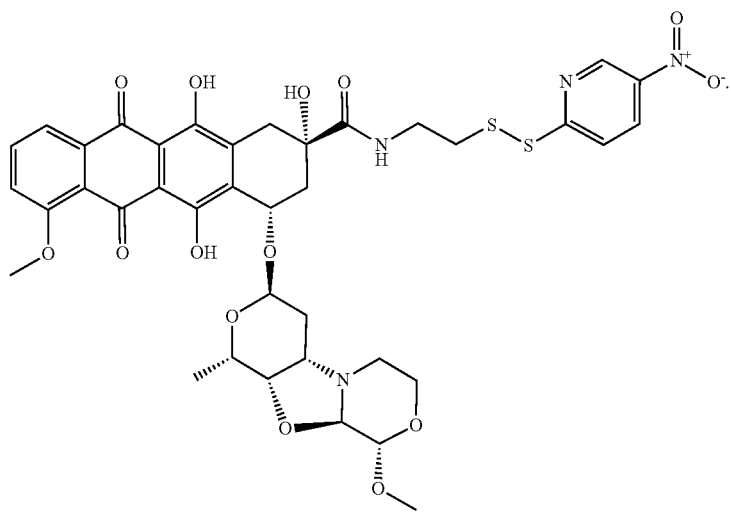

10. The linker-drug intermediate of claim 2 having the structure:
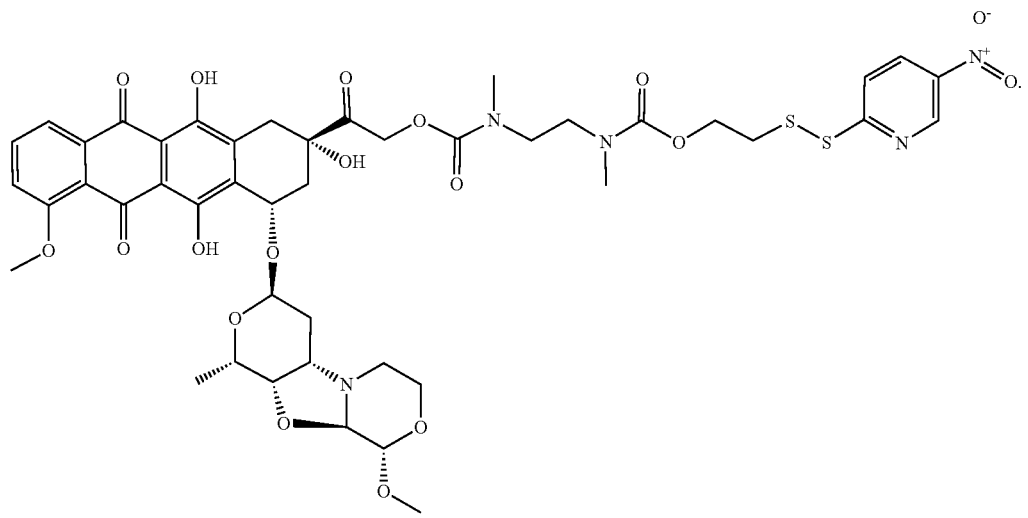
11. The linker-drug intermediate of claim 2 having the structure:
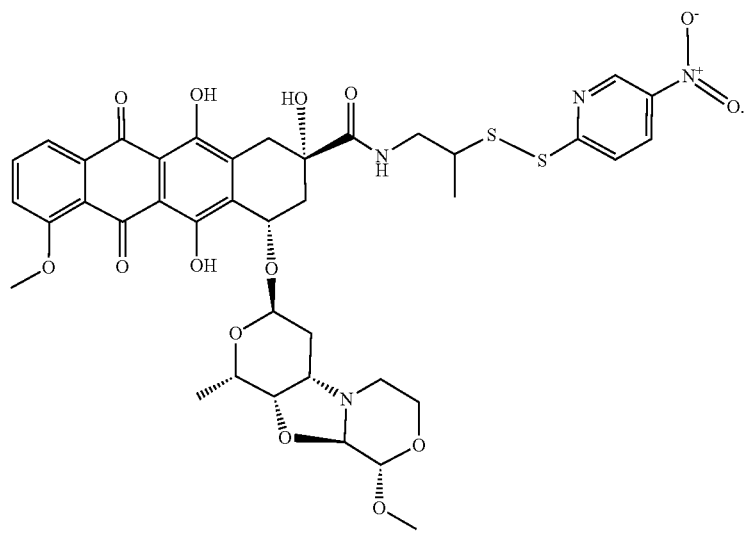
12. The linker-drug intermediate of claim 2 having the structure: